United States Patent
Waldraff et al.

(10) Patent No.: US 11,051,515 B2
(45) Date of Patent: Jul. 6, 2021

(54) 3-ACYL-BENZAMIDES AND THEIR USE AS HERBICIDES

(71) Applicant: Bayer Aktiengesellschaft, Leverkusen (DE)

(72) Inventors: Christian Waldraff, Bad Vilbel (DE); Arnim Koehn, Klein-Winternheim (DE); Hartmut Ahrens, Langen (DE); Ralf Braun, Ramberg (DE); Hansjoerg Dietrich, Liederbach am Taunus (DE); Anu Bheemaiah Machettira, Frankfurt am Main (DE); Christopher Hugh Rosinger, Hofheim (DE); Elmar Gatzweiler, Bad Nauheim (DE); Elisabeth Asmus, Hoesbach (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 16/633,943

(22) PCT Filed: Aug. 2, 2018

(86) PCT No.: PCT/EP2018/070991
§ 371 (c)(1),
(2) Date: Jan. 24, 2020

(87) PCT Pub. No.: WO2019/025540
PCT Pub. Date: Feb. 7, 2019

(65) Prior Publication Data
US 2020/0214294 A1    Jul. 9, 2020

(30) Foreign Application Priority Data

Aug. 4, 2017 (EP) .................... 17185026

(51) Int. Cl.
A01N 43/713     (2006.01)
C07C 69/78      (2006.01)
C07D 257/06     (2006.01)

(52) U.S. Cl.
CPC ............ *A01N 43/713* (2013.01); *C07C 69/78* (2013.01); *C07D 257/06* (2013.01); *C07C 2601/16* (2017.05)

(58) Field of Classification Search
CPC ..... A01N 43/713; C07C 69/78; C07D 257/06
See application file for complete search history.

(56) References Cited

U.S. PATENT DOCUMENTS

| | | |
|---|---|---|
| 8,481,749 B2 | 7/2013 | Braun et al. |
| 8,822,378 B2 | 9/2014 | Braun et al. |
| 2012/0058892 A1* | 3/2012 | Braun .................. A01N 43/653 504/103 |
| 2018/0192650 A1 | 7/2018 | Koehn et al. |
| 2018/0282290 A1 | 10/2018 | Koehn et al. |

FOREIGN PATENT DOCUMENTS

| | | | |
|---|---|---|---|
| EP | 3118199 A1 | 1/2017 | |
| WO | 2012/028579 A1 | 3/2012 | |
| WO | WO-2012028579 A1 * | 3/2012 | .......... C07D 257/06 |
| WO | 2013/017559 A1 | 2/2013 | |
| WO | 2017/005567 A1 | 1/2017 | |
| WO | 2017/055146 A1 | 4/2017 | |

OTHER PUBLICATIONS

International Search Report for Application No. PCT/EP2018/070991 dated Sep. 25, 2018.

* cited by examiner

*Primary Examiner* — Andrew S Rosenthal
(74) *Attorney, Agent, or Firm* — McBee Moore & Vanik IP, LLC

(57) ABSTRACT

The invention relates to 3-acyl-benzamides of formula (I) as herbicides. In formulae (I) X, Y, Z and $R^x$ represent radicals such as alkyl, cycloalkyl and halogen.

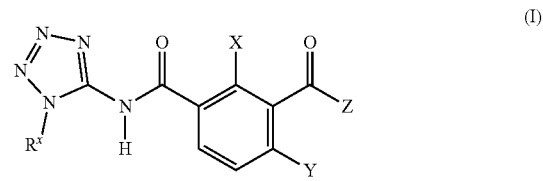

13 Claims, No Drawings

3-ACYL-BENZAMIDES AND THEIR USE AS HERBICIDES

CROSS-REFERENCE TO RELATED APPLICATIONS

This application is the National Stage entry of International Application No. PCT/EP2018/070991, filed 2 Aug. 2018, which claims priority to European Patent Application No. 17185026.6, filed 4 Aug. 2017.

BACKGROUND

Field

The invention relates to the technical field of the herbicides, especially that of the herbicides for selective control of weeds and weed grasses in crops of useful plants.

Description of Related Art

WO 2012/028579 A1 discloses herbicidally active benzamides which may carry various substituents in the 3-position of the phenyl ring. WO 2017/005567 A1, EP 3 118 199 A1 and WO 2017/055146 A1 also describe herbicidally active phenylamides which may carry various substituents in the 3-position of the phenyl ring. In addition, these publications each disclose, under Example Nos. 1-364 to 1-367 and 1-426 to 1-429, individual phenylamides carrying an acetyl or cyclopropylcarbonyl radical in the 3-position of the phenyl ring. However, the benzoylamides known from the publications mentioned above do not always have adequate herbicidal efficacy and/or compatibility with crop plants.

SUMMARY

It is an object of the present invention to provide alternative herbicidally active ingredients. This object is achieved by the benzamides according to the invention described below, which carry an acyl radical in the 3-position of the phenyl ring.

The present invention thus provides 3-acylbenzamides of the formula (I)

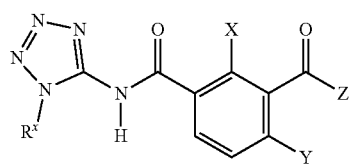

(I)

in which the symbols and indices are defined as follows:
$R^x$ represents $(C_1-C_6)$-alkyl,
X represents halogen, $(C_1-C_6)$-alkyl, halo-$(C_1-C_6)$-alkyl, $(C_3-C_6)$-cycloalkyl, $R^1O$, $R^2S(O)_n$ or $R^1O$—$(C_1-C_6)$-alkyl,
Y represents halogen, $(C_1-C_6)$-alkyl, halo-$(C_1-C_6)$-alkyl or $R^1O$, $R^2S(O)_n$,
Z represents $(C_1-C_6)$-alkyl, $(C_3-C_6)$-cycloalkyl, $(C_2-C_6)$-alkenyl, $(C_3-C_6)$-alkynyl, halo-$(C_1-C_6)$-alkyl, $(C_1-C_6)$-alkyl-O—$(C_1-C_6)$-alkyl, $(C_1-C_6)$-alkyl-C(O), $(C_1-C_6)$-alkyl-C(O)—$(C_1-C_6)$-alkyl, phenyl or heterocyclyl, where the radicals phenyl, heterocyclyl, $(C_2-C_6)$-alkenyl, $(C_3-C_6)$-alkynyl and $(C_3-C_6)$-cycloalkyl each carry m substituents $R^3$,
$R^1$ represents $(C_1-C_6)$-alkyl or halo-$(C_1-C_6)$-alkyl,
$R^2$ represents $(C_1-C_6)$-alkyl,
$R^3$ represents halogen, $(C_1-C_6)$-alkyl, $(C_1-C_3)$-alkyl-O—C(O), cyano or halo-$(C_1-C_6)$-alkyl,
m represents 0, 1, 2, 3 or 4,
n represents 0, 1 or 2.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, such as cyclopropyl, cyclobutyl, cyclopentyl or cyclohexyl.

Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur. For example, heterocyclyl is piperidinyl, pyrrolidinyl, tetrahydrofuranyl, dihydrofuranyl, oxetanyl, thienyl and furyl.

According to the nature of the substituents and the way in which they are joined, the compounds of the formula (I) may be present as stereoisomers. If, for example, one or more asymmetrically substituted carbon atoms are present, there may be enantiomers and diastereomers. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all stereoisomers and mixtures thereof which are encompassed by the formula (I) but not defined specifically.

Preference is given to compounds of the formula (I) in which the symbols and indices are defined as follows:
$R^x$ represents $(C_1-C_6)$-alkyl,
X represents halogen, $(C_1-C_6)$-alkyl, halo-$(C_1-C_6)$-alkyl, $(C_3-C_6)$-cycloalkyl, $R^1O$, $R^2S(O)_n$ or $R^1O$—$(C_1-C_6)$-alkyl,
Y represents halogen, $(C_1-C_6)$-alkyl, halo-$(C_1-C_6)$-alkyl or $R^1O$, $R^2S(O)_n$,
Z represents $(C_1-C_6)$-alkyl, $(C_3-C_6)$-cycloalkyl, $(C_2-C_6)$-alkenyl, $(C_3-C_6)$-alkynyl, halo-$(C_1-C_6)$-alkyl, $(C_1-C_6)$-alkyl-O—$(C_1-C_6)$-alkyl, $(C_1-C_6)$-alkyl-C(O), $(C_1-C_6)$-alkyl-C(O)—$(C_1-C_6)$-alkyl or phenyl, where the radicals phenyl, $(C_2-C_6)$-alkenyl, $(C_3-C_6)$-alkynyl and $(C_3-C_6)$-cycloalkyl each carry m substituents $R^3$,
$R^1$ represents $(C_1-C_6)$-alkyl or halo-$(C_1-C_6)$-alkyl,
$R^2$ represents $(C_1-C_6)$-alkyl,
$R^3$ represents halogen, $(C_1-C_6)$-alkyl, $(C_1-C_3)$-alkyl-O—C(O), cyano or halo-$(C_1-C_6)$-alkyl,
m represents 0, 1, 2, 3 or 4,
n represents 0, 1 or 2.

Particular preference is given to compounds of the formula (I) in which the symbols and indices are defined as follows:

$R^x$ represents $(C_1-C_6)$-alkyl,

X represents fluorine, chlorine, bromine, iodine, methyl, ethyl, cyclopropyl, trifluoromethyl, difluoromethyl, methoxymethyl, methoxy, methylsulfanyl, methylsulfinyl, methylsulfonyl, ethylsulfanyl or ethylsulfonyl, Y represents chlorine, bromine, iodine, methyl, ethyl, trifluoromethyl, difluoromethyl, methylsulfanyl, methylsulfinyl, methylsulfonyl or ethylsulfonyl, Z represents methyl, ethyl, n-propyl, isopropyl, cyclopropyl, n-butyl, tert-butyl, methoxymethyl, chloromethyl, acetyl, vinyl, 1-methylvinyl, 2-methylvinyl, (1,2-dimethyl)vinyl, (2,2-dimethyl)vinyl, 1-methylcyclopropyl, 2-methylcyclopropyl, (2,2-dimethyl)cyclopropyl, (1,2-dimethyl)cyclopropyl, 2-fluorocyclopropyl, (2,2-difluoro)cyclopropyl, cyclobutyl, cyclopentyl, cyclohexyl, 2-thienyl, 2-furyl, phenyl, 4-methoxyphenyl, 4-chlorophenyl, (3-trifluoromethyl)phenyl, 3,5-difluorophenyl, trifluoromethyl or difluoromethyl.

In all the formulae specified hereinafter, the substituents and symbols have the same meaning as described in formula (I), unless defined differently.

Compounds of the formula (II) are novel and are very well-suited as intermediates for the preparation of the compounds of the formula (I) according to the invention. The present invention therefore further provides compounds of the formula (II)

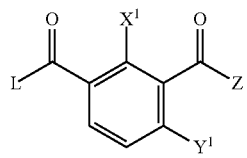

(II)

in which the symbols and indices are defined as follows:

L represents halogen or $R^4O$, $R^4$ represents hydrogen or $(C_1-C_6)$-alkyl, $X^1$ represents halogen, $(C_1-C_6)$-alkyl, $(C_3-C_6)$-cycloalkyl, $R^1O$ or $R^2S(O)_n$, $Y^1$ represents trifluoromethyl or difluoromethyl, $R^1$ represents $(C_1-C_6)$-alkyl or halo-$(C_1-C_6)$-alkyl, $R^2$ represents $(C_1-C_6)$-alkyl.

Preference is given to compounds (II) in which

L represents chlorine, methoxy or hydroxy, $X^1$ represents methyl, ethyl, cyclopropyl, methoxy, methylsulfanyl, ethylsulfanyl, fluorine, chlorine, bromine or iodine, $Y^1$ represents trifluoromethyl or difluoromethyl, Z represents methyl, ethyl, n-propyl, isopropyl, cyclopropyl, n-butyl, tert-butyl, methoxymethyl, chloromethyl, acetyl, vinyl, 1-methylvinyl, 2-methylvinyl, (1,2-dimethyl)vinyl, (2,2-dimethyl)vinyl, 1-methylcyclopropyl, 2-methylcyclopropyl, (2,2-dimethyl)cyclopropyl, (1,2-dimethyl)cyclopropyl, 2-fluorocyclopropyl, (2,2-difluoro)cyclopropyl, cyclobutyl, cyclopentyl, cyclohexyl, 2-thienyl, 2-furyl, phenyl, 4-methoxyphenyl, 4-chlorophenyl, (3-trifluoromethyl)phenyl, (3,5-difluoro)phenyl, trifluoromethyl or difluoromethyl, $R^1$ represents $(C_1-C_6)$-alkyl or halo-$(C_1-C_6)$-alkyl, $R^2$ represents $(C_1-C_6)$-alkyl.

Compounds of the formula (I) according to the invention can be prepared, for example, by the methods specified in WO2012/028579 A1. The compounds of the formula (II) required for this purpose can be synthesized using reactions known to the person skilled in the art, where the synthesis routes used depend inter alia on the substitution pattern of the compounds of the formula (I) or the formula (II). In the formulae shown in Schemes 1 and 2 below, the substituents L, $X^1$, $Y^1$ and Z each have the meanings mentioned above for compounds of the formula (II).

Scheme 1

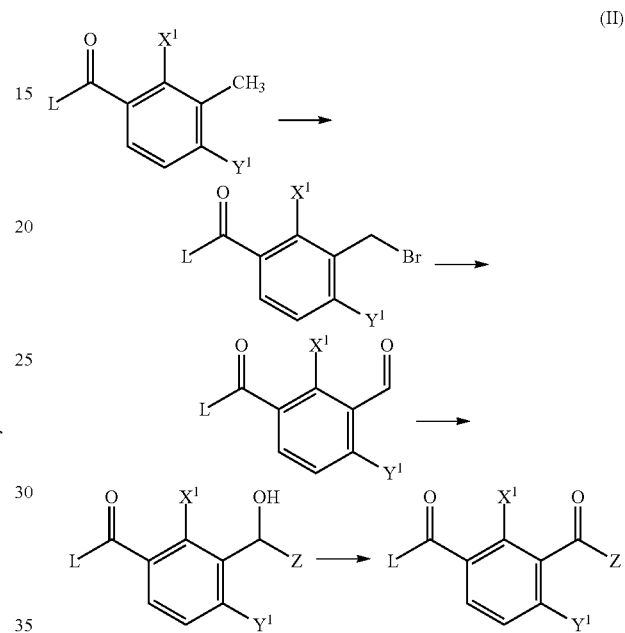

Compounds of the formula (II) can be prepared, for example, according to the reaction sequence given in Scheme 1—starting with substituted methylaromatics—by side-chain bromination, oxidation, nucleophilic introduction of group Z and subsequent oxidation. The substituted methylaromatics are known in principle and/or can be prepared by the methods given in WO2012/028579 A1.

Scheme 2

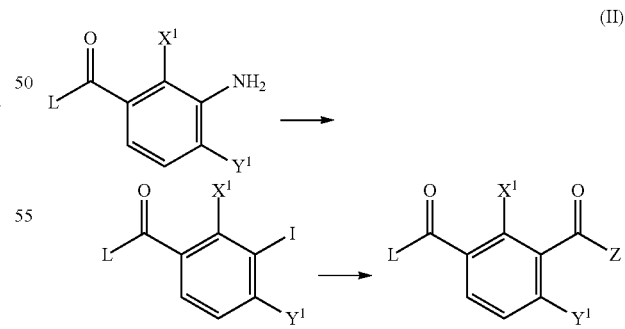

Compounds of the formula (II) can also be prepared, for example, according to the reaction sequence given in Scheme 2—starting with substituted aminoaromatics—by diazotization, Sandmeyer reaction and subsequent Grignard reaction.

Compounds of the formula (II) in which Z represents cyclopropyl can also be prepared from compounds of the formula (II) in which Z represents vinyl, by cyclopropanation for example with diazomethane or trimethylsulfoxonium halides.

Collections of compounds of the formula (I) which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from Perkin Elmer, Waltham, Mass. 02451, USA. For the parallelized purification of compounds of the formula (I) or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) can take place completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the implementation of individual or several synthesis steps may be supported by the use of microwave technology. The specialist literature describes a series of experimental protocols, for example in Microwaves in Organic and Medicinal Chemistry (editors: C. O. Kappe and A. Stadler), Wiley, 2005.

The preparation by the processes described herein gives compounds of the formula (I) in the form of substance collections, which are called libraries. The present invention also provides libraries comprising at least two compounds of the formula (I).

The compounds of the invention have excellent herbicidal efficacy against a broad spectrum of economically important mono- and dicotyledonous annual harmful plants. The active ingredients also act efficiently on perennial weeds which produce shoots from rhizomes, root stocks and other perennial organs and which are difficult to control.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though there is no intention to restrict the enumeration to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria* and *Sorghum*.

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola* and *Xanthium*.

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention, depending on their particular chemical structure and the application rate deployed, have outstanding growth-regulating properties in crop plants. They intervene in the plants' own metabolism with regulatory effect, and can thus be used for the controlled influencing of plant constituents and to facilitate harvesting, for example by triggering desiccation and stunted growth. In addition, they are also suitable for general control and inhibition of unwanted vegetative growth without killing the plants. Inhibition of vegetative growth plays a major role for many mono- and dicotyledonous crops since, for example, this can reduce or completely prevent lodging.

By virtue of their herbicidal and plant growth regulatory properties, the active ingredients can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material.

It is preferable with a view to transgenic crops to use the compounds of the invention in economically important transgenic crops of useful plants and ornamentals, for example of cereals such as wheat, barley, rye, oats, millet/ *Sorghum*, rice and corn or else crops of sugar beet, cotton, soybean, oilseed rape, potato, manioc, tomato, peas and other vegetables.

Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (for example WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants having a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd edition, Cold Spring Harbor Laboratory Press, Cold Spring Harbor, N.Y., or Winnacker "Gene and Klone" [Genes and clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227, Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the active ingredients of the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Engineering], volume 7, C. Hanser Verlag Munich, 4th Ed. 1986.

Wettable powders are preparations uniformly dispersible in water which, alongside the active ingredient apart from a diluent or inert substance, also comprise surfactants of an ionic and/or non-ionic type (wetting agent, dispersant), e.g. polyethoxylated alkylphenols, polyethoxylated fatty alcohols, polyethoxylated fatty amines, fatty alcohol polyglycolethersulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatuses such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active ingredient concentration is, for example, about 10 to 90% by weight, the remainder to 100% by weight consisting of customary formulation constituents. In emulsifiable concentrates, the active ingredient concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active compound is in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

The examples which follow illustrate the invention.

CHEMICAL EXAMPLES

Preparation of Compounds of the Formula (II)

Example 1: Preparation of methyl 3-acetyl-2-chloro-4-(trifluoromethyl)benzoate (Example No. 4-99)

Methyl 3-acetyl-2-chloro-4-(trifluoromethyl)benzoate is prepared according to the following scheme:

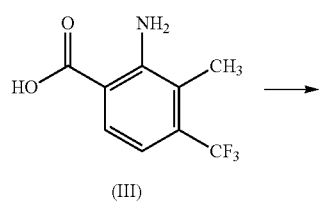

(III)

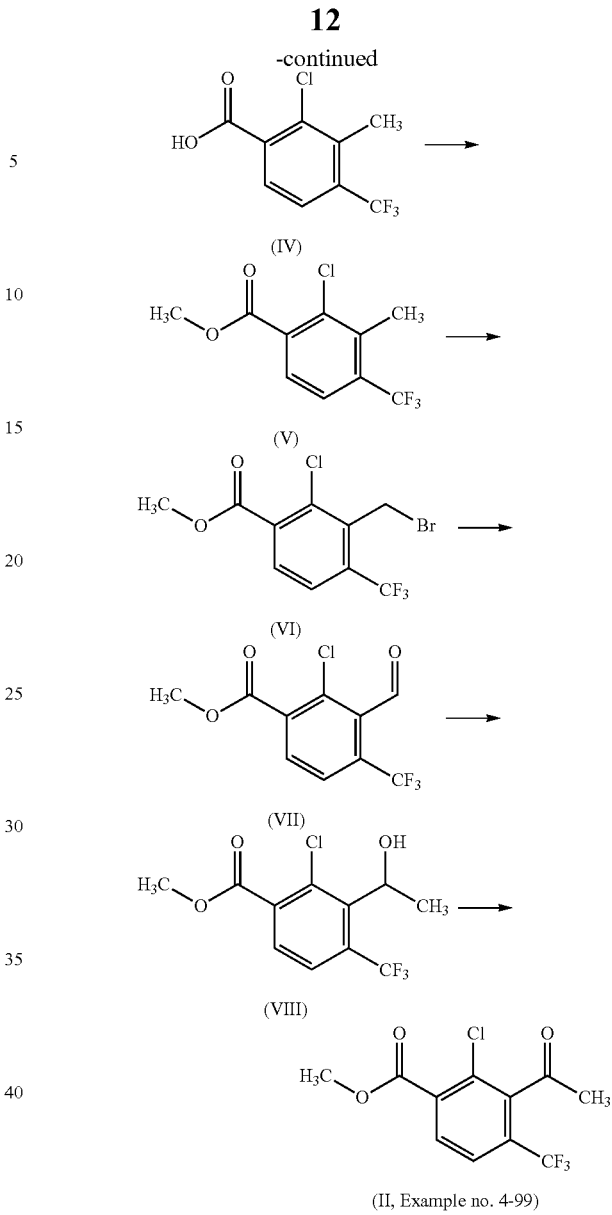

Step 1: Preparation of 2-chloro-3-methyl-4-(trifluoromethyl)benzoic Acid (IV)

75 g (324 mmol) of 2-amino-3-methyl-4-(trifluoromethyl)benzoic acid (III) (CAS 1508551-20-9) are initially charged in a mixture of 350 ml of water and 370 ml of concentrated hydrochloric acid. At 0-5° C., 24.79 g (359 mmol) of sodium nitrite, dissolved in 100 ml of water, are added dropwise. Separately, 50.81 g (513 mmol) of copper (I) chloride are dissolved in 150 ml of water and 200 ml of concentrated hydrochloric acid, and the mixture is heated to 60° C. At this temperature, the diazonium salt mixture is added dropwise. The resulting reaction mixture is stirred at 60° C. for 2 hours and then at (RT) room temperature overnight. The mixture is then cooled to 0° C. and the precipitate is filtered off. The latter is washed with water and dried at 150 mbar and 40° C. for 12 hours. This gives 76.4 g of 2-chloro-3-methyl-4-(trifluoromethyl)benzoic acid (IV).

Step 2: Preparation of methyl 2-chloro-3-methyl-4-(trifluoromethyl)benzoate (V)

60.1 g (252 mmol) of 2-chloro-3-methyl-4-(trifluoromethyl)benzoic acid (IV) are initially charged in 590 ml of methanol, and 80.56 ml (1.51 mol) of sulfuric acid are added at RT. The mixture is stirred at reflux for 2 hours. The mixture is then cooled to RT and the volatile constituents are removed under reduced pressure. The residue is dissolved in water and extracted with dichloromethane. The organic phases are dried and concentrated under reduced pressure. The residue is purified chromatographically (ethyl acetate/n-heptane). This gives 89.67 g of methyl 2-chloro-3-methyl-4-(trifluoromethyl)benzoate (V).

Step 3: Preparation of methyl 3-(bromomethyl)-2-chloro-4-(trifluoromethyl)benzoate (VI)

62.4 g (247 mmol) of methyl 2-chloro-3-methyl-4-(trifluoromethyl)benzoate (V) are suspended in 640 ml of chlorobenzene, and 52.7 g (296 mmol) of N-bromosuccinimide and 406 mg (2.47 mmol) of AIBN are added. The mixture is warmed to 60° C., 0.64 ml (12.35 mmol) of bromine are added and the mixture is heated to 110° C. After 12 hours of stirring at this temperature, a further 20 g of N-bromosuccinimide and 120 µl of bromine are added and the mixture is stirred at 110° C. for a further 6 hours. After cooling to RT, the reaction mixture is washed with an aqueous sodium thiosulfate solution. The organic phase is separated off, the aqueous phase is washed with $CH_2Cl_2$ (dichloromethane). The combined organic phases are dried and concentrated. The residue is purified chromatographically (ethyl acetate/n-heptane). This gives 77.1 g of methyl 3-(bromomethyl)-2-chloro-4-(trifluoromethyl)benzoate (VI).

Step 4: Preparation of methyl 2-chloro-3-formyl-4-(trifluoromethyl)benzoate (VII)

68.4 g (266 mmol) of methyl 3-(bromomethyl)-2-chloro-4-(trifluoromethyl)benzoate (VI) are initially charged in 500 ml of acetonitrile, and 7.25 g (619 mmol) of N-methylmorpholine N-oxide are added. After stirring at RT for 6 hours, the mixture is concentrated and the residue is taken up in ethyl acetate and washed twice with water. The organic phase is dried and concentrated. Chromatographic separation (ethyl acetate/n-heptane) affords 49.5 g of methyl 2-chloro-3-formyl-4-(trifluoromethyl)benzoate (VII).

Step 5: Preparation of methyl 2-chloro-3-(1-hydroxyethyl)-4-(trifluoromethyl)benzoate (VIII)

3 g (11 mmol) of methyl 2-chloro-3-formyl-4-(trifluoromethyl)benzoate (VII) are initially charged in 20 ml of anhydrous THF (tetrahydrofuran) and, at −70° C., 3.97 ml (14 mmol) of a solution of methylmagnesium bromide in THF are added carefully. Cooling is then removed and the mixture is stirred at RT for 12 hours. The mixture is then added to 2 molar hydrochloric acid and extracted with $CH_2Cl_2$. The organic phase is dried and concentrated. Chromatographic separation (ethyl acetate/n-heptane) affords methyl 2-chloro-3-(1-hydroxyethyl)-4-(trifluoromethyl)benzoate (VIII). $^1$H-NMR (400 MHz, DMSO-$d_6$): δ=7.81 (d, 1H); 7.71 (d, 1H); 5.60 (d, 1H); 5.32 (m, 1H); 3.90 (s, 3H); 1.51 (d, 3H).

Step 6: Preparation of methyl 3-acetyl-2-chloro-4-(trifluoromethyl)benzoate

At 0° C., 1.44 g (14 mmol) of chromium(VI) oxide are added to 1.47 ml of concentrated sulfuric acid, and this mixture is added dropwise to 10 ml of water at 0° C. 3.4 g (12 mmol) of methyl 2-chloro-3-(1-hydroxyethyl)-4-(trifluoromethyl)benzoate (VIII), dissolved in 23 ml of acetone, are then added dropwise at 0° C. This mixture is warmed to RT and stirred for another 3 hours. The reaction is then quenched with isopropanol, acetone and isopropanol are removed by distillation and the residue is extracted with ethyl acetate. The organic phase is dried and concentrated. This gives 2.66 g of methyl 3-acetyl-2-chloro-4-(trifluoromethyl)benzoate.

Example 2: Preparation of methyl 3-(cyclopropylcarbonyl)-2-methyl-4-(trifluoromethyl)benzoate (Example No. 4-5)

Step 1: Preparation of methyl 3-iodo-2-methyl-4-(trifluoromethyl)benzoate 40 g (172 mmol) of methyl 3-amino-2-methyl-4-(trifluoromethyl)benzoate (CAS 2092141-87-0) are dissolved in 400 ml of concentrated hydrochloric acid, and the mixture is cooled to 0-5° C. and stirred for 20 min. A solution of 13 g (189 mmol) of sodium nitrite in 60 ml of water is then slowly added dropwise and the mixture is stirred at 0-5° C. for 2 hours. 4.1 g (69 mmol) of urea are added, and after a further 10 minutes of stirring, a solution of 42.7 g (257 mmol) of potassium iodide in 30 ml of water is added dropwise, also at 0-5° C. The reaction mixture is then allowed to warm to RT, poured into 400 ml of ice-water and extracted with $CH_2Cl_2$. The organic phase is washed with a saturated aqueous sodium thiosulfate solution, dried and concentrated. The residue is purified chromatographically (ethyl acetate/n-heptane). This gives 51.4 g of methyl 3-iodo-2-methyl-4-(trifluoromethyl)benzoate.

Step 2: Preparation of methyl 3-(cyclopropylcarbonyl)-2-methyl-4-(trifluoromethyl)benzoate 5 g (13.7 mmol) of methyl 3-iodo-2-methyl-4-(trifluoromethyl)benzoate are initially charged in 20 ml of dry THF, and at −30° C., 13.7 ml of a 1.3 molar solution (17.8 mmol) of isopropylmagnesium chloride/lithium chloride in THF are added and the mixture is stirred at −30° C. for 1 hour. Also at −30° C., 4.23 g (27.4 mmol) of cyclopropanecarboxylic anhydride are then added dropwise. The resulting mixture is warmed to RT over a period of 2 hours. The THF is removed by distillation and the residue is taken up in water and a little 2 molar hydrochloric acid and extracted with $CH_2Cl_2$. The organic phase is dried and concentrated. Chromatographic purification (ethyl acetate/n-heptane) affords 3.6 g of methyl 3-(cyclopropylcarbonyl)-2-methyl-4-(trifluoromethyl)benzoate.

Preparation of Compounds of the Formula (I)

Example 1: Preparation of 3-acetyl-2-chloro-N-(1-methyl-1H-tetrazol-5-yl)-4-(trifluoromethyl)benzamide (Example No. 1-137)

150 mg (0.56 mmol) of 3-acetyl-2-chloro-4-(trifluoromethyl)benzoic acid and 74 mg (0.73 mmol) of 1-methyl-1H-tetrazole-5-amine are dissolved in 5 ml of $CH_2Cl_2$, and 0.5 ml (0.84 mmol) of a 50% strength solution of propanephosphonic anhydride in THF is added at RT. The mixture is stirred for 1 hour, and 0.4 ml of triethylamine and catalytic amounts of DMAP are then added. The mixture is then stirred at RT for a further 3 hours, and subsequently 5 ml of 2N hydrochloric acid, 5 ml of water and 5 ml of $CH_2Cl_2$ are added and the mixture is stirred for 10 minutes. The organic phase is separated off and concentrated. Chromatographic purification (acetonitrile/water+0.5% trifluoroacetic acid) affords 110 mg of 3-acetyl-2-chloro-N-(1-methyl-1H-tetrazol-5-yl)-4-(trifluoromethyl)benzamide.

Example 2: Preparation of 3-acetyl-2-chloro-N-(1-ethyl-1H-tetrazol-5-yl)-4-(trifluoromethyl)benzamide (Example No. 2-137)

200 mg (0.75 mmol) of 3-acetyl-2-chloro-4-(trifluoromethyl)benzoic acid are initially charged in 3 ml of pyridine, and 107 mg (0.9 mmol) of 1-ethyl-1H-tetrazole-5-amine are added. 0.1 mg (1.14 mmol) of oxalyl chloride is then added and the mixture is stirred at RT for 12 h. 5 ml of water are then added, and the mixture is stirred for another 10 minutes and extracted with $CH_2Cl_2$. The organic phase is separated off, dried and concentrated by evaporation. Chromatographic purification (acetonitrile/water+0.5% trifluoroacetic acid) gives 66 mg of 3-acetyl-2-chloro-N-(1-ethyl-1H-tetrazol-5-yl)-4-(trifluoromethyl)benzamide.

Example 3: Preparation of 3-(cyclopropylcarbonyl)-2-methyl-N-(1-methyl-1H-tetrazol-5-yl)-4-(trifluoromethyl)benzamide (Example No. 1-18)

Analogously to Example 2, 240 mg (0.88 mmol) of 3-(cyclopropylcarbonyl)-2-methyl-4-(trifluoromethyl)benzoic acid and 107 mg (1.05 mmol) of 1-methyl-1H-tetrazole-5-amine afford 196 mg of 3-(cyclopropylcarbonyl)-2-methyl-N-(1-methyl-1H-tetrazol-5-yl)-4-(trifluoromethyl)benzamide.

Example 4: Preparation of 3-(cyclopropylcarbonyl)-N-(1-ethyl-1H-tetrazol-5-yl)-2-methyl-4-(trifluoromethyl)benzamide (Example No. 2-18)

Likewise, 155 mg (0.56 mmol) of 3-(cyclopropylcarbonyl)-2-methyl-4-(trifluoromethyl)benzoic acid and 81 mg (0.68 mmol) of 1-ethyl-1H-tetrazole-5-amine afford 95 mg of 3-(cyclopropylcarbonyl)-N-(1-ethyl-1H-tetrazol-5-yl)-2-methyl-4-(trifluoromethyl)benzamide.

The examples listed in the tables below were prepared analogously to the methods mentioned above or can be obtained analogously to the methods mentioned above. These compounds are very particularly preferred.

The abbreviations used mean:

Ph = phenyl  Me = methyl  Et = ethyl  c-Pr = cyclopropyl
Bu = butyl   i-Pr = isopropyl

TABLE 1

Compounds of the formula (I) according to the invention in which $R^x$ represents a methyl group and the other substituents have the meanings listed below.

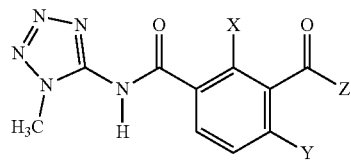

| No. | X | Y | Z |
|---|---|---|---|
| 1-1 | Me | Me | Me |
| 1-2 | Me | Me | Et |
| 1-3 | Me | Me | c-Pr |
| 1-4 | Me | SMe | Me |
| 1-5 | Me | SMe | Et |
| 1-6 | Me | SMe | c-Pr |
| 1-7 | Me | $SO_2Me$ | Me |
| 1-8 | Me | $SO_2Me$ | Et |
| 1-9 | Me | $SO_2Me$ | c-Pr |
| 1-10 | Me | $SO_2Me$ | $CH_2OMe$ |
| 1-11 | Me | $SO_2Me$ | $CH_2Cl$ |
| 1-12 | Me | $SO_2Me$ | (1-Me)-c-Pr |
| 1-13 | Me | $SO_2Me$ | (2-Me)-c-Pr |
| 1-14 | Me | $CF_3$ | Me |
| 1-15 | Me | $CF_3$ | Et |
| 1-16 | Me | $CF_3$ | n-Pr |
| 1-17 | Me | $CF_3$ | i-Pr |
| 1-18 | Me | $CF_3$ | c-Pr |
| 1-19 | Me | $CF_3$ | n-Bu |
| 1-20 | Me | $CF_3$ | t-Bu |
| 1-21 | Me | $CF_3$ | $CH_2OMe$ |
| 1-22 | Me | $CF_3$ | $CH_2Cl$ |
| 1-23 | Me | $CF_3$ | Ac |
| 1-24 | Me | $CF_3$ | (1-Me)-c-Pr |
| 1-25 | Me | $CF_3$ | (2-Me)-c-Pr |
| 1-26 | Me | $CF_3$ | $(2,2-Me_2)$-c-Pr |
| 1-27 | Me | $CF_3$ | $(1,2-Me_2)$-c-Pr |
| 1-28 | Me | $CF_3$ | (2-F)-c-Pr |
| 1-29 | Me | $CF_3$ | $(2,2-F_2)$-c-Pr |
| 1-30 | Me | $CF_3$ | c-Bu |
| 1-31 | Me | $CF_3$ | c-pentyl |
| 1-32 | Me | $CF_3$ | c-hexyl |
| 1-33 | Me | $CF_3$ | 2-thienyl |

TABLE 1-continued

Compounds of the formula (I) according to the invention in which $R^x$ represents a methyl group and the other substituents have the meanings listed below.

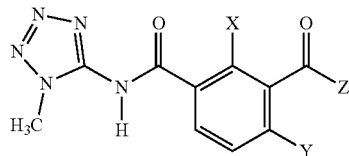

| No. | X | Y | Z |
|---|---|---|---|
| 1-34 | Me | $CF_3$ | 2-furyl |
| 1-35 | Me | $CF_3$ | Ph |
| 1-36 | Me | $CF_3$ | (4-MeO)-Ph |
| 1-37 | Me | $CF_3$ | (4-Cl)-Ph |
| 1-38 | Me | $CF_3$ | (3-$CF_3$)-Ph |
| 1-39 | Me | $CF_3$ | $CF_3$ |
| 1-40 | Me | $CF_3$ | $CHF_2$ |
| 1-41 | Me | $CHF_2$ | Me |
| 1-42 | Me | $CHF_2$ | Et |
| 1-43 | Me | $CHF_2$ | c-Pr |
| 1-44 | Me | $CHF_2$ | $CH_2OMe$ |
| 1-45 | Me | $CHF_2$ | $CH_2Cl$ |
| 1-46 | Me | $CHF_2$ | (1-Me)-c-Pr |
| 1-47 | Me | $CHF_2$ | (2-Me)-c-Pr |
| 1-48 | OMe | $CF_3$ | Me |
| 1-49 | OMe | $CF_3$ | Et |
| 1-50 | OMe | $CF_3$ | c-Pr |
| 1-51 | OMe | $CF_3$ | $CH_2OMe$ |
| 1-52 | OMe | $CF_3$ | $CH_2Cl$ |
| 1-53 | OMe | $CF_3$ | (1-Me)-c-Pr |
| 1-54 | OMe | $CF_3$ | (2-Me)-c-Pr |
| 1-55 | OMe | $CHF_2$ | Me |
| 1-56 | OMe | $CHF_2$ | Et |
| 1-57 | OMe | $CHF_2$ | c-Pr |
| 1-58 | SMe | $CF_3$ | Me |
| 1-59 | SMe | $CF_3$ | Et |
| 1-60 | SMe | $CF_3$ | c-Pr |
| 1-61 | SMe | $CF_3$ | $CH_2OMe$ |
| 1-62 | SMe | $CF_3$ | $CH_2Cl$ |
| 1-63 | SMe | $CF_3$ | (1-Me)-c-Pr |
| 1-64 | SMe | $CF_3$ | (2-Me)-c-Pr |
| 1-65 | SMe | $CHF_2$ | Me |
| 1-66 | SMe | $CHF_2$ | Et |
| 1-67 | SMe | $CHF_2$ | c-Pr |
| 1-68 | SMe | $CHF_2$ | $CH_2OMe$ |
| 1-69 | SMe | $CHF_2$ | $CH_2Cl$ |
| 1-70 | SMe | $CHF_2$ | (1-Me)-c-Pr |
| 1-71 | SMe | $CHF_2$ | (2-Me)-c-Pr |
| 1-72 | SMe | $SO_2Me$ | Me |
| 1-73 | SMe | $SO_2Me$ | Et |
| 1-74 | SMe | $SO_2Me$ | c-Pr |
| 1-75 | SMe | $SO_2Me$ | $CH_2OMe$ |
| 1-76 | SMe | $SO_2Me$ | $CH_2Cl$ |
| 1-77 | SMe | $SO_2Me$ | (1-Me)-c-Pr |
| 1-78 | SMe | $SO_2Me$ | (2-Me)-c-Pr |
| 1-79 | SEt | $CF_3$ | Me |
| 1-80 | SEt | $CF_3$ | Et |
| 1-81 | SEt | $CF_3$ | c-Pr |
| 1-82 | SEt | $CF_3$ | $CH_2OMe$ |
| 1-83 | SEt | $CF_3$ | $CH_2Cl$ |
| 1-84 | SEt | $CF_3$ | (1-Me)-c-Pr |
| 1-85 | SEt | $CF_3$ | (2-Me)-c-Pr |
| 1-86 | SEt | $CHF_2$ | Me |
| 1-87 | SEt | $CHF_2$ | Et |
| 1-88 | SEt | $CHF_2$ | c-Pr |
| 1-89 | SEt | $CHF_2$ | $CH_2OMe$ |
| 1-90 | SEt | $CHF_2$ | $CH_2Cl$ |
| 1-91 | SEt | $CHF_2$ | (1-Me)-c-Pr |
| 1-92 | SEt | $CHF_2$ | (2-Me)-c-Pr |
| 1-93 | SOMe | $CF_3$ | Me |
| 1-94 | SOMe | $CF_3$ | Et |
| 1-95 | SOMe | $CF_3$ | c-Pr |
| 1-96 | SOMe | $CHF_2$ | Me |
| 1-97 | SOMe | $CHF_2$ | Et |
| 1-98 | SOMe | $CHF_2$ | c-Pr |
| 1-99 | $SO_2Me$ | $CF_3$ | Me |

TABLE 1-continued

Compounds of the formula (I) according to the invention in which R$^x$ represents a methyl group and the other substituents have the meanings listed below.

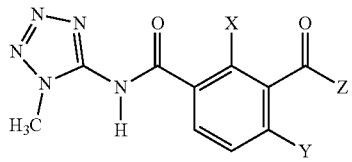

| No. | X | Y | Z |
|---|---|---|---|
| 1-100 | SO$_2$Me | CF$_3$ | Et |
| 1-101 | SO$_2$Me | CF$_3$ | c-Pr |
| 1-102 | SO$_2$Me | CHF$_2$ | Me |
| 1-103 | SO$_2$Me | CHF$_2$ | Et |
| 1-104 | SO$_2$Me | CHF$_2$ | c-Pr |
| 1-105 | SO$_2$Et | CF$_3$ | Me |
| 1-106 | SO$_2$Et | CF$_3$ | Et |
| 1-107 | SO$_2$Et | CF$_3$ | c-Pr |
| 1-108 | F | CF$_3$ | Me |
| 1-109 | F | CF$_3$ | Et |
| 1-110 | F | CF$_3$ | c-Pr |
| 1-111 | F | CHF$_2$ | Me |
| 1-112 | F | CHF$_2$ | Et |
| 1-113 | F | CHF$_2$ | c-Pr |
| 1-114 | Cl | Cl | Me |
| 1-115 | Cl | Cl | Et |
| 1-116 | Cl | Cl | c-Pr |
| 1-117 | Cl | Cl | CH$_2$OMe |
| 1-118 | Cl | Cl | CH$_2$Cl |
| 1-119 | Cl | Cl | (1-Me)-c-Pr |
| 1-120 | Cl | Cl | (2-Me)-c-Pr |
| 1-121 | Cl | SMe | Me |
| 1-122 | Cl | SMe | Et |
| 1-123 | Cl | SMe | c-Pr |
| 1-124 | Cl | SOMe | Me |
| 1-125 | Cl | SOMe | Et |
| 1-126 | Cl | SOMe | c-Pr |
| 1-127 | Cl | SO$_2$Me | Me |
| 1-128 | Cl | SO$_2$Me | Et |
| 1-129 | Cl | SO$_2$Me | c-Pr |
| 1-130 | Cl | SO$_2$Me | CH$_2$OMe |
| 1-131 | Cl | SO$_2$Me | CH$_2$Cl |
| 1-132 | Cl | SO$_2$Me | (1-Me)-c-Pr |
| 1-133 | Cl | SO$_2$Me | (2-Me)-c-Pr |
| 1-134 | Cl | Me | Me |
| 1-135 | Cl | Me | Et |
| 1-136 | Cl | Me | c-Pr |
| 1-137 | Cl | CF$_3$ | Me |
| 1-138 | Cl | CF$_3$ | Et |
| 1-139 | Cl | CF$_3$ | n-Pr |
| 1-140 | Cl | CF$_3$ | i-Pr |
| 1-141 | Cl | CF$_3$ | c-Pr |
| 1-142 | Cl | CF$_3$ | n-Bu |
| 1-143 | Cl | CF$_3$ | t-Bu |
| 1-144 | Cl | CF$_3$ | CH$_2$OMe |
| 1-145 | Cl | CF$_3$ | CH$_2$Cl |
| 1-146 | Cl | CF$_3$ | Ac |
| 1-147 | Cl | CF$_3$ | (1-Me)-c-Pr |
| 1-148 | Cl | CF$_3$ | (2-Me)-c-Pr |
| 1-149 | Cl | CF$_3$ | (2,2-Me$_2$)-c-Pr |
| 1-150 | Cl | CF$_3$ | (1,2-Me$_2$)-c-Pr |
| 1-151 | Cl | CF$_3$ | (2-F)-c-Pr |
| 1-152 | Cl | CF$_3$ | (2,2-F$_2$)-c-Pr |
| 1-153 | Cl | CF$_3$ | c-Bu |
| 1-154 | Cl | CF$_3$ | c-pentyl |
| 1-155 | Cl | CF$_3$ | c-hexyl |
| 1-156 | Cl | CF$_3$ | 2-thienyl |
| 1-157 | Cl | CF$_3$ | 2-furyl |
| 1-158 | Cl | CF$_3$ | Ph |
| 1-159 | Cl | CF$_3$ | (4-MeO)-Ph |
| 1-160 | Cl | CF$_3$ | (4-Cl)-Ph |
| 1-161 | Cl | CF$_3$ | (3-CF$_3$)-Ph |
| 1-162 | Cl | CF$_3$ | CF$_3$ |
| 1-163 | Cl | CF$_3$ | CHF$_2$ |
| 1-164 | Cl | CHF$_2$ | Me |
| 1-165 | Cl | CHF$_2$ | Et |

TABLE 1-continued

Compounds of the formula (I) according to the invention in which R^x represents a methyl group and the other substituents have the meanings listed below.

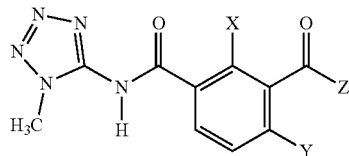

| No. | X | Y | Z |
|---|---|---|---|
| 1-166 | Cl | CHF$_2$ | n-Pr |
| 1-167 | Cl | CHF$_2$ | i-Pr |
| 1-168 | Cl | CHF$_2$ | c-Pr |
| 1-169 | Cl | CHF$_2$ | n-Bu |
| 1-171 | Cl | CHF$_2$ | t-Bu |
| 1-172 | Cl | CHF$_2$ | CH$_2$OMe |
| 1-173 | Cl | CHF$_2$ | CH$_2$Cl |
| 1-174 | Cl | CHF$_2$ | Ac |
| 1-175 | Cl | CHF$_2$ | (1-Me)-c-Pr |
| 1-176 | Cl | CHF$_2$ | (2-Me)-c-Pr |
| 1-177 | Cl | CHF$_2$ | (2,2-Me$_2$)-c-Pr |
| 1-178 | Cl | CHF$_2$ | (1,2-Me$_2$)-c-Pr |
| 1-179 | Cl | CHF$_2$ | (2-F)-c-Pr |
| 1-180 | Cl | CHF$_2$ | (2,2-F$_2$)-c-Pr |
| 1-181 | Cl | CHF$_2$ | c-Bu |
| 1-182 | Cl | CHF$_2$ | c-pentyl |
| 1-183 | Cl | CHF$_2$ | c-hexyl |
| 1-184 | Cl | CHF$_2$ | 2-thienyl |
| 1-185 | Cl | CHF$_2$ | 2-furyl |
| 1-186 | Cl | CHF$_2$ | Ph |
| 1-187 | Cl | CHF$_2$ | (4-MeO)-Ph |
| 1-188 | Cl | CHF$_2$ | (4-Cl)-Ph |
| 1-189 | Cl | CHF$_2$ | (3-CF$_3$)-Ph |
| 1-190 | Cl | CHF$_2$ | CF$_3$ |
| 1-191 | Cl | CHF$_2$ | CHF$_2$ |
| 1-192 | Cl | I | Me |
| 1-193 | Cl | I | Et |
| 1-194 | Cl | I | c-Pr |
| 1-195 | Br | CF$_3$ | Me |
| 1-196 | Br | CF$_3$ | Et |
| 1-197 | Br | CF$_3$ | c-Pr |
| 1-198 | Br | CF$_3$ | CH$_2$OMe |
| 1-199 | Br | CF$_3$ | CH$_2$Cl |
| 1-200 | Br | CF$_3$ | (1-Me)-c-Pr |
| 1-201 | Br | CF$_3$ | (2-Me)-c-Pr |
| 1-202 | Br | CHF$_2$ | Me |
| 1-203 | Br | CHF$_2$ | Et |
| 1-204 | Br | CHF$_2$ | c-Pr |
| 1-205 | Br | CHF$_2$ | CH$_2$OMe |
| 1-206 | Br | CHF$_2$ | CH$_2$Cl |
| 1-207 | Br | CHF$_2$ | (1-Me)-c-Pr |
| 1-208 | Br | CHF$_2$ | (2-Me)-c-Pr |
| 1-209 | Br | SO$_2$Me | Me |
| 1-210 | Br | SO$_2$Me | Et |
| 1-211 | Br | SO$_2$Me | c-Pr |
| 1-212 | Br | SO$_2$Me | CH$_2$OMe |
| 1-213 | Br | SO$_2$Me | CH$_2$Cl |
| 1-214 | Br | SO$_2$Me | (1-Me)-c-Pr |
| 1-215 | Br | SO$_2$Me | (2-Me)-c-Pr |
| 1-216 | CH$_2$OMe | CF$_3$ | Me |
| 1-217 | CH$_2$OMe | CF$_3$ | Et |
| 1-218 | CH$_2$OMe | CF$_3$ | c-Pr |
| 1-219 | CH$_2$OMe | SO$_2$Me | Me |
| 1-220 | CH$_2$OMe | SO$_2$Me | Et |
| 1-221 | CH$_2$OMe | SO$_2$Me | c-Pr |
| 1-222 | Et | CF$_3$ | Me |
| 1-223 | Et | CF$_3$ | Et |
| 1-224 | Et | CF$_3$ | c-Pr |
| 1-225 | Et | CHF$_2$ | Me |
| 1-226 | Et | CHF$_2$ | Et |
| 1-227 | Et | CHF$_2$ | c-Pr |
| 1-228 | Et | SO$_2$Me | Me |
| 1-229 | Et | SO$_2$Me | Et |
| 1-230 | Et | SO$_2$Me | c-Pr |
| 1-231 | c-Pr | CF$_3$ | Me |
| 1-232 | c-Pr | CF$_3$ | Et |

TABLE 1-continued

Compounds of the formula (I) according to the invention in which R^x represents a methyl group and the other substituents have the meanings listed below.

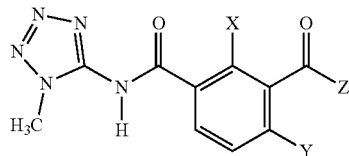

| No. | X | Y | Z |
|---|---|---|---|
| 1-233 | c-Pr | $CF_3$ | c-Pr |
| 1-234 | c-Pr | $CF_3$ | $CH_2OMe$ |
| 1-235 | c-Pr | $CF_3$ | $CH_2Cl$ |
| 1-236 | c-Pr | $CF_3$ | (1-Me)-c-Pr |
| 1-237 | c-Pr | $CF_3$ | (2-Me)-c-Pr |
| 1-238 | c-Pr | $CHF_2$ | Me |
| 1-239 | c-Pr | $CHF_2$ | Et |
| 1-240 | c-Pr | $CHF_2$ | c-Pr |
| 1-241 | c-Pr | $CHF_2$ | $CH_2OMe$ |
| 1-242 | c-Pr | $CHF_2$ | $CH_2Cl$ |
| 1-243 | c-Pr | $CHF_2$ | (1-Me)-c-Pr |
| 1-244 | c-Pr | $CHF_2$ | (2-Me)-c-Pr |
| 1-245 | c-Pr | $SO_2Me$ | Me |
| 1-246 | c-Pr | $SO_2Me$ | Et |
| 1-247 | c-Pr | $SO_2Me$ | c-Pr |
| 1-248 | c-Pr | $SO_2Me$ | $CH_2OMe$ |
| 1-249 | c-Pr | $SO_2Me$ | $CH_2Cl$ |
| 1-250 | c-Pr | $SO_2Me$ | (1-Me)-c-Pr |
| 1-251 | c-Pr | $SO_2Me$ | (2-Me)-c-Pr |
| 1-252 | I | $CF_3$ | Me |
| 1-253 | I | $CF_3$ | Et |
| 1-254 | I | $CF_3$ | c-Pr |
| 1-255 | I | $CF_3$ | $CH_2OMe$ |
| 1-256 | I | $CF_3$ | $CH_2Cl$ |
| 1-257 | I | $CF_3$ | (1-Me)-c-Pr |
| 1-258 | I | $CF_3$ | (2-Me)-c-Pr |
| 1-259 | I | $CHF_2$ | Me |
| 1-260 | I | $CHF_2$ | Et |
| 1-261 | I | $CHF_2$ | c-Pr |
| 1-262 | I | $CHF_2$ | $CH_2OMe$ |
| 1-263 | I | $CHF_2$ | $CH_2Cl$ |
| 1-264 | I | $CHF_2$ | (1-Me)-c-Pr |
| 1-265 | I | $CHF_2$ | (2-Me)-c-Pr |
| 1-266 | I | $SO_2Me$ | Me |
| 1-267 | I | $SO_2Me$ | Et |
| 1-268 | I | $SO_2Me$ | c-Pr |
| 1-269 | I | $SO_2Me$ | $CH_2OMe$ |
| 1-270 | I | $SO_2Me$ | $CH_2Cl$ |
| 1-271 | I | $SO_2Me$ | (1-Me)-c-Pr |
| 1-272 | I | $SO_2Me$ | (2-Me)-c-Pr |
| 1-273 | $CF_3$ | $CF_3$ | Me |
| 1-274 | $CF_3$ | $CF_3$ | Et |
| 1-275 | $CF_3$ | $CF_3$ | c-Pr |
| 1-276 | $CF_3$ | $CF_3$ | $CH_2OMe$ |
| 1-277 | $CF_3$ | $CF_3$ | $CH_2Cl$ |
| 1-278 | $CF_3$ | $CF_3$ | (1-Me)-c-Pr |
| 1-279 | $CF_3$ | $CF_3$ | (2-Me)-c-Pr |
| 1-280 | Cl | Cl | i-Pr |
| 1-281 | Cl | Cl | c-pentyl |
| 1-282 | Cl | Cl | 2-thienyl |
| 1-283 | Cl | Cl | (4-MeO)-Ph |
| 1-284 | SMe | $CF_3$ | c-Bu |
| 1-285 | SMe | $CF_3$ | c-pentyl |
| 1-286 | SMe | $CF_3$ | c-hexyl |
| 1-287 | Cl | $CF_3$ | $(3,5-F_2)$-Ph |
| 1-288 | SMe | $CF_3$ | $(3,5-F_2)$-Ph |
| 1-289 | Cl | Br | Me |
| 1-290 | Cl | Br | Et |
| 1-291 | Cl | Br | c-Pr |
| 1-292 | Me | Cl | Me |
| 1-293 | Me | Cl | Et |
| 1-294 | Me | Cl | c-Pr |
| 1-295 | Cl | $CF_3$ | vinyl |

TABLE 2

Compounds of the formula (I) according to the invention in which $R^x$ represents an ethyl group and the other substituents have the meanings listed below.

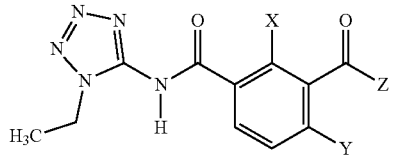

| No. | X | Y | Z |
|---|---|---|---|
| 2-1 | Me | Me | Me |
| 2-2 | Me | Me | Et |
| 2-3 | Me | Me | c-Pr |
| 2-4 | Me | SMe | Me |
| 2-5 | Me | SMe | Et |
| 2-6 | Me | SMe | c-Pr |
| 2-7 | Me | $SO_2Me$ | Me |
| 2-8 | Me | $SO_2Me$ | Et |
| 2-9 | Me | $SO_2Me$ | c-Pr |
| 2-10 | Me | $SO_2Me$ | $CH_2OMe$ |
| 2-11 | Me | $SO_2Me$ | $CH_2Cl$ |
| 2-12 | Me | $SO_2Me$ | (1-Me)-c-Pr |
| 2-13 | Me | $SO_2Me$ | (2-Me)-c-Pr |
| 2-14 | Me | $CF_3$ | Me |
| 2-15 | Me | $CF_3$ | Et |
| 2-16 | Me | $CF_3$ | n-Pr |
| 2-17 | Me | $CF_3$ | i-Pr |
| 2-18 | Me | $CF_3$ | c-Pr |
| 2-19 | Me | $CF_3$ | n-Bu |
| 2-20 | Me | $CF_3$ | t-Bu |
| 2-21 | Me | $CF_3$ | $CH_2OMe$ |
| 2-22 | Me | $CF_3$ | $CH_2Cl$ |
| 2-23 | Me | $CF_3$ | Ac |
| 2-24 | Me | $CF_3$ | (1-Me)-c-Pr |
| 2-25 | Me | $CF_3$ | (2-Me)-c-Pr |
| 2-26 | Me | $CF_3$ | $(2,2-Me_2)$-c-Pr |
| 2-27 | Me | $CF_3$ | $(1,2-Me_2)$-c-Pr |
| 2-28 | Me | $CF_3$ | (2-F)-c-Pr |
| 2-29 | Me | $CF_3$ | $(2,2-F_2)$-c-Pr |
| 2-30 | Me | $CF_3$ | c-Bu |
| 2-31 | Me | $CF_3$ | c-pentyl |
| 2-32 | Me | $CF_3$ | c-hexyl |
| 2-33 | Me | $CF_3$ | 2-thienyl |
| 2-34 | Me | $CF_3$ | 2-furyl |
| 2-35 | Me | $CF_3$ | Ph |
| 2-36 | Me | $CF_3$ | (4-MeO)-Ph |
| 2-37 | Me | $CF_3$ | (4-Cl)-Ph |
| 2-38 | Me | $CF_3$ | $(3-CF_3)$-Ph |
| 2-39 | Me | $CF_3$ | $CF_3$ |
| 2-40 | Me | $CF_3$ | $CHF_2$ |
| 2-41 | Me | $CHF_2$ | Me |
| 2-42 | Me | $CHF_2$ | Et |
| 2-43 | Me | $CHF_2$ | c-Pr |
| 2-44 | Me | $CHF_2$ | $CH_2OMe$ |
| 2-45 | Me | $CHF_2$ | $CH_2Cl$ |
| 2-46 | Me | $CHF_2$ | (1-Me)-c-Pr |
| 2-47 | Me | $CHF_2$ | (2-Me)-c-Pr |
| 2-48 | OMe | $CF_3$ | Me |
| 2-49 | OMe | $CF_3$ | Et |
| 2-50 | OMe | $CF_3$ | c-Pr |
| 2-51 | OMe | $CF_3$ | $CH_2OMe$ |
| 2-52 | OMe | $CF_3$ | $CH_2Cl$ |
| 2-53 | OMe | $CF_3$ | (1-Me)-c-Pr |
| 2-54 | OMe | $CF_3$ | (2-Me)-c-Pr |
| 2-55 | OMe | $CHF_2$ | Me |
| 2-56 | OMe | $CHF_2$ | Et |
| 2-57 | OMe | $CHF_2$ | c-Pr |
| 2-58 | SMe | $CF_3$ | Me |
| 2-59 | SMe | $CF_3$ | Et |
| 2-60 | SMe | $CF_3$ | c-Pr |
| 2-61 | SMe | $CF_3$ | $CH_2OMe$ |
| 2-62 | SMe | $CF_3$ | $CH_2Cl$ |
| 2-63 | SMe | $CF_3$ | (1-Me)-c-Pr |
| 2-64 | SMe | $CF_3$ | (2-Me)-c-Pr |
| 2-65 | SMe | $CHF_2$ | Me |
| 2-66 | SMe | $CHF_2$ | Et |

TABLE 2-continued

Compounds of the formula (I) according to the invention in which $R^x$ represents an ethyl group and the other substituents have the meanings listed below.

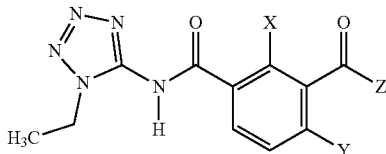

| No. | X | Y | Z |
|---|---|---|---|
| 2-67 | SMe | CHF$_2$ | c-Pr |
| 2-68 | SMe | CHF$_2$ | CH$_2$OMe |
| 2-69 | SMe | CHF$_2$ | CH$_2$Cl |
| 2-70 | SMe | CHF$_2$ | (1-Me)-c-Pr |
| 2-71 | SMe | CHF$_2$ | (2-Me)-c-Pr |
| 2-72 | SMe | SO$_2$Me | Me |
| 2-73 | SMe | SO$_2$Me | Et |
| 2-74 | SMe | SO$_2$Me | c-Pr |
| 2-75 | SMe | SO$_2$Me | CH$_2$OMe |
| 2-76 | SMe | SO$_2$Me | CH$_2$Cl |
| 2-77 | SMe | SO$_2$Me | (1-Me)-c-Pr |
| 2-78 | SMe | SO$_2$Me | (2-Me)-c-Pr |
| 2-79 | SEt | CF$_3$ | Me |
| 2-80 | SEt | CF$_3$ | Et |
| 2-81 | SEt | CF$_3$ | c-Pr |
| 2-82 | SEt | CF$_3$ | CH$_2$OMe |
| 2-83 | SEt | CF$_3$ | CH$_2$Cl |
| 2-84 | SEt | CF$_3$ | (1-Me)-c-Pr |
| 2-85 | SEt | CF$_3$ | (2-Me)-c-Pr |
| 2-86 | SEt | CHF$_2$ | Me |
| 2-87 | SEt | CHF$_2$ | Et |
| 2-88 | SEt | CHF$_2$ | c-Pr |
| 2-89 | SEt | CHF$_2$ | CH$_2$OMe |
| 2-90 | SEt | CHF$_2$ | CH$_2$Cl |
| 2-91 | SEt | CHF$_2$ | (1-Me)-c-Pr |
| 2-92 | SEt | CHF$_2$ | (2-Me)-c-Pr |
| 2-93 | SOMe | CF$_3$ | Me |
| 2-94 | SOMe | CF$_3$ | Et |
| 2-95 | SOMe | CF$_3$ | c-Pr |
| 2-96 | SOMe | CHF$_2$ | Me |
| 2-97 | SOMe | CHF$_2$ | Et |
| 2-98 | SOMe | CHF$_2$ | c-Pr |
| 2-99 | SO$_2$Me | CF$_3$ | Me |
| 2-100 | SO$_2$Me | CF$_3$ | Et |
| 2-101 | SO$_2$Me | CF$_3$ | c-Pr |
| 2-102 | SO$_2$Me | CHF$_2$ | Me |
| 2-103 | SO$_2$Me | CHF$_2$ | Et |
| 2-104 | SO$_2$Me | CHF$_2$ | c-Pr |
| 2-105 | SO$_2$Et | CF$_3$ | Me |
| 2-106 | SO$_2$Et | CF$_3$ | Et |
| 2-107 | SO$_2$Et | CF$_3$ | c-Pr |
| 2-108 | F | CF$_3$ | Me |
| 2-109 | F | CF$_3$ | Et |
| 2-110 | F | CF$_3$ | c-Pr |
| 2-111 | F | CHF$_2$ | Me |
| 2-112 | F | CHF$_2$ | Et |
| 2-113 | F | CHF$_2$ | c-Pr |
| 2-114 | Cl | Cl | Me |
| 2-115 | Cl | Cl | Et |
| 2-116 | Cl | Cl | c-Pr |
| 2-117 | Cl | Cl | CH$_2$OMe |
| 2-118 | Cl | Cl | CH$_2$Cl |
| 2-119 | Cl | Cl | (1-Me)-c-Pr |
| 2-120 | Cl | Cl | (2-Me)-c-Pr |
| 2-121 | Cl | SMe | Me |
| 2-122 | Cl | SMe | Et |
| 2-123 | Cl | SMe | c-Pr |
| 2-124 | Cl | SOMe | Me |
| 2-125 | Cl | SOMe | Et |
| 2-126 | Cl | SOMe | c-Pr |
| 2-127 | Cl | SO$_2$Me | Me |
| 2-128 | Cl | SO$_2$Me | Et |
| 2-129 | Cl | SO$_2$Me | c-Pr |
| 2-130 | Cl | SO$_2$Me | CH$_2$OMe |
| 2-131 | Cl | SO$_2$Me | CH$_2$Cl |
| 2-132 | Cl | SO$_2$Me | (1-Me)-c-Pr |

TABLE 2-continued

Compounds of the formula (I) according to the invention in which $R^x$ represents an ethyl group and the other substituents have the meanings listed below.

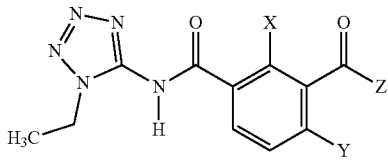

| No. | X | Y | Z |
|---|---|---|---|
| 2-133 | Cl | SO$_2$Me | (2-Me)-c-Pr |
| 2-134 | Cl | Me | Me |
| 2-135 | Cl | Me | Et |
| 2-136 | Cl | Me | c-Pr |
| 2-137 | Cl | CF$_3$ | Me |
| 2-138 | Cl | CF$_3$ | Et |
| 2-139 | Cl | CF$_3$ | n-Pr |
| 2-140 | Cl | CF$_3$ | i-Pr |
| 2-141 | Cl | CF$_3$ | c-Pr |
| 2-142 | Cl | CF$_3$ | n-Bu |
| 2-143 | Cl | CF$_3$ | t-Bu |
| 2-144 | Cl | CF$_3$ | CH$_2$OMe |
| 2-145 | Cl | CF$_3$ | CH$_2$Cl |
| 2-146 | Cl | CF$_3$ | Ac |
| 2-147 | Cl | CF$_3$ | (1-Me)-c-Pr |
| 2-148 | Cl | CF$_3$ | (2-Me)-c-Pr |
| 2-149 | Cl | CF$_3$ | (2,2-Me$_2$)-c-Pr |
| 2-150 | Cl | CF$_3$ | (1,2-Me$_2$)-c-Pr |
| 2-151 | Cl | CF$_3$ | (2-F)-c-Pr |
| 2-152 | Cl | CF$_3$ | (2,2-F$_2$)-c-Pr |
| 2-153 | Cl | CF$_3$ | c-Bu |
| 2-154 | Cl | CF$_3$ | c-pentyl |
| 2-155 | Cl | CF$_3$ | c-hexyl |
| 2-156 | Cl | CF$_3$ | 2-thienyl |
| 2-157 | Cl | CF$_3$ | 2-furyl |
| 2-158 | Cl | CF$_3$ | Ph |
| 2-159 | Cl | CF$_3$ | (4-MeO)-Ph |
| 2-160 | Cl | CF$_3$ | (4-Cl)-Ph |
| 2-161 | Cl | CF$_3$ | (3-CF$_3$)-Ph |
| 2-162 | Cl | CF$_3$ | CF$_3$ |
| 2-163 | Cl | CF$_3$ | CHF$_2$ |
| 2-164 | Cl | CHF$_2$ | Me |
| 2-165 | Cl | CHF$_2$ | Et |
| 2-166 | Cl | CHF$_2$ | n-Pr |
| 2-167 | Cl | CHF$_2$ | i-Pr |
| 2-168 | Cl | CHF$_2$ | c-Pr |
| 2-169 | Cl | CHF$_2$ | n-Bu |
| 2-171 | Cl | CHF$_2$ | t-Bu |
| 2-172 | Cl | CHF$_2$ | CH$_2$OMe |
| 2-173 | Cl | CHF$_2$ | CH$_2$Cl |
| 2-174 | Cl | CHF$_2$ | Ac |
| 2-175 | Cl | CHF$_2$ | (1-Me)-c-Pr |
| 2-176 | Cl | CHF$_2$ | (2-Me)-c-Pr |
| 2-177 | Cl | CHF$_2$ | (2,2-Me$_2$)-c-Pr |
| 2-178 | Cl | CHF$_2$ | (1,2-Me$_2$)-c-Pr |
| 2-179 | Cl | CHF$_2$ | (2-F)-c-Pr |
| 2-180 | Cl | CHF$_2$ | (2,2-F$_2$)-c-Pr |
| 2-181 | Cl | CHF$_2$ | c-Bu |
| 2-182 | Cl | CHF$_2$ | c-pentyl |
| 2-183 | Cl | CHF$_2$ | c-hexyl |
| 2-184 | Cl | CHF$_2$ | 2-thienyl |
| 2-185 | Cl | CHF$_2$ | 2-furyl |
| 2-186 | Cl | CHF$_2$ | Ph |
| 2-187 | Cl | CHF$_2$ | (4-MeO)-Ph |
| 2-188 | Cl | CHF$_2$ | (4-Cl)-Ph |
| 2-189 | Cl | CHF$_2$ | (3-CF$_3$)-Ph |
| 2-190 | Cl | CHF$_2$ | CF$_3$ |
| 2-191 | Cl | CHF$_2$ | CHF$_2$ |
| 2-192 | Cl | I | Me |
| 2-193 | Cl | I | Et |
| 2-194 | Cl | I | c-Pr |
| 2-195 | Br | CF$_3$ | Me |
| 2-196 | Br | CF$_3$ | Et |
| 2-197 | Br | CF$_3$ | c-Pr |
| 2-198 | Br | CF$_3$ | CH$_2$OMe |
| 2-199 | Br | CF$_3$ | CH$_2$Cl |

TABLE 2-continued

Compounds of the formula (I) according to the invention in which $R^x$ represents an ethyl group and the other substituents have the meanings listed below.

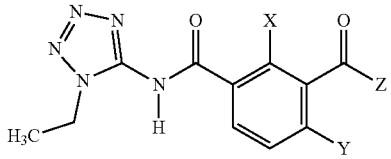

| No. | X | Y | Z |
|---|---|---|---|
| 2-200 | Br | CF$_3$ | (1-Me)-c-Pr |
| 2-201 | Br | CF$_3$ | (2-Me)-c-Pr |
| 2-202 | Br | CHF$_2$ | Me |
| 2-203 | Br | CHF$_2$ | Et |
| 2-204 | Br | CHF$_2$ | c-Pr |
| 2-205 | Br | CHF$_2$ | CH$_2$OMe |
| 2-206 | Br | CHF$_2$ | CH$_2$Cl |
| 2-207 | Br | CHF$_2$ | (1-Me)-c-Pr |
| 2-208 | Br | CHF$_2$ | (2-Me)-c-Pr |
| 2-209 | Br | SO$_2$Me | Me |
| 2-210 | Br | SO$_2$Me | Et |
| 2-211 | Br | SO$_2$Me | c-Pr |
| 2-212 | Br | SO$_2$Me | CH$_2$OMe |
| 2-213 | Br | SO$_2$Me | CH$_2$Cl |
| 2-214 | Br | SO$_2$Me | (1-Me)-c-Pr |
| 2-215 | Br | SO$_2$Me | (2-Me)-c-Pr |
| 2-216 | CH$_2$OMe | CF$_3$ | Me |
| 2-217 | CH$_2$OMe | CF$_3$ | Et |
| 2-218 | CH$_2$OMe | CF$_3$ | c-Pr |
| 2-219 | CH$_2$OMe | SO$_2$Me | Me |
| 2-220 | CH$_2$OMe | SO$_2$Me | Et |
| 2-221 | CH$_2$OMe | SO$_2$Me | c-Pr |
| 2-222 | Et | CF$_3$ | Me |
| 2-223 | Et | CF$_3$ | Et |
| 2-224 | Et | CF$_3$ | c-Pr |
| 2-225 | Et | CHF$_2$ | Me |
| 2-226 | Et | CHF$_2$ | Et |
| 2-227 | Et | CHF$_2$ | c-Pr |
| 2-228 | Et | SO$_2$Me | Me |
| 2-229 | Et | SO$_2$Me | Et |
| 2-230 | Et | SO$_2$Me | c-Pr |
| 2-231 | c-Pr | CF$_3$ | Me |
| 2-232 | c-Pr | CF$_3$ | Et |
| 2-233 | c-Pr | CF$_3$ | c-Pr |
| 2-234 | c-Pr | CF$_3$ | CH$_2$OMe |
| 2-235 | c-Pr | CF$_3$ | CH$_2$Cl |
| 2-236 | c-Pr | CF$_3$ | (1-Me)-c-Pr |
| 2-237 | c-Pr | CF$_3$ | (2-Me)-c-Pr |
| 2-238 | c-Pr | CHF$_2$ | Me |
| 2-239 | c-Pr | CHF$_2$ | Et |
| 2-240 | c-Pr | CHF$_2$ | c-Pr |
| 2-241 | c-Pr | CHF$_2$ | CH$_2$OMe |
| 2-242 | c-Pr | CHF$_2$ | CH$_2$Cl |
| 2-243 | c-Pr | CHF$_2$ | (1-Me)-c-Pr |
| 2-244 | c-Pr | CHF$_2$ | (2-Me)-c-Pr |
| 2-245 | c-Pr | SO$_2$Me | Me |
| 2-246 | c-Pr | SO$_2$Me | Et |
| 2-247 | c-Pr | SO$_2$Me | c-Pr |
| 2-248 | c-Pr | SO$_2$Me | CH$_2$OMe |
| 2-249 | c-Pr | SO$_2$Me | CH$_2$Cl |
| 2-250 | c-Pr | SO$_2$Me | (1-Me)-c-Pr |
| 2-251 | c-Pr | SO$_2$Me | (2-Me)-c-Pr |
| 2-252 | I | CF$_3$ | Me |
| 2-253 | I | CF$_3$ | Et |
| 2-254 | I | CF$_3$ | c-Pr |
| 2-255 | I | CF$_3$ | CH$_2$OMe |
| 2-256 | I | CF$_3$ | CH$_2$Cl |
| 2-257 | I | CF$_3$ | (1-Me)-c-Pr |
| 2-258 | I | CF$_3$ | (2-Me)-c-Pr |
| 2-259 | I | CHF$_2$ | Me |
| 2-260 | I | CHF$_2$ | Et |
| 2-261 | I | CHF$_2$ | c-Pr |
| 2-262 | I | CHF$_2$ | CH$_2$OMe |
| 2-263 | I | CHF$_2$ | CH$_2$Cl |
| 2-264 | I | CHF$_2$ | (1-Me)-c-Pr |
| 2-265 | I | CHF$_2$ | (2-Me)-c-Pr |

TABLE 2-continued

Compounds of the formula (I) according to the invention in which R^x represents an ethyl group and the other substituents have the meanings listed below.

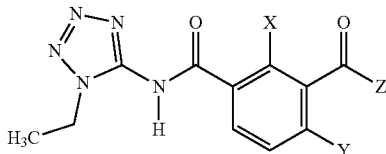

| No. | X | Y | Z |
| --- | --- | --- | --- |
| 2-266 | I | SO$_2$Me | Me |
| 2-267 | I | SO$_2$Me | Et |
| 2-268 | I | SO$_2$Me | c-Pr |
| 2-269 | I | SO$_2$Me | CH$_2$OMe |
| 2-270 | I | SO$_2$Me | CH$_2$Cl |
| 2-271 | I | SO$_2$Me | (1-Me)-c-Pr |
| 2-272 | I | SO$_2$Me | (2-Me)-c-Pr |
| 2-273 | CF$_3$ | CF$_3$ | Me |
| 2-274 | CF$_3$ | CF$_3$ | Et |
| 2-275 | CF$_3$ | CF$_3$ | c-Pr |
| 2-276 | CF$_3$ | CF$_3$ | CH$_2$OMe |
| 2-277 | CF$_3$ | CF$_3$ | CH$_2$Cl |
| 2-278 | CF$_3$ | CF$_3$ | (1-Me)-c-Pr |
| 2-279 | CF$_3$ | CF$_3$ | (2-Me)-c-Pr |
| 2-280 | Cl | Cl | i-Pr |
| 2-281 | Cl | Cl | c-pentyl |
| 2-282 | Cl | Cl | 2-thienyl |
| 2-283 | Cl | Cl | (4-MeO)-Ph |
| 2-284 | SMe | CF$_3$ | c-Bu |
| 2-285 | SMe | CF$_3$ | c-Hexyl |
| 2-286 | Cl | CF$_3$ | (3,5-F$_2$)-Ph |
| 2-287 | SMe | CF$_3$ | (3,5-F$_2$)-Ph |
| 2-288 | Cl | Br | Me |
| 2-289 | Cl | Br | Et |
| 2-290 | Cl | Br | c-Pr |
| 2-291 | Me | Cl | Me |
| 2-292 | Me | Cl | Et |
| 2-293 | Me | Cl | c-Pr |
| 2-294 | Cl | CF$_3$ | vinyl |

TABLE 3

Compounds of the formula (I) according to the invention in which R^x represents a propyl group and the other substituents have the meanings listed below.

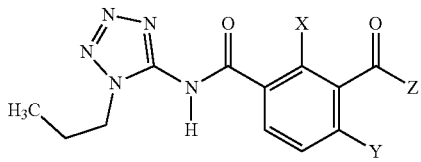

| No. | X | Y | Z |
| --- | --- | --- | --- |
| 3-1 | Me | Me | Me |
| 3-2 | Me | Me | Et |
| 3-3 | Me | Me | c-Pr |
| 3-4 | Me | SMe | Me |
| 3-5 | Me | SMe | Et |
| 3-6 | Me | SMe | c-Pr |
| 3-7 | Me | SO$_2$Me | Me |
| 3-8 | Me | SO$_2$Me | Et |
| 3-9 | Me | SO$_2$Me | c-Pr |
| 3-10 | Me | SO$_2$Me | CH$_2$OMe |
| 3-11 | Me | SO$_2$Me | CH$_2$Cl |
| 3-12 | Me | SO$_2$Me | (1-Me)-c-Pr |
| 3-13 | Me | SO$_2$Me | (2-Me)-c-Pr |
| 3-14 | Me | CF$_3$ | Me |
| 3-15 | Me | CF$_3$ | Et |
| 3-16 | Me | CF$_3$ | n-Pr |
| 3-17 | Me | CF$_3$ | i-Pr |
| 3-18 | Me | CF$_3$ | c-Pr |
| 3-19 | Me | CF$_3$ | n-Bu |

TABLE 3-continued

Compounds of the formula (I) according to the invention in which R^x represents a propyl group and the other substituents have the meanings listed below.

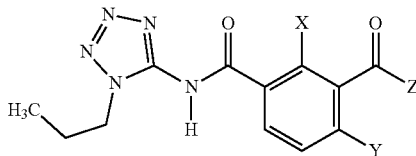

| No. | X | Y | Z |
|---|---|---|---|
| 3-20 | Me | CF₃ | t-Bu |
| 3-21 | Me | CF₃ | CH₂OMe |
| 3-22 | Me | CF₃ | CH₂Cl |
| 3-23 | Me | CF₃ | Ac |
| 3-24 | Me | CF₃ | (1-Me)-c-Pr |
| 3-25 | Me | CF₃ | (2-Me)-c-Pr |
| 3-26 | Me | CF₃ | (2,2-Me₂)-c-Pr |
| 3-27 | Me | CF₃ | (1,2-Me₂)-c-Pr |
| 3-28 | Me | CF₃ | (2-F)-c-Pr |
| 3-29 | Me | CF₃ | (2,2-F₂)-c-Pr |
| 3-30 | Me | CF₃ | c-Bu |
| 3-31 | Me | CF₃ | c-pentyl |
| 3-32 | Me | CF₃ | c-hexyl |
| 3-33 | Me | CF₃ | 2-thienyl |
| 3-34 | Me | CF₃ | 2-furyl |
| 3-35 | Me | CF₃ | Ph |
| 3-36 | Me | CF₃ | (4-MeO)-Ph |
| 3-37 | Me | CF₃ | (4-Cl)-Ph |
| 3-38 | Me | CF₃ | (3-CF₃)-Ph |
| 3-39 | Me | CF₃ | CF₃ |
| 3-40 | Me | CF₃ | CHF₂ |
| 3-41 | Me | CHF₂ | Me |
| 3-42 | Me | CHF₂ | Et |
| 3-43 | Me | CHF₂ | c-Pr |
| 3-44 | Me | CHF₂ | CH₂OMe |
| 3-45 | Me | CHF₂ | CH₂Cl |
| 3-46 | Me | CHF₂ | (1-Me)-c-Pr |
| 3-47 | Me | CHF₂ | (2-Me)-c-Pr |
| 3-48 | OMe | CF₃ | Me |
| 3-49 | OMe | CF₃ | Et |
| 3-50 | OMe | CF₃ | c-Pr |
| 3-51 | OMe | CF₃ | CH₂OMe |
| 3-52 | OMe | CF₃ | CH₂Cl |
| 3-53 | OMe | CF₃ | (1-Me)-c-Pr |
| 3-54 | OMe | CF₃ | (2-Me)-c-Pr |
| 3-55 | OMe | CHF₂ | Me |
| 3-56 | OMe | CHF₂ | Et |
| 3-57 | OMe | CHF₂ | c-Pr |
| 3-58 | SMe | CF₃ | Me |
| 3-59 | SMe | CF₃ | Et |
| 3-60 | SMe | CF₃ | c-Pr |
| 3-61 | SMe | CF₃ | CH₂OMe |
| 3-62 | SMe | CF₃ | CH₂Cl |
| 3-63 | SMe | CF₃ | (1-Me)-c-Pr |
| 3-64 | SMe | CF₃ | (2-Me)-c-Pr |
| 3-65 | SMe | CHF₂ | Me |
| 3-66 | SMe | CHF₂ | Et |
| 3-67 | SMe | CHF₂ | c-Pr |
| 3-68 | SMe | CHF₂ | CH₂OMe |
| 3-69 | SMe | CHF₂ | CH₂Cl |
| 3-70 | SMe | CHF₂ | (1-Me)-c-Pr |
| 3-71 | SMe | CHF₂ | (2-Me)-c-Pr |
| 3-72 | SMe | SO₂Me | Me |
| 3-73 | SMe | SO₂Me | Et |
| 3-74 | SMe | SO₂Me | c-Pr |
| 3-75 | SMe | SO₂Me | CH₂OMe |
| 3-76 | SMe | SO₂Me | CH₂Cl |
| 3-77 | SMe | SO₂Me | (1-Me)-c-Pr |
| 3-78 | SMe | SO₂Me | (2-Me)-c-Pr |
| 3-79 | SEt | CF₃ | Me |
| 3-80 | SEt | CF₃ | Et |
| 3-81 | SEt | CF₃ | c-Pr |
| 3-82 | SEt | CF₃ | CH₂OMe |
| 3-83 | SEt | CF₃ | CH₂Cl |
| 3-84 | SEt | CF₃ | (1-Me)-c-Pr |
| 3-85 | SEt | CF₃ | (2-Me)-c-Pr |

TABLE 3-continued

Compounds of the formula (I) according to the invention in which $R^x$ represents a propyl group and the other substituents have the meanings listed below.

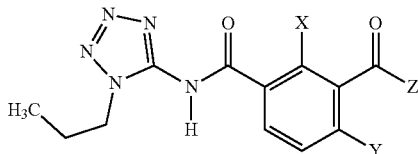

| No. | X | Y | Z |
|---|---|---|---|
| 3-86 | SEt | CHF$_2$ | Me |
| 3-87 | SEt | CHF$_2$ | Et |
| 3-88 | SEt | CHF$_2$ | c-Pr |
| 3-89 | SEt | CHF$_2$ | CH$_2$OMe |
| 3-90 | SEt | CHF$_2$ | CH$_2$Cl |
| 3-91 | SEt | CHF$_2$ | (1-Me)-c-Pr |
| 3-92 | SEt | CHF$_2$ | (2-Me)-c-Pr |
| 3-93 | SOMe | CF$_3$ | Me |
| 3-94 | SOMe | CF$_3$ | Et |
| 3-95 | SOMe | CF$_3$ | c-Pr |
| 3-96 | SOMe | CHF$_2$ | Me |
| 3-97 | SOMe | CHF$_2$ | Et |
| 3-98 | SOMe | CHF$_2$ | c-Pr |
| 3-99 | SO$_2$Me | CF$_3$ | Me |
| 3-100 | SO$_2$Me | CF$_3$ | Et |
| 3-101 | SO$_2$Me | CF$_3$ | c-Pr |
| 3-102 | SO$_2$Me | CHF$_2$ | Me |
| 3-103 | SO$_2$Me | CHF$_2$ | Et |
| 3-104 | SO$_2$Me | CHF$_2$ | c-Pr |
| 3-105 | SO$_2$Et | CF$_3$ | Me |
| 3-106 | SO$_2$Et | CF$_3$ | Et |
| 3-107 | SO$_2$Et | CF$_3$ | c-Pr |
| 3-108 | F | CF$_3$ | Me |
| 3-109 | F | CF$_3$ | Et |
| 3-110 | F | CF$_3$ | c-Pr |
| 3-111 | F | CHF$_2$ | Me |
| 3-112 | F | CHF$_2$ | Et |
| 3-113 | F | CHF$_2$ | c-Pr |
| 3-114 | Cl | Cl | Me |
| 3-115 | Cl | Cl | Et |
| 3-116 | Cl | Cl | c-Pr |
| 3-117 | Cl | Cl | CH$_2$OMe |
| 3-118 | Cl | Cl | CH$_2$Cl |
| 3-119 | Cl | Cl | (1-Me)-c-Pr |
| 3-120 | Cl | Cl | (2-Me)-c-Pr |
| 3-121 | Cl | SMe | Me |
| 3-122 | Cl | SMe | Et |
| 3-123 | Cl | SMe | c-Pr |
| 3-124 | Cl | SOMe | Me |
| 3-125 | Cl | SOMe | Et |
| 3-126 | Cl | SOMe | c-Pr |
| 3-127 | Cl | SO$_2$Me | Me |
| 3-128 | Cl | SO$_2$Me | Et |
| 3-129 | Cl | SO$_2$Me | c-Pr |
| 3-130 | Cl | SO$_2$Me | CH$_2$OMe |
| 3-131 | Cl | SO$_2$Me | CH$_2$Cl |
| 3-132 | Cl | SO$_2$Me | (1-Me)-c-Pr |
| 3-133 | Cl | SO$_2$Me | (2-Me)-c-Pr |
| 3-134 | Cl | Me | Me |
| 3-135 | Cl | Me | Et |
| 3-136 | Cl | Me | c-Pr |
| 3-137 | Cl | CF$_3$ | Me |
| 3-138 | Cl | CF$_3$ | Et |
| 3-139 | Cl | CF$_3$ | n-Pr |
| 3-140 | Cl | CF$_3$ | i-Pr |
| 3-141 | Cl | CF$_3$ | c-Pr |
| 3-142 | Cl | CF$_3$ | n-Bu |
| 3-143 | Cl | CF$_3$ | t-Bu |
| 3-144 | Cl | CF$_3$ | CH$_2$OMe |
| 3-145 | Cl | CF$_3$ | CH$_2$Cl |
| 3-146 | Cl | CF$_3$ | Ac |
| 3-147 | Cl | CF$_3$ | (1-Me)-c-Pr |
| 3-148 | Cl | CF$_3$ | (2-Me)-c-Pr |
| 3-149 | Cl | CF$_3$ | (2,2-Me$_2$)-c-Pr |
| 3-150 | Cl | CF$_3$ | (1,2-Me$_2$)-c-Pr |
| 3-151 | Cl | CF$_3$ | (2-F)-c-Pr |

TABLE 3-continued

Compounds of the formula (I) according to the invention in which $R^x$ represents a propyl group and the other substituents have the meanings listed below.

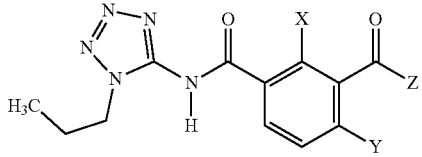

| No. | X | Y | Z |
| --- | --- | --- | --- |
| 3-152 | Cl | CF$_3$ | (2,2-F$_2$)-c-Pr |
| 3-153 | Cl | CF$_3$ | c-Bu |
| 3-154 | Cl | CF$_3$ | c-pentyl |
| 3-155 | Cl | CF$_3$ | c-hexyl |
| 3-156 | Cl | CF$_3$ | 2-thienyl |
| 3-157 | Cl | CF$_3$ | 2-furyl |
| 3-158 | Cl | CF$_3$ | Ph |
| 3-159 | Cl | CF$_3$ | (4-MeO)-Ph |
| 3-160 | Cl | CF$_3$ | (4-Cl)-Ph |
| 3-161 | Cl | CF$_3$ | (3-CF$_3$)-Ph |
| 3-162 | Cl | CF$_3$ | CF$_3$ |
| 3-163 | Cl | CF$_3$ | CHF$_2$ |
| 3-164 | Cl | CHF$_2$ | Me |
| 3-165 | Cl | CHF$_2$ | Et |
| 3-166 | Cl | CHF$_2$ | n-Pr |
| 3-167 | Cl | CHF$_2$ | i-Pr |
| 3-168 | Cl | CHF$_2$ | c-Pr |
| 3-169 | Cl | CHF$_2$ | n-Bu |
| 3-171 | Cl | CHF$_2$ | t-Bu |
| 3-172 | Cl | CHF$_2$ | CH$_2$OMe |
| 3-173 | Cl | CHF$_2$ | CH$_2$Cl |
| 3-174 | Cl | CHF$_2$ | Ac |
| 3-175 | Cl | CHF$_2$ | (1-Me)-c-Pr |
| 3-176 | Cl | CHF$_2$ | (2-Me)-c-Pr |
| 3-177 | Cl | CHF$_2$ | (2,2-Me$_2$)-c-Pr |
| 3-178 | Cl | CHF$_2$ | (1,2-Me$_2$)-c-Pr |
| 3-179 | Cl | CHF$_2$ | (2-F)-c-Pr |
| 3-180 | Cl | CHF$_2$ | (2,2-F$_2$)-c-Pr |
| 3-181 | Cl | CHF$_2$ | c-Bu |
| 3-182 | Cl | CHF$_2$ | c-pentyl |
| 3-183 | Cl | CHF$_2$ | c-hexyl |
| 3-184 | Cl | CHF$_2$ | 2-thienyl |
| 3-185 | Cl | CHF$_2$ | 2-furyl |
| 3-186 | Cl | CHF$_2$ | Ph |
| 3-187 | Cl | CHF$_2$ | (4-MeO)-Ph |
| 3-188 | Cl | CHF$_2$ | (4-Cl)-Ph |
| 3-189 | Cl | CHF$_2$ | (3-CF$_3$)-Ph |
| 3-190 | Cl | CHF$_2$ | CF$_3$ |
| 3-191 | Cl | CHF$_2$ | CHF$_2$ |
| 3-192 | Cl | I | Me |
| 3-193 | Cl | I | Et |
| 3-194 | Cl | I | c-Pr |
| 3-195 | Br | CF$_3$ | Me |
| 3-196 | Br | CF$_3$ | Et |
| 3-197 | Br | CF$_3$ | c-Pr |
| 3-198 | Br | CF$_3$ | CH$_2$OMe |
| 3-199 | Br | CF$_3$ | CH$_2$Cl |
| 3-200 | Br | CF$_3$ | (1-Me)-c-Pr |
| 3-201 | Br | CF$_3$ | (2-Me)-c-Pr |
| 3-202 | Br | CHF$_2$ | Me |
| 3-203 | Br | CHF$_2$ | Et |
| 3-204 | Br | CHF$_2$ | c-Pr |
| 3-205 | Br | CHF$_2$ | CH$_2$OMe |
| 3-206 | Br | CHF$_2$ | CH$_2$Cl |
| 3-207 | Br | CHF$_2$ | (1-Me)-c-Pr |
| 3-208 | Br | CHF$_2$ | (2-Me)-c-Pr |
| 3-209 | Br | SO$_2$Me | Me |
| 3-210 | Br | SO$_2$Me | Et |
| 3-211 | Br | SO$_2$Me | c-Pr |
| 3-212 | Br | SO$_2$Me | CH$_2$OMe |
| 3-213 | Br | SO$_2$Me | CH$_2$Cl |
| 3-214 | Br | SO$_2$Me | (1-Me)-c-Pr |
| 3-215 | Br | SO$_2$Me | (2-Me)-c-Pr |
| 3-216 | CH$_2$OMe | CF$_3$ | Me |
| 3-217 | CH$_2$OMe | CF$_3$ | Et |
| 3-218 | CH$_2$OMe | CF$_3$ | c-Pr |

TABLE 3-continued

Compounds of the formula (I) according to the invention in which $R^x$ represents a propyl group and the other substituents have the meanings listed below.

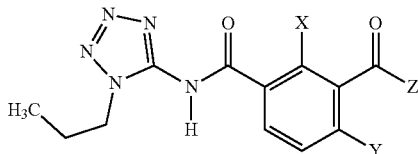

| No. | X | Y | Z |
|---|---|---|---|
| 3-219 | CH$_2$OMe | SO$_2$Me | Me |
| 3-220 | CH$_2$OMe | SO$_2$Me | Et |
| 3-221 | CH$_2$OMe | SO$_2$Me | c-Pr |
| 3-222 | Et | CF$_3$ | Me |
| 3-223 | Et | CF$_3$ | Et |
| 3-224 | Et | CF$_3$ | c-Pr |
| 3-225 | Et | CHF$_2$ | Me |
| 3-226 | Et | CHF$_2$ | Et |
| 3-227 | Et | CHF$_2$ | c-Pr |
| 3-228 | Et | SO$_2$Me | Me |
| 3-229 | Et | SO$_2$Me | Et |
| 3-230 | Et | SO$_2$Me | c-Pr |
| 3-231 | c-Pr | CF$_3$ | Me |
| 3-232 | c-Pr | CF$_3$ | Et |
| 3-233 | c-Pr | CF$_3$ | c-Pr |
| 3-234 | c-Pr | CF$_3$ | CH$_2$OMe |
| 3-235 | c-Pr | CF$_3$ | CH$_2$Cl |
| 3-236 | c-Pr | CF$_3$ | (1-Me)-c-Pr |
| 3-237 | c-Pr | CF$_3$ | (2-Me)-c-Pr |
| 3-238 | c-Pr | CHF$_2$ | Me |
| 3-239 | c-Pr | CHF$_2$ | Et |
| 3-240 | c-Pr | CHF$_2$ | c-Pr |
| 3-241 | c-Pr | CHF$_2$ | CH$_2$OMe |
| 3-242 | c-Pr | CHF$_2$ | CH$_2$Cl |
| 3-243 | c-Pr | CHF$_2$ | (1-Me)-c-Pr |
| 3-244 | c-Pr | CHF$_2$ | (2-Me)-c-Pr |
| 3-245 | c-Pr | SO$_2$Me | Me |
| 3-246 | c-Pr | SO$_2$Me | Et |
| 3-247 | c-Pr | SO$_2$Me | c-Pr |
| 3-248 | c-Pr | SO$_2$Me | CH$_2$OMe |
| 3-249 | c-Pr | SO$_2$Me | CH$_2$Cl |
| 3-250 | c-Pr | SO$_2$Me | (1-Me)-c-Pr |
| 3-251 | c-Pr | SO$_2$Me | (2-Me)-c-Pr |
| 3-252 | I | CF$_3$ | Me |
| 3-253 | I | CF$_3$ | Et |
| 3-254 | I | CF$_3$ | c-Pr |
| 3-255 | I | CF$_3$ | CH$_2$OMe |
| 3-256 | I | CF$_3$ | CH$_2$Cl |
| 3-257 | I | CF$_3$ | (1-Me)-c-Pr |
| 3-258 | I | CF$_3$ | (2-Me)-c-Pr |
| 3-259 | I | CHF$_2$ | Me |
| 3-260 | I | CHF$_2$ | Et |
| 3-261 | I | CHF$_2$ | c-Pr |
| 3-262 | I | CHF$_2$ | CH$_2$OMe |
| 3-263 | I | CHF$_2$ | CH$_2$Cl |
| 3-264 | I | CHF$_2$ | (1-Me)-c-Pr |
| 3-265 | I | CHF$_2$ | (2-Me)-c-Pr |
| 3-266 | I | SO$_2$Me | Me |
| 3-267 | I | SO$_2$Me | Et |
| 3-268 | I | SO$_2$Me | c-Pr |
| 3-269 | I | SO$_2$Me | CH$_2$OMe |
| 3-270 | I | SO$_2$Me | CH$_2$Cl |
| 3-271 | I | SO$_2$Me | (1-Me)-c-Pr |
| 3-272 | I | SO$_2$Me | (2-Me)-c-Pr |
| 3-273 | CF$_3$ | CF$_3$ | Me |
| 3-274 | CF$_3$ | CF$_3$ | Et |
| 3-275 | CF$_3$ | CF$_3$ | c-Pr |
| 3-276 | CF$_3$ | CF$_3$ | CH$_2$OMe |
| 3-277 | CF$_3$ | CF$_3$ | CH$_2$Cl |
| 3-278 | CF$_3$ | CF$_3$ | (1-Me)-c-Pr |
| 3-279 | CF$_3$ | CF$_3$ | (2-Me)-c-Pr |
| 3-280 | SMe | CF$_3$ | c-Bu |
| 3-281 | SMe | CF$_3$ | c-hexyl |
| 3-282 | Cl | CF$_3$ | (3,5-F$_2$)-Ph |
| 3-283 | SMe | CF$_3$ | (3,5-F$_2$)-Ph |
| 3-284 | Cl | Br | Me |

TABLE 3-continued

Compounds of the formula (I) according to the invention in which $R^x$ represents a propyl group and the other substituents have the meanings listed below.

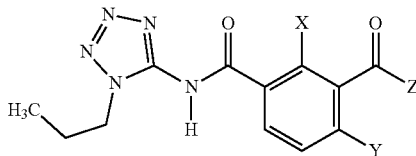

| No. | X | Y | Z |
|---|---|---|---|
| 3-285 | Cl | Br | Et |
| 3-286 | Cl | Br | c-Pr |
| 3-287 | Me | Cl | Me |
| 3-288 | Me | Cl | Et |
| 3-289 | Me | Cl | c-Pr |
| 3-290 | Cl | $CF_3$ | vinyl |

TABLE 4

Compounds of the formula (II) according to the invention in which L represents methoxy and the other substituents have the meanings listed below

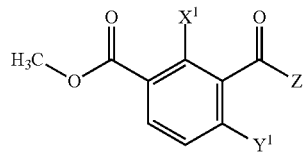

| No. | $X^1$ | $Y^1$ | Z |
|---|---|---|---|
| 4-1 | Me | $CF_3$ | Me |
| 4-2 | Me | $CF_3$ | Et |
| 4-3 | Me | $CF_3$ | n-Pr |
| 4-4 | Me | $CF_3$ | i-Pr |
| 4-5 | Me | $CF_3$ | c-Pr |
| 4-6 | Me | $CF_3$ | n-Bu |
| 4-7 | Me | $CF_3$ | t-Bu |
| 4-8 | Me | $CF_3$ | $CH_2OMe$ |
| 4-9 | Me | $CF_3$ | $CH_2Cl$ |
| 4-10 | Me | $CF_3$ | Ac |
| 4-11 | Me | $CF_3$ | (1-Me)-c-Pr |
| 4-12 | Me | $CF_3$ | (2-Me)-c-Pr |
| 4-13 | Me | $CF_3$ | $(2,2-Me_2)$-c-Pr |
| 4-14 | Me | $CF_3$ | $(1,2-Me_2)$-c-Pr |
| 4-15 | Me | $CF_3$ | (2-F)-c-Pr |
| 4-16 | Me | $CF_3$ | $(2,2-F_2)$-c-Pr |
| 4-17 | Me | $CF_3$ | c-Bu |
| 4-18 | Me | $CF_3$ | c-pentyl |
| 4-19 | Me | $CF_3$ | c-hexyl |
| 4-20 | Me | $CF_3$ | 2-thienyl |
| 4-21 | Me | $CF_3$ | 2-furyl |
| 4-22 | Me | $CF_3$ | Ph |
| 4-23 | Me | $CF_3$ | (4-MeO)-Ph |
| 4-24 | Me | $CF_3$ | (4-Cl)-Ph |
| 4-25 | Me | $CF_3$ | $(3-CF_3)$-Ph |
| 4-26 | Me | $CF_3$ | $CF_3$ |
| 4-27 | Me | $CF_3$ | $CHF_2$ |
| 4-28 | Me | $CHF_2$ | Me |
| 4-29 | Me | $CHF_2$ | Et |
| 4-30 | Me | $CHF_2$ | c-Pr |
| 4-31 | Me | $CHF_2$ | $CH_2OMe$ |
| 4-32 | Me | $CHF_2$ | $CH_2Cl$ |
| 4-33 | Me | $CHF_2$ | (1-Me)-c-Pr |
| 4-34 | Me | $CHF_2$ | (2-Me)-c-Pr |
| 4-35 | OMe | $CF_3$ | Me |
| 4-36 | OMe | $CF_3$ | Et |
| 4-37 | OMe | $CF_3$ | c-Pr |
| 4-38 | OMe | $CF_3$ | $CH_2OMe$ |
| 4-39 | OMe | $CF_3$ | $CH_2Cl$ |
| 4-40 | OMe | $CF_3$ | (1-Me)-c-Pr |
| 4-41 | OMe | $CF_3$ | (2-Me)-c-Pr |
| 4-42 | OMe | $CHF_2$ | Me |

TABLE 4-continued

Compounds of the formula (II) according to the invention in which L represents methoxy and the other substituents have the meanings listed below

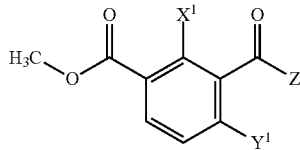

| No. | $X^1$ | $Y^1$ | Z |
|---|---|---|---|
| 4-43 | OMe | $CHF_2$ | Et |
| 4-44 | OMe | $CHF_2$ | c-Pr |
| 4-45 | SMe | $CF_3$ | Me |
| 4-46 | SMe | $CF_3$ | Et |
| 4-47 | SMe | $CF_3$ | n-Pr |
| 4-48 | SMe | $CF_3$ | i-Pr |
| 4-49 | SMe | $CF_3$ | c-Pr |
| 4-50 | SMe | $CF_3$ | n-Bu |
| 4-51 | SMe | $CF_3$ | t-Bu |
| 4-52 | SMe | $CF_3$ | $CH_2OMe$ |
| 4-53 | SMe | $CF_3$ | $CH_2Cl$ |
| 4-54 | SMe | $CF_3$ | Ac |
| 4-55 | SMe | $CF_3$ | (1-Me)-c-Pr |
| 4-56 | SMe | $CF_3$ | (2-Me)-c-Pr |
| 4-57 | SMe | $CF_3$ | $(2,2-Me_2)$-c-Pr |
| 4-58 | SMe | $CF_3$ | $(1,2-Me_2)$-c-Pr |
| 4-59 | SMe | $CF_3$ | (2-F)-c-Pr |
| 4-60 | SMe | $CF_3$ | $(2,2-F_2)$-c-Pr |
| 4-61 | SMe | $CF_3$ | c-Bu |
| 4-62 | SMe | $CF_3$ | c-pentyl |
| 4-63 | SMe | $CF_3$ | c-hexyl |
| 4-64 | SMe | $CF_3$ | 2-thienyl |
| 4-65 | SMe | $CF_3$ | 2-furyl |
| 4-66 | SMe | $CF_3$ | Ph |
| 4-67 | SMe | $CF_3$ | (4-MeO)-Ph |
| 4-68 | SMe | $CF_3$ | (4-Cl)-Ph |
| 4-69 | SMe | $CF_3$ | $(3-CF_3)$-Ph |
| 4-70 | SMe | $CF_3$ | $CF_3$ |
| 4-71 | SMe | $CF_3$ | $CHF_2$ |
| 4-72 | SMe | $CHF_2$ | Me |
| 4-73 | SMe | $CHF_2$ | Et |
| 4-74 | SMe | $CHF_2$ | c-Pr |
| 4-75 | SMe | $CHF_2$ | $CH_2OMe$ |
| 4-76 | SMe | $CHF_2$ | $CH_2Cl$ |
| 4-77 | SMe | $CHF_2$ | (1-Me)-c-Pr |
| 4-78 | SMe | $CHF_2$ | (2-Me)-c-Pr |
| 4-79 | SEt | $CF_3$ | Me |
| 4-80 | SEt | $CF_3$ | Et |
| 4-81 | SEt | $CF_3$ | c-Pr |
| 4-82 | SEt | $CF_3$ | $CH_2OMe$ |
| 4-83 | SEt | $CF_3$ | $CH_2Cl$ |
| 4-84 | SEt | $CF_3$ | (1-Me)-c-Pr |
| 4-85 | SEt | $CF_3$ | (2-Me)-c-Pr |
| 4-86 | SEt | $CHF_2$ | Me |
| 4-87 | SEt | $CHF_2$ | Et |
| 4-88 | SEt | $CHF_2$ | c-Pr |
| 4-89 | SEt | $CHF_2$ | $CH_2OMe$ |
| 4-90 | SEt | $CHF_2$ | $CH_2Cl$ |
| 4-91 | SEt | $CHF_2$ | (1-Me)-c-Pr |
| 4-92 | SEt | $CHF_2$ | (2-Me)-c-Pr |
| 4-93 | F | $CF_3$ | Me |
| 4-94 | F | $CF_3$ | Et |
| 4-95 | F | $CF_3$ | c-Pr |
| 4-96 | F | $CHF_2$ | Me |
| 4-97 | F | $CHF_2$ | Et |
| 4-98 | F | $CHF_2$ | c-Pr |
| 4-99 | Cl | $CF_3$ | Me |
| 4-100 | Cl | $CF_3$ | Et |
| 4-101 | Cl | $CF_3$ | n-Pr |
| 4-102 | Cl | $CF_3$ | i-Pr |
| 4-103 | Cl | $CF_3$ | c-Pr |
| 4-104 | Cl | $CF_3$ | n-Bu |
| 4-105 | Cl | $CF_3$ | t-Bu |
| 4-106 | Cl | $CF_3$ | $CH_2OMe$ |
| 4-107 | Cl | $CF_3$ | $CH_2Cl$ |
| 4-108 | Cl | $CF_3$ | Ac |
| 4-109 | Cl | $CF_3$ | (1-Me)-c-Pr |

TABLE 4-continued

Compounds of the formula (II) according to the invention in which L represents methoxy and the other substituents have the meanings listed below

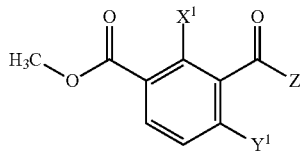

| No. | X$^1$ | Y$^1$ | Z |
|---|---|---|---|
| 4-110 | Cl | CF$_3$ | (2-Me)-c-Pr |
| 4-111 | Cl | CF$_3$ | (2,2-Me$_2$)-c-Pr |
| 4-112 | Cl | CF$_3$ | (1,2-Me$_2$)-c-Pr |
| 4-113 | Cl | CF$_3$ | (2-F)-c-Pr |
| 4-114 | Cl | CF$_3$ | (2,2-F$_2$)-c-Pr |
| 4-115 | Cl | CF$_3$ | c-Bu |
| 4-116 | Cl | CF$_3$ | c-pentyl |
| 4-117 | Cl | CF$_3$ | c-hexyl |
| 4-118 | Cl | CF$_3$ | 2-thienyl |
| 4-119 | Cl | CF$_3$ | 2-furyl |
| 4-120 | Cl | CF$_3$ | Ph |
| 4-121 | Cl | CF$_3$ | (4-MeO)-Ph |
| 4-122 | Cl | CF$_3$ | (4-Cl)-Ph |
| 4-123 | Cl | CF$_3$ | (3-CF$_3$)-Ph |
| 4-124 | Cl | CF$_3$ | CF$_3$ |
| 4-125 | Cl | CF$_3$ | CHF$_2$ |
| 4-126 | Cl | CHF$_2$ | Me |
| 4-127 | Cl | CHF$_2$ | Et |
| 4-128 | Cl | CHF$_2$ | n-Pr |
| 4-129 | Cl | CHF$_2$ | i-Pr |
| 4-130 | Cl | CHF$_2$ | c-Pr |
| 4-131 | Cl | CHF$_2$ | n-Bu |
| 4-132 | Cl | CHF$_2$ | t-Bu |
| 4-133 | Cl | CHF$_2$ | CH$_2$OMe |
| 4-134 | Cl | CHF$_2$ | CH$_2$Cl |
| 4-135 | Cl | CHF$_2$ | Ac |
| 4-136 | Cl | CHF$_2$ | (1-Me)-c-Pr |
| 4-137 | Cl | CHF$_2$ | (2-Me)-c-Pr |
| 4-138 | Cl | CHF$_2$ | (2,2-Me$_2$)-c-Pr |
| 4-139 | Cl | CHF$_2$ | (1,2-Me$_2$)-c-Pr |
| 4-140 | Cl | CHF$_2$ | (2-F)-c-Pr |
| 4-141 | Cl | CHF$_2$ | (2,2-F$_2$)-c-Pr |
| 4-142 | Cl | CHF$_2$ | c-Bu |
| 4-143 | Cl | CHF$_2$ | c-pentyl |
| 4-144 | Cl | CHF$_2$ | c-hexyl |
| 4-145 | Cl | CHF$_2$ | 2-thienyl |
| 4-146 | Cl | CHF$_2$ | 2-furyl |
| 4-147 | Cl | CHF$_2$ | Ph |
| 4-148 | Cl | CHF$_2$ | (4-MeO)-Ph |
| 4-149 | Cl | CHF$_2$ | (4-Cl)-Ph |
| 4-150 | Cl | CHF$_2$ | (3-CF$_3$)-Ph |
| 4-151 | Cl | CHF$_2$ | CF$_3$ |
| 4-152 | Cl | CHF$_2$ | CHF$_2$ |
| 4-153 | Br | CF$_3$ | Me |
| 4-154 | Br | CF$_3$ | Et |
| 4-155 | Br | CF$_3$ | c-Pr |
| 4-156 | Br | CF$_3$ | CH$_2$OMe |
| 4-157 | Br | CF$_3$ | CH$_2$Cl |
| 4-158 | Br | CF$_3$ | (1-Me)-c-Pr |
| 4-159 | Br | CF$_3$ | (2-Me)-c-Pr |
| 4-160 | Br | CHF$_2$ | Me |
| 4-161 | Br | CHF$_2$ | Et |
| 4-162 | Br | CHF$_2$ | c-Pr |
| 4-163 | Br | CHF$_2$ | CH$_2$OMe |
| 4-164 | Br | CHF$_2$ | CH$_2$Cl |
| 4-165 | Br | CHF$_2$ | (1-Me)-c-Pr |
| 4-166 | Br | CHF$_2$ | (2-Me)-c-Pr |
| 4-167 | I | CF$_3$ | Me |
| 4-168 | I | CF$_3$ | Et |
| 4-169 | I | CF$_3$ | c-Pr |
| 4-170 | I | CF$_3$ | CH$_2$OMe |
| 4-171 | I | CF$_3$ | CH$_2$Cl |
| 4-172 | I | CF$_3$ | (1-Me)-c-Pr |
| 4-173 | I | CF$_3$ | (2-Me)-c-Pr |
| 4-174 | I | CHF$_2$ | Me |
| 4-175 | I | CHF$_2$ | Et |
| 4-176 | I | CHF$_2$ | c-Pr |

TABLE 4-continued

Compounds of the formula (II) according to the invention in which L represents methoxy and the other substituents have the meanings listed below

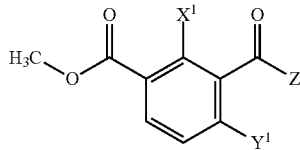

| No. | $X^1$ | $Y^1$ | Z |
|---|---|---|---|
| 4-177 | I | $CHF_2$ | $CH_2OMe$ |
| 4-178 | I | $CHF_2$ | $CH_2Cl$ |
| 4-179 | I | $CHF_2$ | (1-Me)-c-Pr |
| 4-180 | I | $CHF_2$ | (2-Me)-c-Pr |
| 4-181 | Et | $CF_3$ | Me |
| 4-182 | Et | $CF_3$ | Et |
| 4-183 | Et | $CF_3$ | c-Pr |
| 4-184 | Et | $CHF_2$ | Me |
| 4-185 | Et | $CHF_2$ | Et |
| 4-186 | Et | $CHF_2$ | c-Pr |
| 4-187 | c-Pr | $CF_3$ | Me |
| 4-188 | c-Pr | $CF_3$ | Et |
| 4-189 | c-Pr | $CF_3$ | c-Pr |
| 4-190 | c-Pr | $CF_3$ | $CH_2OMe$ |
| 4-191 | c-Pr | $CF_3$ | $CH_2Cl$ |
| 4-192 | c-Pr | $CF_3$ | (1-Me)-c-Pr |
| 4-193 | c-Pr | $CF_3$ | (2-Me)-c-Pr |
| 4-194 | c-Pr | $CHF_2$ | Me |
| 4-195 | c-Pr | $CHF_2$ | Et |
| 4-196 | c-Pr | $CHF_2$ | c-Pr |
| 4-197 | c-Pr | $CHF_2$ | $CH_2OMe$ |
| 4-198 | c-Pr | $CHF_2$ | $CH_2Cl$ |
| 4-199 | c-Pr | $CHF_2$ | (1-Me)-c-Pr |
| 4-200 | c-Pr | $CHF_2$ | (2-Me)-c-Pr |
| 4-201 | Cl | $CF_3$ | $(3,5-F_2)$-Ph |
| 4-202 | SMe | $CF_3$ | $(3,5-F_2)$-Ph |
| 4-203 | Cl | $CF_3$ | vinyl |
| 4-204 | Cl | $CF_3$ | (1-Me)-vinyl |
| 4-205 | Cl | $CF_3$ | (2-Me)-vinyl |
| 4-206 | Cl | $CF_3$ | $(1,2-Me_2)$-vinyl |
| 4-207 | Cl | $CF_3$ | $(2,2-Me_2)$-vinyl |
| 4-208 | Cl | $CHF_2$ | vinyl |
| 4-209 | Cl | $CHF_2$ | (1-Me)-vinyl |
| 4-210 | Cl | $CHF_2$ | (2-Me)-vinyl |
| 4-211 | Cl | $CHF_2$ | (1,2-diMe)-vinyl |
| 4-212 | Cl | $CHF_2$ | (2,2-diMe)-vinyl |
| 4-213 | Cl | $CF_3$ | ethynyl |
| 4-214 | Cl | $CF_3$ | 1-propynyl |

TABLE 5

Compounds of the formula (II) according to the invention in which L represents hydroxy and the other substituents have the meanings listed below

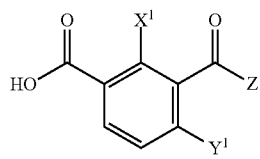

| No. | $X^1$ | $Y^1$ | Z |
|---|---|---|---|
| 5-1 | Me | $CF_3$ | Me |
| 5-2 | Me | $CF_3$ | Et |
| 5-3 | Me | $CF_3$ | n-Pr |
| 5-4 | Me | $CF_3$ | i-Pr |
| 5-5 | Me | $CF_3$ | c-Pr |
| 5-6 | Me | $CF_3$ | n-Bu |
| 5-7 | Me | $CF_3$ | t-Bu |
| 5-8 | Me | $CF_3$ | $CH_2OMe$ |
| 5-9 | Me | $CF_3$ | $CH_2Cl$ |
| 5-10 | Me | $CF_3$ | Ac |

TABLE 5-continued

Compounds of the formula (II) according to the invention in which L represents hydroxy and the other substituents have the meanings listed below

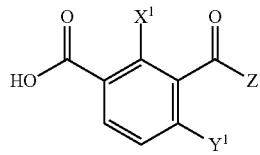

| No. | X¹ | Y¹ | Z |
|---|---|---|---|
| 5-11 | Me | $CF_3$ | (1-Me)-c-Pr |
| 5-12 | Me | $CF_3$ | (2-Me)-c-Pr |
| 5-13 | Me | $CF_3$ | (2,2-$Me_2$)-c-Pr |
| 5-14 | Me | $CF_3$ | (1,2-$Me_2$)-c-Pr |
| 5-15 | Me | $CF_3$ | (2-F)-c-Pr |
| 5-16 | Me | $CF_3$ | (2,2-$F_2$)-c-Pr |
| 5-17 | Me | $CF_3$ | c-Bu |
| 5-18 | Me | $CF_3$ | c-pentyl |
| 5-19 | Me | $CF_3$ | c-hexyl |
| 5-20 | Me | $CF_3$ | 2-thienyl |
| 5-21 | Me | $CF_3$ | 2-furyl |
| 5-22 | Me | $CF_3$ | Ph |
| 5-23 | Me | $CF_3$ | (4-MeO)-Ph |
| 5-24 | Me | $CF_3$ | (4-Cl)-Ph |
| 5-25 | Me | $CF_3$ | (3-$CF_3$)-Ph |
| 5-26 | Me | $CF_3$ | $CF_3$ |
| 5-27 | Me | $CF_3$ | $CHF_2$ |
| 5-28 | Me | $CHF_2$ | Me |
| 5-29 | Me | $CHF_2$ | Et |
| 5-30 | Me | $CHF_2$ | c-Pr |
| 5-31 | Me | $CHF_2$ | $CH_2OMe$ |
| 5-32 | Me | $CHF_2$ | $CH_2Cl$ |
| 5-33 | Me | $CHF_2$ | (1-Me)-c-Pr |
| 5-34 | Me | $CHF_2$ | (2-Me)-c-Pr |
| 5-35 | OMe | $CF_3$ | Me |
| 5-36 | OMe | $CF_3$ | Et |
| 5-37 | OMe | $CF_3$ | c-Pr |
| 5-38 | OMe | $CF_3$ | $CH_2OMe$ |
| 5-39 | OMe | $CF_3$ | $CH_2Cl$ |
| 5-40 | OMe | $CF_3$ | (1-Me)-c-Pr |
| 5-41 | OMe | $CF_3$ | (2-Me)-c-Pr |
| 5-42 | OMe | $CHF_2$ | Me |
| 5-43 | OMe | $CHF_2$ | Et |
| 5-44 | OMe | $CHF_2$ | c-Pr |
| 5-45 | SMe | $CF_3$ | Me |
| 5-46 | SMe | $CF_3$ | Et |
| 5-47 | SMe | $CF_3$ | n-Pr |
| 5-48 | SMe | $CF_3$ | i-Pr |
| 5-49 | SMe | $CF_3$ | c-Pr |
| 5-50 | SMe | $CF_3$ | n-Bu |
| 5-51 | SMe | $CF_3$ | t-Bu |
| 5-52 | SMe | $CF_3$ | $CH_2OMe$ |
| 5-53 | SMe | $CF_3$ | $CH_2Cl$ |
| 5-54 | SMe | $CF_3$ | Ac |
| 5-55 | SMe | $CF_3$ | (1-Me)-c-Pr |
| 5-56 | SMe | $CF_3$ | (2-Me)-c-Pr |
| 5-57 | SMe | $CF_3$ | (2,2-$Me_2$)-c-Pr |
| 5-58 | SMe | $CF_3$ | (1,2-$Me_2$)-c-Pr |
| 5-59 | SMe | $CF_3$ | (2-F)-c-Pr |
| 5-60 | SMe | $CF_3$ | (2,2-$F_2$)-c-Pr |
| 5-61 | SMe | $CF_3$ | c-Bu |
| 5-62 | SMe | $CF_3$ | c-pentyl |
| 5-63 | SMe | $CF_3$ | c-hexyl |
| 5-64 | SMe | $CF_3$ | 2-thienyl |
| 5-65 | SMe | $CF_3$ | 2-furyl |
| 5-66 | SMe | $CF_3$ | Ph |
| 5-67 | SMe | $CF_3$ | (4-MeO)-Ph |
| 5-68 | SMe | $CF_3$ | (4-Cl)-Ph |
| 5-69 | SMe | $CF_3$ | (3-$CF_3$)-Ph |
| 5-70 | SMe | $CF_3$ | $CF_3$ |
| 5-71 | SMe | $CF_3$ | $CHF_2$ |
| 5-72 | SMe | $CHF_2$ | Me |
| 5-73 | SMe | $CHF_2$ | Et |
| 5-74 | SMe | $CHF_2$ | c-Pr |
| 5-75 | SMe | $CHF_2$ | $CH_2OMe$ |
| 5-76 | SMe | $CHF_2$ | $CH_2Cl$ |
| 5-77 | SMe | $CHF_2$ | (1-Me)-c-Pr |

TABLE 5-continued

Compounds of the formula (II) according to the invention in which L represents hydroxy and the other substituents have the meanings listed below

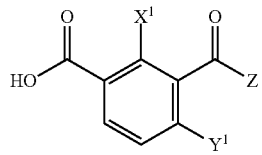

| No. | $X^1$ | $Y^1$ | Z |
|---|---|---|---|
| 5-78 | SMe | $CHF_2$ | (2-Me)-c-Pr |
| 5-79 | SEt | $CF_3$ | Me |
| 5-80 | SEt | $CF_3$ | Et |
| 5-81 | SEt | $CF_3$ | c-Pr |
| 5-82 | SEt | $CF_3$ | $CH_2OMe$ |
| 5-83 | SEt | $CF_3$ | $CH_2Cl$ |
| 5-84 | SEt | $CF_3$ | (1-Me)-c-Pr |
| 5-85 | SEt | $CF_3$ | (2-Me)-c-Pr |
| 5-86 | SEt | $CHF_2$ | Me |
| 5-87 | SEt | $CHF_2$ | Et |
| 5-88 | SEt | $CHF_2$ | c-Pr |
| 5-89 | SEt | $CHF_2$ | $CH_2OMe$ |
| 5-90 | SEt | $CHF_2$ | $CH_2Cl$ |
| 5-91 | SEt | $CHF_2$ | (1-Me)-c-Pr |
| 5-92 | SEt | $CHF_2$ | (2-Me)-c-Pr |
| 5-93 | F | $CF_3$ | Me |
| 5-94 | F | $CF_3$ | Et |
| 5-95 | F | $CF_3$ | c-Pr |
| 5-96 | F | $CHF_2$ | Me |
| 5-97 | F | $CHF_2$ | Et |
| 5-98 | F | $CHF_2$ | c-Pr |
| 5-99 | Cl | $CF_3$ | Me |
| 5-100 | Cl | $CF_3$ | Et |
| 5-101 | Cl | $CF_3$ | n-Pr |
| 5-102 | Cl | $CF_3$ | i-Pr |
| 5-103 | Cl | $CF_3$ | c-Pr |
| 5-104 | Cl | $CF_3$ | n-Bu |
| 5-105 | Cl | $CF_3$ | t-Bu |
| 5-106 | Cl | $CF_3$ | $CH_2OMe$ |
| 5-107 | Cl | $CF_3$ | $CH_2Cl$ |
| 5-108 | Cl | $CF_3$ | Ac |
| 5-109 | Cl | $CF_3$ | (1-Me)-c-Pr |
| 5-110 | Cl | $CF_3$ | (2-Me)-c-Pr |
| 5-111 | Cl | $CF_3$ | $(2,2-Me_2)$-c-Pr |
| 5-112 | Cl | $CF_3$ | $(1,2-Me_2)$-c-Pr |
| 5-113 | Cl | $CF_3$ | (2-F)-c-Pr |
| 5-114 | Cl | $CF_3$ | $(2,2-F_2)$-c-Pr |
| 5-115 | Cl | $CF_3$ | c-Bu |
| 5-116 | Cl | $CF_3$ | c-pentyl |
| 5-117 | Cl | $CF_3$ | c-hexyl |
| 5-118 | Cl | $CF_3$ | 2-thienyl |
| 5-119 | Cl | $CF_3$ | 2-furyl |
| 5-120 | Cl | $CF_3$ | Ph |
| 5-121 | Cl | $CF_3$ | (4-MeO)-Ph |
| 5-122 | Cl | $CF_3$ | (4-Cl)-Ph |
| 5-123 | Cl | $CF_3$ | $(3-CF_3)$-Ph |
| 5-124 | Cl | $CF_3$ | $CF_3$ |
| 5-125 | Cl | $CF_3$ | $CHF_2$ |
| 5-126 | Cl | $CHF_2$ | Me |
| 5-127 | Cl | $CHF_2$ | Et |
| 5-128 | Cl | $CHF_2$ | n-Pr |
| 5-129 | Cl | $CHF_2$ | i-Pr |
| 5-130 | Cl | $CHF_2$ | c-Pr |
| 5-131 | Cl | $CHF_2$ | n-Bu |
| 5-132 | Cl | $CHF_2$ | t-Bu |
| 5-133 | Cl | $CHF_2$ | $CH_2OMe$ |
| 5-134 | Cl | $CHF_2$ | $CH_2Cl$ |
| 5-135 | Cl | $CHF_2$ | Ac |
| 5-136 | Cl | $CHF_2$ | (1-Me)-c-Pr |
| 5-137 | Cl | $CHF_2$ | (2-Me)-c-Pr |
| 5-138 | Cl | $CHF_2$ | $(2,2-Me_2)$-c-Pr |
| 5-139 | Cl | $CHF_2$ | $(1,2-Me_2)$-c-Pr |
| 5-140 | Cl | $CHF_2$ | (2-F)-c-Pr |
| 5-141 | Cl | $CHF_2$ | $(2,2-F_2)$-c-Pr |
| 5-142 | Cl | $CHF_2$ | c-Bu |
| 5-143 | Cl | $CHF_2$ | c-pentyl |
| 5-144 | Cl | $CHF_2$ | c-hexyl |

TABLE 5-continued

Compounds of the formula (II) according to the invention in which L represents hydroxy and the other substituents have the meanings listed below

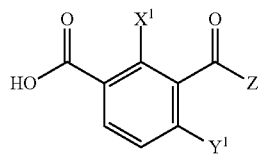

| No. | $X^1$ | $Y^1$ | Z |
|---|---|---|---|
| 5-145 | Cl | $CHF_2$ | 2-thienyl |
| 5-146 | Cl | $CHF_2$ | 2-furyl |
| 5-147 | Cl | $CHF_2$ | Ph |
| 5-148 | Cl | $CHF_2$ | (4-MeO)-Ph |
| 5-149 | Cl | $CHF_2$ | (4-Cl)-Ph |
| 5-150 | Cl | $CHF_2$ | (3-$CF_3$)-Ph |
| 5-151 | Cl | $CHF_2$ | $CF_3$ |
| 5-152 | Cl | $CHF_2$ | $CHF_2$ |
| 5-153 | Br | $CF_3$ | Me |
| 5-154 | Br | $CF_3$ | Et |
| 5-155 | Br | $CF_3$ | c-Pr |
| 5-156 | Br | $CF_3$ | $CH_2OMe$ |
| 5-157 | Br | $CF_3$ | $CH_2Cl$ |
| 5-158 | Br | $CF_3$ | (1-Me)-c-Pr |
| 5-159 | Br | $CF_3$ | (2-Me)-c-Pr |
| 5-160 | Br | $CHF_2$ | Me |
| 5-161 | Br | $CHF_2$ | Et |
| 5-162 | Br | $CHF_2$ | c-Pr |
| 5-163 | Br | $CHF_2$ | $CH_2OMe$ |
| 5-164 | Br | $CHF_2$ | $CH_2Cl$ |
| 5-165 | Br | $CHF_2$ | (1-Me)-c-Pr |
| 5-166 | Br | $CHF_2$ | (2-Me)-c-Pr |
| 5-167 | I | $CF_3$ | Me |
| 5-168 | I | $CF_3$ | Et |
| 5-169 | I | $CF_3$ | c-Pr |
| 5-170 | I | $CF_3$ | $CH_2OMe$ |
| 5-171 | I | $CF_3$ | $CH_2Cl$ |
| 5-172 | I | $CF_3$ | (1-Me)-c-Pr |
| 5-173 | I | $CF_3$ | (2-Me)-c-Pr |
| 5-174 | I | $CHF_2$ | Me |
| 5-175 | I | $CHF_2$ | Et |
| 5-176 | I | $CHF_2$ | c-Pr |
| 5-177 | I | $CHF_2$ | $CH_2OMe$ |
| 5-178 | I | $CHF_2$ | $CH_2Cl$ |
| 5-179 | I | $CHF_2$ | (1-Me)-c-Pr |
| 5-180 | I | $CHF_2$ | (2-Me)-c-Pr |
| 5-181 | Et | $CF_3$ | Me |
| 5-182 | Et | $CF_3$ | Et |
| 5-183 | Et | $CF_3$ | c-Pr |
| 5-184 | Et | $CHF_2$ | Me |
| 5-185 | Et | $CHF_2$ | Et |
| 5-186 | Et | $CHF_2$ | c-Pr |
| 5-187 | c-Pr | $CF_3$ | Me |
| 5-188 | c-Pr | $CF_3$ | Et |
| 5-189 | c-Pr | $CF_3$ | c-Pr |
| 5-190 | c-Pr | $CF_3$ | $CH_2OMe$ |
| 5-191 | c-Pr | $CF_3$ | $CH_2Cl$ |
| 5-192 | c-Pr | $CF_3$ | (1-Me)-c-Pr |
| 5-193 | c-Pr | $CF_3$ | (2-Me)-c-Pr |
| 5-194 | c-Pr | $CHF_2$ | Me |
| 5-195 | c-Pr | $CHF_2$ | Et |
| 5-196 | c-Pr | $CHF_2$ | c-Pr |
| 5-197 | c-Pr | $CHF_2$ | $CH_2OMe$ |
| 5-198 | c-Pr | $CHF_2$ | $CH_2Cl$ |
| 5-199 | c-Pr | $CHF_2$ | (1-Me)-c-Pr |
| 5-200 | c-Pr | $CHF_2$ | (2-Me)-c-Pr |
| 5-201 | Cl | $CF_3$ | (3,5-$F_2$)-Ph |
| 5-202 | SMe | $CF_3$ | (3,5-$F_2$)-Ph |
| 5-203 | Cl | $CF_3$ | vinyl |

TABLE 6

Compounds of the formula (II) according to the invention in which L represents chlorine and the other substituents have the meanings listed below

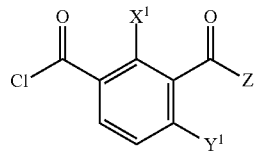

| No. | X¹ | Y² | Z |
|---|---|---|---|
| 6-1 | Me | $CF_3$ | Me |
| 6-2 | Me | $CF_3$ | Et |
| 6-3 | Me | $CF_3$ | n-Pr |
| 6-4 | Me | $CF_3$ | i-Pr |
| 6-5 | Me | $CF_3$ | c-Pr |
| 6-6 | Me | $CF_3$ | n-Bu |
| 6-7 | Me | $CF_3$ | t-Bu |
| 6-8 | Me | $CF_3$ | $CH_2OMe$ |
| 6-9 | Me | $CF_3$ | $CH_2Cl$ |
| 6-10 | Me | $CF_3$ | Ac |
| 6-11 | Me | $CF_3$ | (1-Me)-c-Pr |
| 6-12 | Me | $CF_3$ | (2-Me)-c-Pr |
| 6-13 | Me | $CF_3$ | (2,2-$Me_2$)-c-Pr |
| 6-14 | Me | $CF_3$ | (1,2-$Me_2$)-c-Pr |
| 6-15 | Me | $CF_3$ | (2-F)-c-Pr |
| 6-16 | Me | $CF_3$ | (2,2-$F_2$)-c-Pr |
| 6-17 | Me | $CF_3$ | c-Bu |
| 6-18 | Me | $CF_3$ | c-pentyl |
| 6-19 | Me | $CF_3$ | c-hexyl |
| 6-20 | Me | $CF_3$ | 2-thienyl |
| 6-21 | Me | $CF_3$ | 2-furyl |
| 6-22 | Me | $CF_3$ | Ph |
| 6-23 | Me | $CF_3$ | (4-MeO)-Ph |
| 6-24 | Me | $CF_3$ | (4-Cl)-Ph |
| 6-25 | Me | $CF_3$ | (3-$CF_3$)-Ph |
| 6-26 | Me | $CF_3$ | $CF_3$ |
| 6-27 | Me | $CF_3$ | $CHF_2$ |
| 6-28 | Me | $CHF_2$ | Me |
| 6-29 | Me | $CHF_2$ | Et |
| 6-30 | Me | $CHF_2$ | c-Pr |
| 6-31 | Me | $CHF_2$ | $CH_2OMe$ |
| 6-32 | Me | $CHF_2$ | $CH_2Cl$ |
| 6-33 | Me | $CHF_2$ | (1-Me)-c-Pr |
| 6-34 | Me | $CHF_2$ | (2-Me)-c-Pr |
| 6-35 | OMe | $CF_3$ | Me |
| 6-36 | OMe | $CF_3$ | Et |
| 6-37 | OMe | $CF_3$ | c-Pr |
| 6-38 | OMe | $CF_3$ | $CH_2OMe$ |
| 6-39 | OMe | $CF_3$ | $CH_2Cl$ |
| 6-40 | OMe | $CF_3$ | (1-Me)-c-Pr |
| 6-41 | OMe | $CF_3$ | (2-Me)-c-Pr |
| 6-42 | OMe | $CHF_2$ | Me |
| 6-43 | OMe | $CHF_2$ | Et |
| 6-44 | OMe | $CHF_2$ | c-Pr |
| 6-45 | SMe | $CF_3$ | Me |
| 6-46 | SMe | $CF_3$ | Et |
| 6-47 | SMe | $CF_3$ | n-Pr |
| 6-48 | SMe | $CF_3$ | i-Pr |
| 6-49 | SMe | $CF_3$ | c-Pr |
| 6-50 | SMe | $CF_3$ | n-Bu |
| 6-51 | SMe | $CF_3$ | t-Bu |
| 6-52 | SMe | $CF_3$ | $CH_2OMe$ |
| 6-53 | SMe | $CF_3$ | $CH_2Cl$ |
| 6-54 | SMe | $CF_3$ | Ac |
| 6-55 | SMe | $CF_3$ | (1-Me)-c-Pr |
| 6-56 | SMe | $CF_3$ | (2-Me)-c-Pr |
| 6-57 | SMe | $CF_3$ | (2,2-$Me_2$)-c-Pr |
| 6-58 | SMe | $CF_3$ | (1,2-$Me_2$)-c-Pr |
| 6-59 | SMe | $CF_3$ | (2-F)-c-Pr |
| 6-60 | SMe | $CF_3$ | (2,2-$F_2$)-c-Pr |
| 6-61 | SMe | $CF_3$ | c-Bu |
| 6-62 | SMe | $CF_3$ | c-pentyl |
| 6-63 | SMe | $CF_3$ | c-hexyl |
| 6-64 | SMe | $CF_3$ | 2-thienyl |
| 6-65 | SMe | $CF_3$ | 2-furyl |
| 6-66 | SMe | $CF_3$ | Ph |
| 6-67 | SMe | $CF_3$ | (4-MeO)-Ph |

TABLE 6-continued

Compounds of the formula (II) according to the invention in which L represents chlorine and the other substituents have the meanings listed below

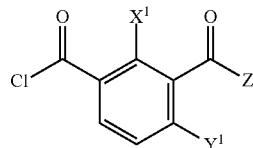

| No. | X¹ | Y² | Z |
|---|---|---|---|
| 6-68 | SMe | $CF_3$ | (4-Cl)-Ph |
| 6-69 | SMe | $CF_3$ | (3-$CF_3$)-Ph |
| 6-70 | SMe | $CF_3$ | $CF_3$ |
| 6-71 | SMe | $CF_3$ | $CHF_2$ |
| 6-72 | SMe | $CHF_2$ | Me |
| 6-73 | SMe | $CHF_2$ | Et |
| 6-74 | SMe | $CHF_2$ | c-Pr |
| 6-75 | SMe | $CHF_2$ | $CH_2OMe$ |
| 6-76 | SMe | $CHF_2$ | $CH_2Cl$ |
| 6-77 | SMe | $CHF_2$ | (1-Me)-c-Pr |
| 6-78 | SMe | $CHF_2$ | (2-Me)-c-Pr |
| 6-79 | SEt | $CF_3$ | Me |
| 6-80 | SEt | $CF_3$ | Et |
| 6-81 | SEt | $CF_3$ | c-Pr |
| 6-82 | SEt | $CF_3$ | $CH_2OMe$ |
| 6-83 | SEt | $CF_3$ | $CH_2Cl$ |
| 6-84 | SEt | $CF_3$ | (1-Me)-c-Pr |
| 6-85 | SEt | $CF_3$ | (2-Me)-c-Pr |
| 6-86 | SEt | $CHF_2$ | Me |
| 6-87 | SEt | $CHF_2$ | Et |
| 6-88 | SEt | $CHF_2$ | c-Pr |
| 6-89 | SEt | $CHF_2$ | $CH_2OMe$ |
| 6-90 | SEt | $CHF_2$ | $CH_2Cl$ |
| 6-91 | SEt | $CHF_2$ | (1-Me)-c-Pr |
| 6-92 | SEt | $CHF_2$ | (2-Me)-c-Pr |
| 6-93 | F | $CF_3$ | Me |
| 6-94 | F | $CF_3$ | Et |
| 6-95 | F | $CF_3$ | c-Pr |
| 6-96 | F | $CHF_2$ | Me |
| 6-97 | F | $CHF_2$ | Et |
| 6-98 | F | $CHF_2$ | c-Pr |
| 6-99 | Cl | $CF_3$ | Me |
| 6-100 | Cl | $CF_3$ | Et |
| 6-101 | Cl | $CF_3$ | n-Pr |
| 6-102 | Cl | $CF_3$ | i-Pr |
| 6-103 | Cl | $CF_3$ | c-Pr |
| 6-104 | Cl | $CF_3$ | n-Bu |
| 6-105 | Cl | $CF_3$ | t-Bu |
| 6-106 | Cl | $CF_3$ | $CH_2OMe$ |
| 6-107 | Cl | $CF_3$ | $CH_2Cl$ |
| 6-108 | Cl | $CF_3$ | Ac |
| 6-109 | Cl | $CF_3$ | (1-Me)-c-Pr |
| 6-110 | Cl | $CF_3$ | (2-Me)-c-Pr |
| 6-111 | Cl | $CF_3$ | (2,2-$Me_2$)-c-Pr |
| 6-112 | Cl | $CF_3$ | (1,2-$Me_2$)-c-Pr |
| 6-113 | Cl | $CF_3$ | (2-F)-c-Pr |
| 6-114 | Cl | $CF_3$ | (2,2-$F_2$)-c-Pr |
| 6-115 | Cl | $CF_3$ | c-Bu |
| 6-116 | Cl | $CF_3$ | c-pentyl |
| 6-117 | Cl | $CF_3$ | c-hexyl |
| 6-118 | Cl | $CF_3$ | 2-thienyl |
| 6-119 | Cl | $CF_3$ | 2-furyl |
| 6-120 | Cl | $CF_3$ | Ph |
| 6-121 | Cl | $CF_3$ | (4-MeO)-Ph |
| 6-122 | Cl | $CF_3$ | (4-Cl)-Ph |
| 6-123 | Cl | $CF_3$ | (3-$CF_3$)-Ph |
| 6-124 | Cl | $CF_3$ | $CF_3$ |
| 6-125 | Cl | $CF_3$ | $CHF_2$ |
| 6-126 | Cl | $CHF_2$ | Me |
| 6-127 | Cl | $CHF_2$ | Et |
| 6-128 | Cl | $CHF_2$ | n-Pr |
| 6-129 | Cl | $CHF_2$ | i-Pr |
| 6-130 | Cl | $CHF_2$ | c-Pr |
| 6-131 | Cl | $CHF_2$ | n-Bu |
| 6-132 | Cl | $CHF_2$ | t-Bu |
| 6-133 | Cl | $CHF_2$ | $CH_2OMe$ |
| 6-134 | Cl | $CHF_2$ | $CH_2Cl$ |

TABLE 6-continued

Compounds of the formula (II) according to the invention in which L represents chlorine and the other substituents have the meanings listed below

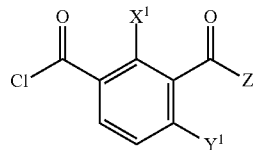

| No. | X¹ | Y² | Z |
|---|---|---|---|
| 6-135 | Cl | CHF$_2$ | Ac |
| 6-136 | Cl | CHF$_2$ | (1-Me)-c-Pr |
| 6-137 | Cl | CHF$_2$ | (2-Me)-c-Pr |
| 6-138 | Cl | CHF$_2$ | (2,2-Me$_2$)-c-Pr |
| 6-139 | Cl | CHF$_2$ | (1,2-Me$_2$)-c-Pr |
| 6-140 | Cl | CHF$_2$ | (2-F)-c-Pr |
| 6-141 | Cl | CHF$_2$ | (2,2-F$_2$)-c-Pr |
| 6-142 | Cl | CHF$_2$ | c-Bu |
| 6-143 | Cl | CHF$_2$ | c-pentyl |
| 6-144 | Cl | CHF$_2$ | c-hexyl |
| 6-145 | Cl | CHF$_2$ | 2-thienyl |
| 6-146 | Cl | CHF$_2$ | 2-furyl |
| 6-147 | Cl | CHF$_2$ | Ph |
| 6-148 | Cl | CHF$_2$ | (4-MeO)-Ph |
| 6-149 | Cl | CHF$_2$ | (4-Cl)-Ph |
| 6-150 | Cl | CHF$_2$ | (3-CF$_3$)-Ph |
| 6-151 | Cl | CHF$_2$ | CF$_3$ |
| 6-152 | Cl | CHF$_2$ | CHF$_2$ |
| 6-153 | Br | CF$_3$ | Me |
| 6-154 | Br | CF$_3$ | Et |
| 6-155 | Br | CF$_3$ | c-Pr |
| 6-156 | Br | CF$_3$ | CH$_2$OMe |
| 6-157 | Br | CF$_3$ | CH$_2$Cl |
| 6-158 | Br | CF$_3$ | (1-Me)-c-Pr |
| 6-159 | Br | CF$_3$ | (2-Me)-c-Pr |
| 6-160 | Br | CHF$_2$ | Me |
| 6-161 | Br | CHF$_2$ | Et |
| 6-162 | Br | CHF$_2$ | c-Pr |
| 6-163 | Br | CHF$_2$ | CH$_2$OMe |
| 6-164 | Br | CHF$_2$ | CH$_2$Cl |
| 6-165 | Br | CHF$_2$ | (1-Me)-c-Pr |
| 6-166 | Br | CHF$_2$ | (2-Me)-c-Pr |
| 6-167 | I | CF$_3$ | Me |
| 6-168 | I | CF$_3$ | Et |
| 6-169 | I | CF$_3$ | c-Pr |
| 6-170 | I | CF$_3$ | CH$_2$OMe |
| 6-171 | I | CF$_3$ | CH$_2$Cl |
| 6-172 | I | CF$_3$ | (1-Me)-c-Pr |
| 6-173 | I | CF$_3$ | (2-Me)-c-Pr |
| 6-174 | I | CHF$_2$ | Me |
| 6-175 | I | CHF$_2$ | Et |
| 6-176 | I | CHF$_2$ | c-Pr |
| 6-177 | I | CHF$_2$ | CH$_2$OMe |
| 6-178 | I | CHF$_2$ | CH$_2$Cl |
| 6-179 | I | CHF$_2$ | (1-Me)-c-Pr |
| 6-180 | I | CHF$_2$ | (2-Me)-c-Pr |
| 6-181 | Et | CF$_3$ | Me |
| 6-182 | Et | CF$_3$ | Et |
| 6-183 | Et | CF$_3$ | c-Pr |
| 6-184 | Et | CHF$_2$ | Me |
| 6-185 | Et | CHF$_2$ | Et |
| 6-186 | Et | CHF$_2$ | c-Pr |
| 6-187 | c-Pr | CF$_3$ | Me |
| 6-188 | c-Pr | CF$_3$ | Et |
| 6-189 | c-Pr | CF$_3$ | c-Pr |
| 6-190 | c-Pr | CF$_3$ | CH$_2$OMe |
| 6-191 | c-Pr | CF$_3$ | CH$_2$Cl |
| 6-192 | c-Pr | CF$_3$ | (1-Me)-c-Pr |
| 6-193 | c-Pr | CF$_3$ | (2-Me)-c-Pr |
| 6-194 | c-Pr | CHF$_2$ | Me |
| 6-195 | c-Pr | CHF$_2$ | Et |
| 6-196 | c-Pr | CHF$_2$ | c-Pr |
| 6-197 | c-Pr | CHF$_2$ | CH$_2$OMe |
| 6-198 | c-Pr | CHF$_2$ | CH$_2$Cl |
| 6-199 | c-Pr | CHF$_2$ | (1-Me)-c-Pr |
| 6-200 | c-Pr | CHF$_2$ | (2-Me)-c-Pr |

TABLE 6-continued

Compounds of the formula (II) according to the invention in which L represents chlorine and the other substituents have the meanings listed below

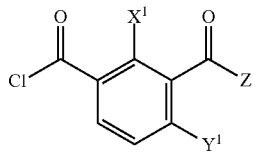

| No. | $X^1$ | $Y^2$ | Z |
|---|---|---|---|
| 6-201 | Cl | $CF_3$ | (3,5-$F_2$)-Ph |
| 6-202 | SMe | $CF_3$ | (3,5-$F_2$)-Ph |

NMR data for numerous compounds of the formula (I) according to the invention mentioned in the tables above are disclosed below using the NMR peak list method. Here, the $^1$H NMR data of selected examples are stated in the form of $^1$H NMR peak lists. For each signal peak, first the δ value in ppm and then the signal intensity in round brackets are listed. The pairs of δ value-signal intensity numbers for different signal peaks are listed with separation from one another by semicolons. The peak list for one example therefore takes the form of:

δ$_1$(intensity$_1$);δ$_2$(intensity$_2$); . . . ;δ$_i$(intensity$_i$); . . . ;δ$_n$(intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-$D_6$ and the peak of water, which usually have a high intensity on average.

The peaks of stereoisomers of the compounds of the invention and/or peaks of impurities usually have a lower intensity on average than the peaks of the compounds of the invention (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the compounds of the invention, optionally using additional intensity filters. This isolation would be similar to the peak picking in question in conventional $^1$H NMR interpretation.

Example No. 1-1

$^1$H-NMR (400 Mhz, DMSO-$d_6$): δ=11.48 (br s, 1H); 7.58 (d, 1H); 7.25 (d, 1H); 3.97 (s, 3H); 2.50 (s, 3H); 2.27 (s, 3H); 2.24 (s, 3H);

Example No. 1-3

$^1$H-NMR (400 Mhz, DMSO-$d_6$): δ=11.49 (br s, 1H); 7.59 (d, 1H); 7.27 (d, 1H); 3.97 (s, 3H); 2.30 (s, 3H); 2.26 (s, 3H); 2.25 (m, 1H); 1.15 (m, 4H);

Example No. 1-7

$^1$H-NMR (400 Mhz, DMSO-$d_6$): δ=11.81 (br s, 1H); 7.97 (d, 1H); 7.93 (d, 1H); 4.01 (s, 3H); 3.22 (s, 3H); 2.59 (s, 3H); 2.35 (s, 3H);

Example No. 1-9

$^1$H-NMR (400 Mhz, DMSO-$d_6$): δ=11.84 (br s, 1H); 7.96 (d, 1H); 7.91 (d, 1H); 3.99 (s, 3H); 3.21 (s, 3H); 2.41 (s, 3H); 2.36 (m, 1H); 1.22 (m, 4H);

Example No. 1-14

$^1$H-NMR (400 Mhz, DMSO-$d_6$): δ=11.79 (br s, 1H); 7.88 (d, 1H); 7.83 (d, 1H); 4.01 s, 3H); 2.57 (s, 3H); 2.34 (s, 3H);

Example No. 1-15

$^1$H-NMR (400 Mhz, DMSO-$d_6$): δ=11.77 (br s, 1H); 7.89 (d, 1H); 7.83 (d, 1H); 4.01 (s, 3H); 2.85 (q, 2H); 2.29 (s, 3H); 1.12 (t, 3H);

Example No. 1-16

$^1$H-NMR (400 Mhz, DMSO-$d_6$): δ=11.77 (br s, 1H); 7.89 (d, 1H); 7.83 (d, 1H); 4.01 (s, 3H); 2.82 (t, 2H); 2.30 (s, 3H); 1.66 (m, 2H); 0.96 (t, 3H);

Example No. 1-18

$^1$H-NMR (400 Mhz, DMSO-$d_6$): δ=11.67 (br s, 1H); 7.88 (d, 1H); 7.83 (d, 1H); 4.36 (q, 2H); 2.38 (s, 3H); 2.35 (m, 1H); 1.47 (t, 3H); 1.23 (m, 4H);

Example No. 1-21

¹H-NMR (400 Mhz, DMSO-$d_6$): δ=11.80 (br s, 1H); 7.92 (d, 1H); 7.84 (d, 1H); 4.45 (s, 2H); 4.01 (s, 3H); 3.36 (s, 3H); 2.33 (s, 3H);

Example No. 1-22

¹H-NMR (400 Mhz, DMSO-$d_6$): δ=11.71 (br s, 1H); 7.96 (d, 1H); 7.89 (d, 1H); 4.97 (s, 2H); 4.36 (q, 2H); 2.33 (s, 3H); 1.47 (s, 3H);

Example No. 1-48

¹H-NMR (400 Mhz, DMSO-$d_6$): δ=11.76 (br s, 1H); 7.94 (d, 1H); 7.72 (d, 1H); 4.01 (s, 3H); 3.84 (s, 1H); 2.54 (s, 3H);

Example No. 1-50

¹H-NMR (400 Mhz, DMSO-$d_6$): δ=11.78 (br s, 1H); 7.94 (d, 1H); 7.74 (d, 1H); 4.01 (s, 3H); 3.84 (s, 3H); 2.35 (m, 1H); 1.16 (m, 4H);

Example No. 1-58

¹H-NMR (400 Mhz, CDCl$_3$): δ=11.06 (br s, 1H); 7.84 (m, 2H); 4.16 (s, 3H); 2.67 (s, 3H); 2.40 (s, 3H);

Example No. 1-60

¹H-NMR (400 Mhz, DMSO-$d_6$): δ=11.83 (br s, 1H); 8.03 (d, 1H); 7.95 (d, 1H); 4.05 (s, 3H); 2.37 (m, 1H); 2.37 (s, 3H); 1.24 (m, 4H);

Example No. 1-65

¹H-NMR (400 Mhz, DMSO-$d_6$): δ=11.78 (br s, 1H); 7.85 (m, 2H); 7.09 (t, 1H); 4.05 (s, 3H); 2.61 (s, 3H); 2.34 (s, 3H);

Example No. 1-67

¹H-NMR (400 Mhz, DMSO-$d_6$): δ=11.78 (br s, 1H); 7.86 (m, 2H); 6.97 (t, 1H); 4.05 (3H); 2.36 (s, 3H); 2.35 (m, 1H); 1.25 (m, 2H); 1.20 (m, 2H);

Example No. 1-114

¹H-NMR (400 Mhz, DMSO-$d_6$): δ=11.90 (br s, 1H); 7.86 (d, 1H); 7.76 (d, 1H); 3.99 (s, 3H); 2.60 (s, 3H);

Example No. 1-115

¹H-NMR (400 Mhz, DMSO-$d_6$): δ=11.90 (br s, 1H); 7.86 (d, 1H); 7.76 (d, 1H); 3.99 (s, 3H); 2.89 (q, 2H); 1.14 (t, 3H);

Example No. 1-116

¹H-NMR (400 Mhz, DMSO-$d_6$): δ=11.91 (br s, 1H); 7.85 (d, 1H); 7.76 (d, 1H); 4.00 (s, 3H); 2.34 (m, 1H); 1.23 (m, 4H);

Example No. 1-121

¹H-NMR (400 Mhz, DMSO-$d_6$): δ=11.79 (br s, 1H); 7.78 (d, 1H); 7.55 (d, 1H); 3.98 (s, 3H); 2.58 (s, 3H); 2.55 (s, 3H);

Example No. 1-123

¹H-NMR (400 Mhz, DMSO-$d_6$): δ=11.77 (br s, 1H); 7.76 (d, 1H); 7.52 (d, 1H); 3.99 (s, 3H); 2.57 (s, 3H); 2.28 (m, 1H); 1.19 (m, 4H);

Example No. 1-127

¹H-NMR (400 Mhz, DMSO-$d_6$): δ=12.05 (br s, 1H); 8.11 (m, 2H); 4.02 (s, 3H); 3.29 (s, 3H); 2.63 (s, 3H);

Example No. 1-129

¹H-NMR (400 Mhz, DMSO-$d_6$): δ=12.04 (br s, 1H); 8.11 (m, 2H); 4.02 (s, 3H); 3.27 (s, 3H); 2.40 (m, 1H); 1.26 (m, 4H);

Example No. 1-134

¹H-NMR (400 Mhz, DMSO-$d_6$): δ=11.76 (br s, 1H); 7.68 (d, 1H); 7.43 (d, 1H); 3.98 (s, 3H); 2.56 (s, 3H); 2.28 (s, 3H);

Example No. 1-135

¹H-NMR (400 Mhz, DMSO-$d_6$): δ=11.78 (br s, 1H); 7.68 (d, 1H); 7.42 (d, 1H); 3.98 (s, 3H); 2.86 (q, 2H); 2.25 (s, 3H); 1.12 (t, 3H);

Example No. 1-136

¹H-NMR (400 Mhz, CDCl$_3$): δ=10.11 (br s, 1H); 7.72 (d, 1H); 7.31 (d, 1H); 4.10 (s, 3H); 2.36 (s, 3H); 2.28 (m, 1H); 1.38 (m, 2H); 1.18 (m, 2H);

Example No. 1-137

¹H-NMR (400 Mhz, DMSO-$d_6$): δ=12.00 (br s, 1H); 8.04 (m, 2H); 4.02 (s, 3H); 2.62 (s, 3H);

Example No. 1-138

¹H-NMR (400 Mhz, CDCl$_3$): δ=11.20 (br s, 1H); 7.87 (d, 1H); 7.77 (d, 1H); 4.13 (s, 3H); 2.91 (q, 2H); 1.25 (t, 3H);

Example No. 1-139

¹H-NMR (400 Mhz, DMSO-$d_6$): δ=12.03 (m, 2H); 4.02 (s, 3H); 2.98 (t, 2H); 1.69 (m, 2H); 0.97 (t, 3H);

Example No. 1-140

¹H-NMR (400 Mhz, DMSO-$d_6$): δ=12.02 (br s, 1H); 8.05 (m, 2H); 4.02 (s, 3H); 3.08 (m, 1H); 1.17 (d, 6H);

Example No. 1-141

¹H-NMR (400 Mhz, DMSO-$d_6$): δ=12.02 (br s, 1H); 8.05 (m, 2H); 4.02 (s, 3H); 2.51 (s, 3H); 2.39 (m, 1H); 1.25 (m, 4H);

Example No. 1-143

¹H-NMR (400 Mhz, DMSO-$d_6$): δ=12.07 (br s, 1H); 8.05 (s, 1H); 4.02 (s, 3H); 1.26 (s, 9H);

Example No. 1-144

¹H-NMR (400 Mhz, DMSO-d₆): δ=12.06 (br s, 1H); 8.10 (d, 1H); 8.05 (d, 1H); 4.50 (s, 2H); 3.37 (s, 3H);

Example No. 1-145

¹H-NMR (400 Mhz, DMSO-d₆): δ=12.04 (br s, 1H); 8.14 (d, 1H); 8.09 (d, 1H); 4.98 (s, 2H); 4.02 (s, 3H);

Example No. 1-146

¹H-NMR (400 Mhz, DMSO-d₆): δ=12.09 (br s, 1H); 8.19 (d, 1H); 8.12 (d, 1H); 4.01 (s, 3H); 2.59 (s, 3H);

Example No. 1-147

¹H-NMR (400 Mhz, DMSO-d₆): δ=12.05 (br s, 1H); 8.04 (s, 2H); 4.02 (s, 3H); 1.40 (d, 2H); 1.22 (s, 3H); 1.13 (d, 2H);

Example No. 1-148

¹H-NMR (400 Mhz, DMSO-d₆): δ=12.00 (br s, 1H); 8.03 (m, 2H); 4.02 (m, 3H); 2.07 (m, 1H); 1.62 (m, 1H); 1.50 (m, 1H); 1.18 (m, 1H); 1.16 d, 3H);

Example No. 1-149

¹H-NMR (400 Mhz, DMSO-d₆): δ=12.00 (br s, 1H); 8.01 (m, 2H); 4.02 (s, 3H); 2.22 (m, 1H); 1.38 (m, 2H); 1.29 (s, 3H); 1.22 (s, 3H);

Example No. 1-150

¹H-NMR (400 Mhz, DMSO-d₆): δ=12.07 (br s, 1H); 8.04 (br s, 2H); 4.02 (s, 3H); 1.64 (m, 2H); 1.17 (s, 3H); 1.15 (s, 3H); 0.88 (m, 1H);

Example No. 1-153

¹H-NMR (400 Mhz, DMSO-d₆): δ=12.00 (br s, 1H); 8.02 (m, 2H); 4.01 (s, 3H); 3.76 (m, 1H); 2.32 (m, 2H); 2.19 (m, 2H); 1.97 (m, 1H); 1.83 (m, 1H);

Example No. 1-154

¹H-NMR (400 Mhz, DMSO-d₆): δ=12.01 (br s, 1H); 8.04 (m, 2H); 4.02 (s, 3H); 3.34 (m, 1H); 1.94 (m, 2H); 1.79 (m, 2H); 1.64 (m, 4H);

Example No. 1-155

¹H-NMR (400 Mhz, DMSO-d₆): δ=12.01 (br s, 1H); 8.04 (m, 2H); 4.02 (s, 3H); 2.78 (m, 1H); 1.95 (m, 2H); 1.78 (m, 2H); 1.66 (m, 1H); 1.30 (m, 4H); 1.17 (m, 1H);

Example No. 1-162

¹H-NMR (400 Mhz, DMSO-d₆): δ=12.13 (br s, 1H); 8.35 (d, 1H); 8.27 (d, 1H); 4.02 (s, 3H);

Example No. 1-163

¹H-NMR (400 Mhz, DMSO-d₆): δ=12.11 (br s, 1H); 8.25 (d, 1H); 8.18 (d, 1H); 7.00 (t, 1H); 4.02 (s, 3H);

Example No. 1-164

¹H-NMR (400 Mhz, DMSO-d₆): δ=11.95 (br s, 1H); 7.96 (d, 1H); 7.81 (d, 1H); 7.13 (t, 1H); 4.01 (s, 3H); 2.60 (s. 3H);

Example No. 1-165

¹H-NMR (400 Mhz, DMSO-d₆): δ=11.97 (br s, 1H); 7.96 (d, 1H); 7.81 (d, 1H); 7.11 (t, 1H); 4.01 (s, 3H); 2.89 (q, 2H); 1.13 (t, 3H);

Example No. 1-168

¹H-NMR (400 Mhz, DMSO-d₆): δ=11.95 (br s, 1H); 7.97 (d, 1H); 7.82 (d, 1H); 7.05 (t, 1H); 4.01 (s, 3H); 2.38 (m, 1H); 1.23 (m, 4H);

Example No. 1-192

¹H-NMR (400 Mhz, DMSO-d₆): δ=11.86 (br s, 1H); 8.06 (d, 1H); 7.55 (d, 1H); 3.99 (s, 3H); 2.58 (s, 3H);

Example No. 1-194

¹H-NMR (400 Mhz, DMSO-d₆): δ=11.87 (br s, 1H); 8.06 (d, 1H); 7.54 (d, 1H); 3.99 (s, 3H); 2.29 (m, 1H); 1.25 (m, 4H);

Example No. 1-195

¹H-NMR (400 Mhz, DMSO-d₆): δ=12.00 (br s, 1H); 8.06 (d, 1H); 8.02 (d, 1H); 4.03 (s, 3H); 2.62 (s, 3H);

Example No. 1-197

¹H-NMR (400 Mhz, DMSO-d₆): δ=12.00 (br s, 1H); 8.05 (d, 1H); 8.00 (d, 1H); 8.04 (s, 3H); 2.36 (m, 1H); 1.27 (m, 4H);

Example No. 1-202

¹H-NMR (400 Mhz, DMSO-d₆): δ=11.94 (br s, 1H); 7.91 (d, 1H); 7.84 (d, 1H); 7.12 (t, 1H); 4.03 (s, 3H); 2.6 (s, 3H);

Example No. 1-203

¹H-NMR (400 Mhz, CDCl₃): δ=10.77 (br s, 1H); 7.78 (d, 1H); 7.75 (d, 1H); 6.68 (t, 1H); 4.15 (s, 3H); 2.95 (q, 2H); 2.26 (t, 3H);

Example No. 1-204

¹H-NMR (400 Mhz, DMSO-d₆): δ=11.96 (br s, 1H); 7.92 (d, 1H); 7.86 (d, 1H); 7.03 (t, 1H); 4.03 (s, 3H); 2.34 (m, 1H); 1.26 (m, 4H);

Example No. 1-231

¹H-NMR (400 Mhz, DMSO-d₆): δ=11.72 (br s, 1H); 7.84 (m, 2H); 4.04 (s, 3H); 2.64 (s, 3H); 2.28 (m, 1H); 0.95 (m, 2H); 5.54 (m, 2H);

Example No. 1-233

¹H-NMR (400 Mhz, DMSO-d₆): δ=11.73 (br s, 1H); 7.83 (m, 2H); 4.04 (s, 3H); 2.46 (m, 1H); 2.25 (m, 1H); 1.23 (m, 4H); 0.94 (m, 2H); 0.57 (m, 2H);

Example No. 1-280

¹H-NMR (400 Mhz, DMSO-d$_6$): δ=11.91 (br s, 1H); 7.86 (d, 1H); 7.76 (d, 1H); 4.00 (s, 3H); 3.13 (m, 1H); 1.19 (d, 6H);

Example No. 1-281

¹H-NMR (400 Mhz, DMSO-d$_6$): δ=11.90 (br s, 1H); 7.85 (d, 1H); 7.75 (d, 1H); 3.99 (s, 3H); 3.39 (q, 2H); 1.89 (m, 4H); 1.65 (m, 4H);

Example No. 1-282

¹H-NMR (400 Mhz, DMSO-d$_6$): δ=11.94 (br s, 1H); 8.27 (d, 1H); 7.95 (d, 1H); 7.83 (d, 1H); 7.56 (m, 1H); 7.31 (m, 1H); 4.00 (s, 3H);

Example No. 1-283

¹H-NMR (400 Mhz, DMSO-d$_6$): δ=11.95 (br s, 1H); 7.92 (d, 1H); 7.81 (d, 2H); 7.76 (d, 2H); 7.13 (d, 2H); 4.00 (s, 3H); 3.88 (s, 3H);

Example No. 1-284

¹H-NMR (400 Mhz, DMSO-d$_6$): δ=11.84 (br s, 1H); 8.02 (d, 1H); 7.95 (d, 1H); 4.05 (s, 3H); 3.73 (m, 1H); 2.32 (s, 3H); 2.32 (m, 2H); 2.17 (m, 2H); 1.97 (m, 1H); 1.82 (m, 1H);

Example No. 1-285

¹H-NMR (400 Mhz, DMSO-d$_6$): δ=11.85 (br s, 1H); 8.04 (d, 1H); 7.96 (d, 1H); 4.05 (s, 3H); 3.34 (m, 1H); 2.32 (s, 3H); 1.92 (m, 2H); 1.79 (m, 2H); 1.68 (m, 2H); 1.58 (m, 2H);

Example No. 1-286

¹H-NMR (400 Mhz, DMSO-d$_6$): δ=11.85 (br s, 1H); 8.04 (d, 1H); 7.96 (d, 1H); 4.05 (s, 3H); 2.77 (m, 1H); 2.30 (s, 3H); 1.94 (m, 2H); 1.77 (m, 2H); 1.65 (m, 1H); 1.29 (m, 4H); 1.14 (m, 1H);

Example No. 1-287

¹H-NMR (400 Mhz, DMSO-d$_6$): δ=12.01 (br s, 1H); 8.15 (m, 2H); 7.76 (m, 1H); 7.54 (m, 2H); 4.01 (s, 3H);

Example No. 1-289

¹H-NMR (400 Mhz, DMSO-d$_6$): δ=11.89 (br s, 1H); 7.89 (d, 1H); 7.77 (d, 1H); 3.99 (s, 3H); 2.59 (s, 3H);

Example No. 1-291

¹H-NMR (400 Mhz, DMSO-d$_6$): δ=11.89 (br s, 1H); 7.89 (d, 1H); 7.76 (d, 1H); 4.00 (s, 3H); 2.32 (m, 1H); 1.24 (m, 4H);

Example No. 1-292

¹H-NMR (400 Mhz, DMSO-d$_6$): δ=11.67 (br s, 1H); 7.72 (d, 1H); 7.57 (d, 1H); 3.89 (s, 3H); 2.57 (s, 3H); 2.29 (s, 3H);

Example No. 1-293

¹H-NMR (400 Mhz, DMSO-d$_6$): δ=11.64 (br s, 1H); 7.71 (d, 1H); 7.56 (d, 1H); 3.98 (s, 3H); 2.86 (q, 2H); 2.26 (s, 3H); 1.12 (t, 3H);

Example No. 1-294

¹H-NMR (400 Mhz, DMSO-d$_6$): δ=11.65 (br s, 1H); 7.70 (d, 1H); 7.56 (d, 1H); 3.97 (s, 3H); 2.30 (s, 3H); 2.29 (m, 1H); 1.17 (m, 4H);

Example No. 2-1

¹H-NMR (400 Mhz, DMSO-d$_6$): δ=11.38 (br s, 1H); 7.56 (d, 1H); 7.25 (d, 1H); 4.32 (q, 2H); 2.50 (s, 3H); 2.27 (s, 3H); 2.24 (s, 3H); 1.46 (t, 3H);

Example No. 2-7

¹H-NMR (400 Mhz, DMSO-d$_6$): δ=11.70 (br s, 1H); 7.97 (d, 1H); 7.92 (d, 1H); 4.36 (q, 2H); 3.22 (s, 3H); 2.59 (s, 3H); 2.35 (s, 3H); 1.47 (t, 3H);

Example No. 2-9

¹H-NMR (400 Mhz, DMSO-d$_6$): δ=11.72 (br s, 1H); 7.98 (d, 1H); 7.92 (d, 1H); 4.36 (q, 2H); 3.21 (s, 3H); 2.41 (s, 3H); 2.38 (m, 1H); 1.48 (t, 3H); 1.23 (m, 4H);

Example No. 2-14

¹H-NMR (400 Mhz, DMSO-d$_6$): δ=11.67 (br s, 1H); 7.88 (d, 1H); 7.83 (d, 1H); 4.36 (q, 2H); 2.57 (s, 3H); 2.34 (s, 3H); 1.47 (t, 3H);

Example No. 2-15

¹H-NMR (400 Mhz, DMSO-d$_6$): δ=11.67 (br s, 1H); 7.88 (d, 1H); 7.83 (d, 1H); 4.34 (q, 2H); 2.85 (q, 2H); 2.29 (s, 3H); 1.47 (t, 3H); 1.12 (t, 3H);

Example No. 2-16

¹H-NMR (400 Mhz, DMSO-d$_6$): δ=11.67 (br s, 1H); 7.88 (d, 1H); 7.83 (d, 1H); 4.35 (q, 2H); 2.83 (t, 2H); 2.30 (s, 3H); 1.67 (m, 2H); 1.47 (t, 3H); 0.96 (t, 3H);

Example No. 2-18

¹H-NMR (400 Mhz, DMSO-d$_6$): δ=11.68 (br s, 1H); 7.88 (d, 1H); 7.84 (d, 1H); 4.36 (q, 2H); 2.38 (s, 3H); 2.35 (m, 1H); 1.48 (t, 3H); 1.23 (m, 4H);

Example No. 2-22

¹H-NMR (400 Mhz, DMSO-d$_6$): δ=11.83 (br s, 1H); 7.97 (d, 1H); 7.89 (d, 1H); 4.97 (s, 3H); 2.33 (s, 3H);

Example No. 2-48

¹H-NMR (400 Mhz, DMSO-d$_6$): δ=11.65 (br s, 1H); 7.93 (d, 1H); 7.72 (d, 1H); 4.35 (q, 2H); 3.84 (s, 3H); 2.55 (s, 3H); 1.47 (t, 3H);

Example No. 2-50

¹H-NMR (400 Mhz, DMSO-d₆): δ=11.63 (br s, 1H); 7.94 (d, 1H); 7.74 (d, 1H); 4.35 (q, 2H); 3.84 (s, 3H); 2.37 (m, 1H); 1.48 (t, 3H); 1.18 (m, 4H);

Example No. 2-58

¹H-NMR (400 Mhz, CDCl₃): δ=10.85 (br s, 1H); 7.88 (d, 1H); 7.83 (d, 1H); 4.52 (q, 2H); 2.67 (s, 3H); 2.41 (s, 3H); 1.64 (t, 3H);

Example No. 2-60

¹H-NMR (400 Mhz, DMSO-d₆): δ=11.74 (br s, 1H); 8.03 (d, 1H); 7.94 (d, 1H); 4.43 (q, 2H); 2.37 (s, 3H); 2.36 (m, 1H); 1.49 (t, 3H); 1.24 (m, 4H);

Example No. 2-65

¹H-NMR (400 Mhz, DMSO-d₆): δ=11.68 (br s, 1H); 7.84 (m, 2H); 7.09 (t, 1H); 4.42 (q, 2H); 2.62 (s, 3H); 2.35 (s, 3H); 1.49 (t, 3H);

Example No. 2-67

¹H-NMR (400 Mhz, DMSO-d₆): δ=11.68 (br s, 1H); 7.86 (s, 2H); 6.97 (t, 1H); 4.43 (q, 2H); 2.36 (s, 3H); 2.36 (m, 1H); 1.49 (t, 3H); 1.26 (m, 2H); 1.20 (m, 2H);

Example No. 2-114

¹H-NMR (400 Mhz, DMSO-d₆): δ=11.80 (br s, 1H); 7.85 (d, 1H); 7.76 (d, 1H); 4.35 (q, 2H); 3.99; 2.60 (s, 3H); 1.46 (t, 3H);

Example No. 2-115

¹H-NMR (400 Mhz, DMSO-d₆): δ=11.80 (br s, 1H); 7.86 (d, 1H); 7.76 (d, 1H); 4.35 (q, 2H); 2.89 (q, 2H); 1.46 (t, 3H); 1.14 (t, 3H);

Example No. 2-116

¹H-NMR (400 Mhz, DMSO-d₆): δ=11.81 (br s, 1H); 7.85 (d, 1H); 7.76 (d, 1H); 4.36 (q, 2H); 2.34 (m, 1H); 1.47 (t, 3H); 1.23 (m, 4H);

Example No. 2-121

¹H-NMR (400 Mhz, DMSO-d₆): δ=11.69 (br s, 1H); 7.76 (d, 1H); 7.55 (d, 1H); 4.34 (q, 2H); 2.58 (s, 3H); 2.55 (s, 3H); 1.46 (t, 3H);

Example No. 2-123

¹H-NMR (400 Mhz, DMSO-d₆): δ=11.68 (br s, 1H); 7.75 (d, 1H); 7.52 (d, 1H); 4.35 (q, 2H); 2.57 (s, 3H); 2.28 (m, 1H); 1.46 (t, 3H); 1.20 (m, 4H);

Example No. 2-127

¹H-NMR (400 Mhz, DMSO-d₆): δ=11.95 (br s, 1H); 8.12 (m, 2H); 4.35 (q, 2H); 3.29 (s, 3H); 2.64 (s, 3H); 1.47 (t, 3H);

Example No. 2-129

¹H-NMR (400 Mhz, DMSO-d₆): δ=11.95 (br s, 1H); 8.11 (m, 2H); 4.38 (q, 2H); 3.27 (s, 3H); 2.40 (m, 1H); 1.48 (t, 3H); 1.26 (m, 4H);

Example No. 2-134

¹H-NMR (400 Mhz, DMSO-d₆): δ=11.66 (br s, 1H); 7.67 (d, 1H); 7.43 (d, 1H); 4.35 (q, 2H); 2.56 (s, 3H); 2.28 (s, 3H); 1.46 (t, 3H);

Example No. 2-135

¹H-NMR (400 Mhz, DMSO-d₆): δ=11.66 (br s, 1H); 7.67 (d, 1H); 7.43 (d, 1H); 4.34 (q, 2H); 2.86 (q, 2H); 2.25 (s, 3H); 1.46 (t, 3H); 1.12 (t, 3H);

Example No. 2-136

¹H-NMR (400 Mhz, DMSO-d₆): δ=11.67 (br s, 1H); 7.68 (d, 1H); 7.44 (d, 1H); 4.35 (q, 2H); 2.32 (m, 1H); 2.31 (s, 3H); 1.46 (t, 3H); 1.18 (m, 4H);

Example No. 2-137

¹H-NMR (400 Mhz, DMSO-d₆): δ=11.91 (br s, 1H); 8.05 (d, 1H); 8.02 (d, 1H); 4.37 (q, 2H); 2.62 (s, 3H); 1.47 (t, 3H);

Example No. 2-139

¹H-NMR (400 Mhz, DMSO-d₆): δ=11.93 (br s, 1H); 8.03 (m, 2H); 4.36 (q, 2H); 2.89 (m, 2H); 1.68 (m, 2H); 1.47 (t, 3H); 0.97 (t, 3H);

Example No. 2-140

¹H-NMR (400 Mhz, DMSO-d₆): δ=11.93 (br s, 1H); 8.03 (m, 2H); 4.37 (q, 2H); 3.07 (m, 1H); 1.47 (t, 3H); 1.17 (d, 6H);

Example No. 2-141

¹H-NMR (400 Mhz, DMSO-d₆): δ=11.91 (br s, 1H); 8.03 (m, 2H); 4.38 (q, 2H); 2.39 (m, 1H); 1.47 (t, 3H); 1.25 (m, 4H);

Example No. 2-143

¹H-NMR (400 Mhz, DMSO-d₆): δ=11.97 (br s, 1H); 8.05 (s, 2H); 4.37 (q, 2H); 1.47 (t, 3H); 1.25 (s, 9H);

Example No. 2-144

¹H-NMR (400 Mhz, DMSO-d₆): δ=11.96 (br s, 1H); 8.09 (d, 1H); 8.04 (d, 1H); 4.50 (s, 2H); 4.37 (q, 2H); 3.37 (s, 3H); 1.47 (t, 3H);

Example No. 2-145

¹H-NMR (400 Mhz, CDCl₃): δ=11.15 (br s, 1H); 7.95 (d, 1H); 7.81 (d, 1H); 4.64 (s, 2H); 4.51 (q, 2H); 1.63 (t, 3H);

Example No. 2-147

¹H-NMR (400 Mhz, DMSO-d₆): δ=11.95 (br s, 1H); 8.04 (s, 2H); 4.38 (q, 2H); 1.48 (t, 3H); 1.40 (d, 2H); 1.22 (s, 3H); 1.13 (d, 2H);

Example No. 2-148

$^1$H-NMR (400 Mhz, DMSO-$d_6$): δ=11.90 (br s, 1H); 8.02 (m, 2H); 4.38 (q, 2H); 2.14 (m, 1H); 1.64 (m, 1H); 1.49 (m, 1H); 1.48 (t, 3H); 1.16 (m, 1H); 1.16 (d, 3H);

Example No. 2-149

$^1$H-NMR (400 Mhz, DMSO-$d_6$): δ=11.91 (br s, 1H); 8.01 (m, 2H); 4.37 (q, 2H); 2.22 (m, 1H); 1.48 (t, 3H); 1.35 (m, 2H); 1.29 (s, 3H); 1.22 (s, 3H);

Example No. 2-150

$^1$H-NMR (400 Mhz, DMSO-$d_6$): δ=11.99 (br s, 1H); 8.03 (br s, 2H); 4.38 (q, 2H); 1.63 (m, 2H); 1.48 (t, 3H); 1.17 (s, 3H); 1.15 (s, 3H); 0.88 (m, 1H);

Example No. 2-153

$^1$H-NMR (400 Mhz, DMSO-$d_6$): δ=11.91 (br s, 1H); 8.02 (m, 2H); 4.37 (q, 2H); 3.75 (m, 1H); 2.31 (m, 2H); 2.20 (m, 2H); 1.99 (m, 1H); 1.83 (m, 1H); 1.47 (t, 3H);

Example No. 2-154

$^1$H-NMR (400 Mhz, DMSO-$d_6$): δ=11.92 (br s, 1H); 8.04 (m, 2H); 4.37 (q, 2H); 3.34 (m, 1H); 1.94 (m, 2H); 1.79 (m, 2H); 1.63 (m, 4H); 1.48 (t, 3H);

Example No. 2-155

$^1$H-NMR (400 Mhz, DMSO-$d_6$): δ=11.93 (br s, 1H); 8.04 (d, 1H); 8.01 (d, 1H); 4.36 (q, 2H); 2.77 (m, 1H); 1.95 (m, 2H); 1.78 (m, 2H); 1.65 (m, 1H); 1.47 (t, 3H); 1.30 (m, 4H); 1.15 (m, 1H);

Example No. 2-162

$^1$H-NMR (400 Mhz, DMSO-$d_6$): δ=12.03 (br s, 1H); 8.34 (d, 1H); 8.27 (d, 1H); 4.38 (q, 2H); 1.48 (t, 3H);

Example No. 2-163

$^1$H-NMR (400 Mhz, DMSO-$d_6$): δ=12.00 (br s, 1H); 8.24 (d, 1H); 8.17 (d, 1H); 7.00 (t, 1H); 4.37 (q, 2H); 1.48 (t, 3H);

Example No. 2-164

$^1$H-NMR (400 Mhz, DMSO-$d_6$): δ=11.85 (br s, 1H); 7.96 (d, 1H); 7.81 (d, 1H); 7.14 (t, 1H); 4.37 (q, 2H); 2.60 (3H); 1.47 (t, 3H);

Example No. 2-165

$^1$H-NMR (400 Mhz, DMSO-$d_6$): δ=11.88 (br s, 1H); 7.96 (d, 1H); 7.81 (d, 1H); 7.11 (t, 1H); 4.37 (q, 2H); 2.90 (q, 2H); 1.47 (t, 3H); 1.13 (t, 1H);

Example No. 2-168

$^1$H-NMR (400 Mhz, DMSO-$d_6$): δ=11.86 (br s, 1H); 7.97 (d, 1H); 7.82 (d, 1H); 7.05 (t, 1H); 4.37 (q, 2H); 2.38 (m, 1H); 1.47 (t, 3H); 1.24 (m, 4H);

Example No. 2-194

$^1$H-NMR (400 Mhz, DMSO-$d_6$): δ=11.78 (br s, 1H); 8.06 (d, 1H); 7.53 (d, 1H); 4.35 (q, 2H); 2.29 (m, 1H); 1.46 (t, 3H); 1.25 (m, 4H);

Example No. 2-195

$^1$H-NMR (400 Mhz, DMSO-$d_6$): δ=11.89 (br s, 1H); 8.05 (d, 1H); 7.99 (d, 1); 4.39 (q, 2H); 2.62 (s, 3H); 1.48 (t, 3H);

Example No. 2-197

$^1$H-NMR (400 Mhz, DMSO-$d_6$): δ=11.91 (br s, 1H); 8.07 (d, 1H); 8.00 (d, 1H); 4.41 (q, 2H); 2.38 (m, 1H); 1.50 (t, 3H); 1.29 (m, 4H);

Example No. 2-202

$^1$H-NMR (400 Mhz, DMSO-$d_6$): δ=11.83 (br s, 1H); 7.91 (d, 1H); 7.84 (d, 1H); 7.12 (t, 1H); 4.39 (q, 2H); 2.60 (s, 3H); 1.48 (t, 3H);

Example No. 2-204

$^1$H-NMR (400 Mhz, DMSO-$d_6$): δ=11.86 (br s, 1H); 7.91 (d, 1H); 7.86 (d, 1H); 7.03 (t, 1H); 4.39 (q, 2H); 2.37 (m, 1H); 1.48 (t, 3H); 1.25 (m, 4H);

Example No. 2-231

$^1$H-NMR (400 Mhz, DMSO-$d_6$): δ=11.60 (br s, 1H); 7.84 (m, 2H); 4.38 (q, 2H); 2.64 (s, 3H); 2.28 (m, 1H); 1.50 (t, 3H); 0.94 (m, 2H); 0.55 (m, 2H);

Example No. 2-233

$^1$H-NMR (400 Mhz, DMSO-$d_6$): δ=11.60 (br s, 1H); 7.84 (m, 2H); 4.38 (q, 2H); 2.44 (m, 1H); 2.23 (m, 1H); 1.50 (t, 3H); 1.22 (m, 4H); 0.94 (m, 2H); 0.57 (m, 2H);

Example No. 2-280

$^1$H-NMR (400 Mhz, DMSO-$d_6$): δ=11.81 (br s, 1H); 7.86 (d, 1H); 7.76 (d, 1H); 4.35 (q, 2H); 3.13 (m, 1H); 1.47 (t, 3H); 1.19 (d, 6H);

Example No. 2-281

$^1$H-NMR (400 Mhz, DMSO-$d_6$): δ=11.80 (br s, 1H); 7.85 (d, 1H); 7.75 (d, 1H); 4.35 (q, 2H); 3.39 (m, 1H); 1.88 (m, 4H); 1.64 (m, 4H); 1.46 (t, 3H);

Example No. 2-282

$^1$H-NMR (400 Mhz, DMSO-$d_6$): δ=11.85 (br s, 1H); 8.27 (d, 1H); 7.95 (d, 1H); 7.83 (d, 1H); 7.57 (m, 1H); 7.31 (m, 1H); 4.36 (q, 2H); 1.46 (t, 3H);

Example No. 2-283

$^1$H-NMR (400 Mhz, DMSO-$d_6$): δ=11.84 (br s, 1H); 7.92 (d, 1H); 7.81 (d, 1H); 7.76 (d, 2H); 7.13 (d, 2H); 4.35 (q, 2H); 3.88 (s, 3H); 1.46 (t, 3H);

Example No. 2-284

¹H-NMR (400 Mhz, DMSO-d₆): δ=11.73 (br s, 1H); 8.02 (d, 1H); 7.93 (d, 1H); 4.42 (q, 2H); 3.73 (m, 1H); 2.33 (s, 3H); 2.32 (m, 2H); 2.18 (m, 2H); 1.97 (m, 1H); 1.82 (m, 1H); 1.48 (t, 3H);

Example No. 2-285

¹H-NMR (400 Mhz, DMSO-d₆): δ=11.77 (br s, 1H); 8.04 (d, 1H); 7.95 (d, 1H); 4.44 (q, 2H); 2.78 (m, 1H); 2.32 (s, 3H); 1.95 (m, 2H); 1.79 (m, 2H); 1.65 (m, 1H); 1.50 (t, 3H); 1.28 (m, 4H); 1.16 (m, 1H);

Example No. 2-286

¹H-NMR (400 Mhz, DMSO-d₆): δ=11.93 (br s, 1H); 8.15 (m, 2H); 7.76 (m, 1H); 7.54 (m, 2H); 4.36 (q, 2H); 1.46 (t, 3H);

Example No. 2-288

¹H-NMR (400 Mhz, DMSO-d₆): δ=11.79 (br s, 1H); 7.89 (d, 1H); 7.76 (d, 1H); 4.35 (q, 2H); 2.59 (s, 3H); 1.46 (t, 3H);

Example No. 2-290

¹H-NMR (400 Mhz, DMSO-d₆): δ=11.80 (br s, 1H); 7.89 (d, 1H); 7.75 (d, 1H); 4.35 (q, 2H); 2.32 (m, 1H); 1.46 (t, 3H); 1.24 (m, 4H);

Example No. 2-291

¹H-NMR (400 Mhz, DMSO-d₆): δ=11.57 (br s, 1H); 7.71 (d, 1H); 7.57 (d, 1H); 4.33 (q, 2H); 2.57 (s, 3H); 2.29 (s, 3H); 1.46 (t, 3H);

Example No. 2-292

¹H-NMR (400 Mhz, DMSO-d₆): δ=11.53 (br s, 1H); 7.71 (d, 1H); 7.56 (d, 1H); 4.33 (q, 2H); 2.86 (q, 2H); 2.26 (s, 3H); 1.46 (t, 3H); 1.12 (t, 3H);

Example No. 2-293

¹H-NMR (400 Mhz, DMSO-d₆): δ=11.54 (br s, 1H); 7.71 (d, 1H); 7.57 (d, 1H); 4.33 (q, 2H); 2.31 (s, 3H); 2.31 (m, 1H); 1.46 (t, 3H); 1.19 (m, 4H);

Example No. 2-294

¹H-NMR (400 Mhz, DMSO-d₆): δ=11.92 (br s, 1H); 8.07 (m, 2H); 6.74 (dd, 1H); 6.45 (d, 1H); 6.00 (d, 1H); 4.37 (q, 2H); 1.47 (t, 3H);

Example No. 3-1

¹H-NMR (400 Mhz, DMSO-d₆): δ=11.36 (br s, 1H); 7.55 (d, 1H); 7.26 (d, 1H); 4.27 (t, 2H); 2.51 (s, 3H); 2.26 (s, 3H); 2.24 (s, 3H); 1.88 (m, 2H); 0.87 (t, 3H);

Example No. 3-3

¹H-NMR (400 Mhz, DMSO-d₆): δ=11.37 (br s, 1H); 7.56 (d, 1H); 7.28 (d, 1H); 4.28 (t, 2H); 2.30 (s, 3H); 2.28 (m, 1H); 2.27 (s, 3H); 1.16 (m, 4H); 0.87 (t, 3H);

Example No. 3-7

¹H-NMR (400 Mhz, DMSO-d₆): δ=11.68 (br s, 1H); 7.97 (d, 1H); 7.91 (d, 1H); 4.30 (t, 2H); 3.22 (s, 3H); 2.59 (s, 3H); 2.35 (s, 3H); 1.89 (m, 2H); 0.89 (t, 3H);

Example No. 3-9

¹H-NMR (400 Mhz, DMSO-d₆): δ=11.70 (br s, 1H); 7.98 (d, 1H); 7.91 (d, 1H); 4.31 (t, 2H); 3.21 (s, 3H); 2.41 (s, 3H); 2.36 (m, 1H); 1.89 (m, 2H); 1.23 (m, 4H); 0.89 (t, 3H);

Example No. 3-14

¹H-NMR (400 Mhz, DMSO-d₆): δ=11.64 (br s, 1H); 7.86 (d, 1H); 7.83 (d, 1H); 4.30 (t, 2H); 2.57 (s, 3H); 2.33 (s, 3H); 1.89 (m, 2H); 0.89 (t, 3H);

Example No. 3-15

¹H-NMR (400 Mhz, DMSO-d₆): δ=11.64 (br s, 1H); 7.87 (d, 1H); 7.83 (d, 1H); 4.30 (t, 2H); 2.85 (q, 2H); 2.29 (s, 3H); 1.89 (m, 2H); 1.12 (t, 3H); 0.89 (s, 3H);

Example No. 3-16

¹H-NMR (400 Mhz, DMSO-d₆): δ=11.65 (br s, 1H); 7.86 (d, 1H); 7.83 (d, 1H); 4.30 (t, 2H); 2.83 (t, 2H); 2.30 (s, 3H); 1.89 (m, 2H); 1.66 (m, 2H); 0.96 (t, 3H); 0.89 (t, 3H);

Example No. 3-18

¹H-NMR (400 Mhz, CDCl₃): δ=11.00 (br s, 1H); 7.85 (d, 1H); 7.68 (d, 1H); 4.39 (q, 2H); 2.49 (s, 3H); 2.25 (m, 1H); 2.01 (m, 2H); 1.42 (m, 2H); 1.21 (m, 2H); 0.98 (t, 3H);

Example No. 3-48

¹H-NMR (400 Mhz, DMSO-d₆): δ=11.66 (br s, 1H); 7.92 (d, 1H); 7.72 (d, 1H); 4.30 (t, 2H); 3.84 (s, 3H); 2.55 (s, 3H); 1.89 (m, 2H); 0.89 (t, 3H);

Example No. 3-50

¹H-NMR (400 Mhz, DMSO-d₆): δ=11.60 (br s, 1H); 7.93 (d, 1H); 7.74 (d, 1H); 4.30 (t, 2H); 3.84 (s, 3H); 2.37 (m, 1H); 1.89 (m, 2H); 1.18 (m, 4H); 0.89 (t, 3H);

Example No. 3-58

¹H-NMR (400 Mhz, CDCl₃): δ=10.83 (br s, 1H); 7.86 (d, 1H); 7.82 (d, 1H); 4.45 (t, 2H); 2.67 (s, 3H); 2.40 (s, 3H); 2.05 (m, 2H); 1.00 (t, 3H);

Example No. 3-65

¹H-NMR (400 Mhz, DMSO-d₆): δ=11.68 (br s, 1H); 7.84 (s, 2H); 7.09 (t, 1H); 4.37 (t, 2H); 2.62 (3H); 2.35 (s, 3H); 1.91 (2H); 0.90 (t, 3H);

Example No. 3-67

¹H-NMR (400 Mhz, DMSO-d₆): δ=11.68 (br s, 1H); 7.85 (s, 2H); 6.97 (t, 1H); 4.37 (t, 2H); 2.38 (m, 1H); 2.36 (s, 3H); 1.91 (m, 2H); 1.23 (m, 4H); 0.90 (t, 3H);

Example No. 3-123

¹H-NMR (400 Mhz, DMSO-d₆): δ=11.66 (br. s, 1H); 7.74 (d, 1H); 7.52 (d, 1H); 4.30 (t, 2H); 2.57 (s, 3H); 2.28 (m, 1H); 1.88 (m, 2H); 1.19 (m, 4H); 0.87 (t, 3H);

Example No. 3-129

¹H-NMR (400 Mhz, DMSO-d₆): δ=11.93 (br s, 1H); 8.12 (d, 1H); 8.08 (d, 1H); 4.32 (t, 2H); 3.27 (s, 3H); 2.40 (m, 1H); 1.89 (m, 2H); 1.26 (m, 4H); 0.88 (t, 3H);

Example No. 3-134

¹H-NMR (400 Mhz, DMSO-d₆): δ=11.65 (br s, 1H); 7.66 (d, 1H); 7.43 (d, 1H); 4.30 (t, 2H); 2.56 (s, 3H); 2.28 (s, 3H); 1.88 (m, 2H); 0.87 (t, 3H);

Example No. 3-135

¹H-NMR (400 Mhz, DMSO-d₆): δ=11.65 (br s, 1H); 7.66 (d, 1H); 7.43 (d, 1H); 4.29 (t, 2H); 2.86 (q, 2H); 2.25 (s, 3H); 1.88 (m, 2H); 1.12 (t, 3H); 0.87 (t, 3H);

Example No. 3-136

¹H-NMR (400 Mhz, DMSO-d₆): δ=11.65 (br s, 1H); 7.66 (d, 1H); 7.44 (d, 1H); 4.30 (t, 2H); 2.32 (m, 1H); 2.30 (s, 3H); 1.88 (m, 2H); 1.19 (m, 4H); 0.87 (t, 3H);

Example No. 3-137

¹H-NMR (400 Mhz, DMSO-d₆): δ=11.89 (br s, 1H); 8.02 (m, 2H); 4.32 (t, 2H); 2.62 (s, 3H); 1.89 (m, 2H); 0.88 (t, 3H);

Example No. 3-140

¹H-NMR (400 Mhz, DMSO-d₆): δ=11.91 (br s, 1H); 8.04 (s, 2H); 4.32 (t, 2H); 3.07 (m, 1H); 1.89 (m, 2H); 1.17 (d, 6H); 0.88 (t, 3H);

Example No. 3-141

¹H-NMR (400 Mhz, DMSO-d₆): δ=11.89 (br s, 1H); 8.03 (m, 2H); 4.32 (t, 2H); 2.40 (m, 1H); 1.89 (m, 2H); 1.25 (m, 4H); 0.88 (t, 3H);

Example No. 3-144

¹H-NMR (400 Mhz, DMSO-d₆): δ=11.94 (br s, 1H); 8.05 (m, 2H); 4.50 (s, 2H); 4.32 (t, 2H); 3.37 (s, 3H); 1.88 (m, 2H); 0.88 (t, 3H);

Example No. 3-150

¹H-NMR (400 Mhz, DMSO-d₆): δ=11.93 (br s, 1H); 8.02 (br s, 2H); 4.33 (t, 2H); 1.91.89 (m, 2H); 1.63 (m, 2H); 1.17 (s, 3H); 1.15 (s, 3H); 0.88 (t, 3H); 0.87 (m, 1H);

Example No. 3-153

¹H-NMR (400 Mhz, DMSO-d₆): δ=11.91 (br s, 1H); 8.03 (m, 2H); 4.33 (t, 2H); 3.77 (m, 1H); 2.34 (m, 2H); 2.21 (m, 2H); 2.01 (m, 1H); 1.88 (m, 3H); 0.90 (t, 3H);

Example No. 3-155

¹H-NMR (400 Mhz, DMSO-d₆): δ=11.90 (br s, 1H); 8.03 (br s, 2H); 4.32 (t, 2H); 2.77 (m, 1H); 1.94 (m, 4H); 1.99 (m, 2H); 1.78 (m, 2H); 1.65 (m, 1H); 1.29 (m, 2H); 1.15 (m, 1H); 0.88 (t, 3H);

Example No. 3-163

¹H-NMR (400 Mhz, DMSO-d₆): δ=11.98 (br s, 1H); 8.23 (d, 1H); 8.17 (d, 1H); 7.01 (t, 1H); 4.32 (t, 2H); 1.89 (m, 2H); 0.89 (t, 3H);

Example No. 3-164

¹H-NMR (400 Mhz, DMSO-d₆): δ=11.83 (br s, 1H); 7.95 (d, 1H); 7.81 (d, 1H); 7.14 (t, 1H); 4.32 (t, 2H); 2.60 (s, 3H); 1.89 (m, 2H); 0.88 (t, 3H);

Example No. 3-165

¹H-NMR (400 Mhz, DMSO-d₆): δ=11.86 (br s, 1H); 7.95 (d, 1H); 7.81 (d, 1H); 7.11 (t, 1H); 4.31 (t, 2H); 2.90 (q, 2H); 1.89 (m, 2H); 1.13 (t, 3H); 0.88 (t, 3H);

Example No. 3-168

¹H-NMR (400 Mhz, DMSO-d₆): δ=11.84 (br s, 1H); 7.95 (d, 1H); 7.83 (d, 1H); 7.05 (t, 1H); 4.32 (t, 2H); 2.38 (m, 1H); 1.89 (m, 2H); 1.24 (m, 4H); 0.88 (t, 3H);

Example No. 3-192

¹H-NMR (400 Mhz, DMSO-d₆): δ=11.75 (br s, 1H); 8.06 (d, 1H); 7.53 (d, 1H); 4.29 (t, 2H); 2.58 (s, 3H); 1.87 (m, 2H); 0.87 (t, 3H);

Example No. 3-195

¹H-NMR (400 Mhz, DMSO-d₆): δ=11.87 (br s, 1H); 8.05 (d, 1H); 7.98 (d, 1H); 4.34 (t, 2H); 2.62 (s, 3H); 1.90 (m, 2H); 0.89 (t, 3H);

Example No. 3-197

¹H-NMR (400 Mhz, DMSO-d₆): δ=11.89 (br s, 1H); 8.07 (d, 1H); 7.99 (d, 1H); 4.35 (t, 2H); 2.38 (m, 1H); 1.93 (m, 2H); 1.29 (m, 4H); 0.91 (t, 3H);

Example No. 3-202

¹H-NMR (400 Mhz, DMSO-d₆): δ=11.82 (br s, 1H); 7.89 (d, 1H); 7.84 (d, 1H); 4.33 (t, 2H); 2.60 (s, 3H); 1.90 (m, 2H); 0.89 (t, 3H);

Example No. 3-204

¹H-NMR (400 Mhz, DMSO-d₆): δ=11.81 (br s, 1H); 7.89 (d, 1H); 7.85 (d, 1H); 7.02 (t, 1H); 4.33 (t, 2H); 2.36 (m, 1H); 1.89 (m, 2H); 1.26 (m, 4H); 0.89 (t, 3H);

Example No. 3-231

¹H-NMR (400 Mhz, DMSO-d₆): δ=11.58 (br s, 1H); 7.85 (d, 1H); 7.80 (d, 1H); 4.33 (t, 2H); 2.64 (s, 3H); 2.27 (m, 1H); 1.91 (m, 2H); 0.94 (m, 2H); 0.90 (t, 3H); 0.55 (m, 2H);

Example No. 3-280

¹H-NMR (400 Mhz, DMSO-$d_6$): δ=11.73 (br s, 1H); 8.02 (d, 1H); 7.92 (d, 1H); 4.36 (t, 2H); 3.74 (m, 1H); 2.33 (s, 3H); 2.33 (m, 2H); 2.18 (m, 2H); 1.94 (m, 3H); 1.83 (m, 1H); 0.89 (t, 3H);

Example No. 3-281

¹H-NMR (400 Mhz, DMSO-$d_6$): δ=11.74 (br s, 1H); 8.04 (d, 1H); 7.94 (d, 1H); 4.37 (t, 2H); 2.77 (m, 1H); 2.32 (s, 3H); 1.94 (m, 2H); 1.92 (m, 2H); 1.77 (m, 2H); 1.65 (m, 1H); 1.26 (m, 4H); 1.14 (m, 1H); 0.90 (s, 3H);

Example No. 3-282

¹H-NMR (400 Mhz, DMSO-$d_6$): δ=11.91 (br s, 1H); 8.15 (m, 2H); 7.77 (m, 1H); 7.54 (m, 2H); 4.31 (t, 2H); 1.88 (m, 2H); 0.87 (t, 3H).

Example No. 3-284

¹H-NMR (400 Mhz, DMSO-$d_6$): δ=11.78 (br s, 1H); 7.89 (d, 1H); 7.75 (d, 1H); 4.30 (t, 2H); 2.59 (s, 3H); 1.88 (m, 2H); 0.87 (t, 3H);

Example No. 3-286

¹H-NMR (400 Mhz, DMSO-$d_6$): δ=11.78 (br s, 1H); 7.89 (d, 1H); 7.74 (d, 1H); 4.30 (t, 2H); 2.32 (m, 1H); 1.88 (m, 2H); 1.24 (m, 4H); 0.87 (t, 3H);

Example No. 3-287

¹H-NMR (400 Mhz, DMSO-$d_6$): δ=11.54 (br s, 1H); 7.70 (d, 1H); 7.57 (d, 1H); 4.28 (t, 2H); 2.57 (s, 3H); 2.29 (s, 3H); 1.87 (m, 2H); 0.88 (t, 3H);

Example No. 3-288

¹H-NMR (400 Mhz, DMSO-$d_6$): δ=11.51 (br s, 1H); 7.69 (d, 1H); 7.56 (d, 1H); 4.28 (t, 2H); 2.86 (q, 2H); 2.26 (s, 3H); 1.88 (m, 2H); 1.12 (t, 3H); 0.88 (t, 3H);

Example No. 3-289

¹H-NMR (400 Mhz, DMSO-$d_6$): δ=11.52 (br s, 1H); 7.69 (d, 1H); 7.58 (d, 1H); 4.29 (t, 2H); 2.31 (s, 3H); 2.31 (m, 1H); 1.88 (m, 2H); 2.20 (m, 4H); 0.88 (t, 3H);

Example No. 4-2

¹H-NMR (400 Mhz, DMSO-$d_6$): δ=7.95 (d, 1H); 7.77 (d, 1H); 3.89 (s, 3H); 2.83 (q, 2H); 2.34 (s, 3H); 1.10 (t, 3H);

Example No. 4-3

¹H-NMR (400 Mhz, DMSO-$d_6$): δ=7.94 (d, 1H); 7.77 (d, 1H); 3.89 (s, 3H); 2.80 (t, 2H); 2.34 (s, 3H); 1.65 (m, 2H); 0.95 (t, 3H);

Example No. 4-5

¹H-NMR (400 Mhz, DMSO-$d_6$): δ=7.95 (d, 1H); 7.78 (d, 1H); 3.89 (s, 3H); 3.32 (s, 3H); 2.42 (s, 3H); 2.35 (m, 1H); 1.21 (m, 4H);

Example No. 4-8

¹H-NMR (400 Mhz, DMSO-$d_6$): δ=7.97 (d, 1H); 7.79 (d, 1H); 4.43 (s, 2H); 3.89 (s, 3H); 3.34 (s, 3H); 2.37 (s, 3H);

Example No. 4-9

¹H-NMR (400 Mhz, DMSO-$d_6$): δ=8.01 (d, 1H); 7.83 (d, 1H); 4.95 (s, 3H); 3.90 (s, 3H); 2.37 (s, 3H);

Example No. 4-35

¹H-NMR (400 Mhz, DMSO-$d_6$): δ=7.98 (d, 1H); 7.67 (d, 1H); 3.92 (s, 3H); 3.78 (s, 3H); 2.51 (s, 3H);

Example No. 4-37

¹H-NMR (400 Mhz, DMSO-$d_6$): δ=7.98 (d, 1H); 7.68 (d, 1H); 3.92 (s, 3H); 3.78 (s, 3H); 2.35 (m, 1H); 1.15 (m, 4H);

Example No. 4-45

¹H-NMR (400 Mhz, DMSO-$d_6$): δ=7.97 (d, 1H); 7.87 (d, 1H); 3.92 (s, 3H); 2.60 (s, 3H); 2.33 (s, 3H);

Example No. 4-49

¹H-NMR (400 Mhz, DMSO-$d_6$): δ=7.97 (m, 1H); 7.86 (d, 1H); 3.92 (s, 3H); 2.38 (m, 1H); 2.34 (s, 3H); 1.21 (m, 4H);

Example No. 4-61

¹H-NMR (400 Mhz, DMSO-$d_6$): δ=7.95 (d, 1H); 7.86 (d, 1H); 3.91 (s, 3H); 3.71 (m, 1H); 2.31 (m, 2H); 2.31 (s, 3H); 2.16 (m, 2H); 1.94 (m, 1H); 1.80 (m, 1H);

Example No. 4-62

¹H-NMR (400 Mhz, DMSO-$d_6$): δ=7.97 (d, 1H); 7.86 (d, 1H); 3.91 (s, 3H); 3.31 (m, 1H); 2.29 (s, 3H); 1.90 (m, 2H); 1.75 (m, 2H); 1.66 (m, 2H); 1.56 (m, 2H);

Example No. 4-63

¹H-NMR (400 Mhz, DMSO-$d_6$): δ=7.98 (d, 1H); 7.86 (d, 1H); 3.91 (s, 3H); 2.73 (m, 1H); 2.28 (s, 3H); 1.91 (m, 2H); 1.75 (m, 2H); 1.63 (m, 1H); 1.24 (m, 4H); 1.11 (m, 1H);

Example No. 4-74

¹H-NMR (400 Mhz, CDCl$_3$): δ=7.69 (br s, 2H); 6.64 (t, 1H); 3.97 (s, 3H); 2.37 (s, 3H); 2.32 (m, 1H); 1.42 (m, 2H); 1.18 (m, 2H);

Example No. 4-99

¹H-NMR (400 Mhz, DMSO-$d_6$): δ=8.04 (d, 1H); 7.77 (d, 1H); 3.92 (s, 3H); 3.60 (s, 3H);

Example No. 4-100

¹H-NMR (400 Mhz, DMSO-$d_6$): δ=8.05 (d, 1H); 7.97 (d, 1H); 3.92 (s, 3H); 2.89 (q, 2H); 1.12 (t, 3H);

Example No. 4-101

¹H-NMR (400 Mhz, CDCl$_3$): δ=7.87 (d, 1H); 7.65 (d, 1H); 3.97 (s, 3H); 2.83 (t, 2H); 1.68 (m, 2H); 1.02 (t, 3H);

Example No. 4-102

¹H-NMR (400 Mhz, CDCl₃): δ=7.86 (d, 1H); 7.66 (d, 1H); 3.97 (s, 1H); 3.05 (m, 1H); 1.24 (d, 6H);

Example No. 4-103

¹H-NMR (400 Mhz, DMSO-d₆): δ=8.04 (d, 1H); 7.97 (d, 1H); 3.92 (s, 3H); 2.41 (m, 1H); 1.23 (m, 4H);

Example No. 4-105

¹H-NMR (400 Mhz, CDCl₃): δ=7.83 (d, 1H); 7.66 (d, 1H); 3.97 (s, 3H); 1.30 (s, 9H);

Example No. 4-106

¹H-NMR (400 Mhz, CDCl₃): δ=7.93 (d, 1H); 7.67 (d, 1H); 4.42 (s, 2H); 3.98 (s, 3H); 3.47 (s, 3H);

Example No. 4-107

¹H-NMR (400 Mhz, CDCl₃): δ=7.98 (d, 1H); 7.71 (d, 1H); 4.54 (s, 2H); 3.99 (s, 3H);

Example No. 4-108

¹H-NMR (400 Mhz, DMSO-d₆): δ=8.19 (d, 1H); 8.06 (d, 1H); 3.92 (s, 3H); 2.58 (s, 3H);

Example No. 4-109

¹H-NMR (400 Mhz, DMSO-d₆): δ=8.05 (d, 1H); 7.99 (d, 1H); 3.92 (s, 3H); 1.39 (m, 2H); 1.18 (s, 3H); 1.12 (m, 2H);

Example No. 4-110

¹H-NMR (400 Mhz, DMSO-d₆): δ=8.03 (d, 1H); 7.96 (d, 1H); 3.92 (s, 3H); 2.18 (m, 1H); 1.511 (m, 1H); 1.49 (m, 1H); 1.14 (d, 3H); 1.14 (m, 1H);

Example No. 4-111

¹H-NMR (400 Mhz, DMSO-d₆): δ=8.01 (d, 1H); 7.94 (d, 1H); 3.92 (s, 3H); 2.26 (m, 1H); 1.31 (m, 2H); 1.28 (s, 3H); 1.20 (s, 3H);

Example No. 4-112

¹H-NMR (400 Mhz, DMSO-d₆): δ=8.04 (d, 2H); 7.98 (2×d, 2H); 3.92 (6H); 1.63 (m, 4H); 1.15 (m, 7H); 0.86 (m, 1H);

Example No. 4-115

¹H-NMR (400 Mhz, DMSO-d₆): δ=8.03 (d, 1H); 7.96 (d, 1H); 3.92 (s, 3H); 3.75 (m, 1H); 2.31 (m, 2H); 1.17 (m, 2H); 1.97 (m, 1H); 1.81 (m, 1H);

Example No. 4-116

¹H-NMR (400 Mhz, DMSO-d₆): δ=8.04 (d, 1H); 7.97 (d, 1H); 3.92 (s, 3H); 3.32 (m, 1H); 1.92 (m, 2H); 1.76 (m, 2H); 1.62 (m, 4H);

Example No. 4-117

¹H-NMR (400 Mhz, DMSO-d₆): δ=8.04 (d, 1H); 7.98 (d, 1H); 3.92 (s, 3H); 2.75 (m, 1H); 1.92 (m, 2H); 1.76 (m, 2H); 1.63 (m, 1H); 1.29 (m, 4H); 1.15 (m, 1H);

Example No. 4-124

¹H-NMR (400 Mhz, CDCl₃): δ=8.09 (d, 1H); 7.75 (d, 1H); 4.00 (s, 3H);

Example No. 4-125

¹H-NMR (400 Mhz, CDCl₃): δ=8.24 (d, 1H); 8.12 (d, 1H); 6.99 (t, 1H); 3.95 (s, 3H);

Example No. 4-126

¹H-NMR (400 Mhz, DMSO-d₆): δ=7.98 (d, 1H); 7.77 (d, 1H); 7.11 (t, 1H); 3.91 (s, 3H); 2.58 (s, 3H);

Example No. 4-127

¹H-NMR (400 Mhz, DMSO-d₆): δ=7.98 (d, 1H); 7.76 (d, 1H); 7.08 (t, 1H); 3.90 (s, 3H); 2.87 (q, 2H); 1.11 (t, 3H);

Example No. 4-130

¹H-NMR (400 Mhz, CDCl₃): δ=7.88 (d, 1H); 7.64 (d, 1H); 6.68 (t, 1H); 3.97 (s, 3H); 2.33 (m, 1H); 1.42 (m, 2H); 1.20 (m, 2H);

Example No. 4-153

¹H-NMR (400 Mhz, DMSO-d₆): δ=8.00 (d, 1H); 7.96 (d, 1H); 3.92 (s, 3H); 2.60 (s, 3H);

Example No. 4-155

¹H-NMR (400 Mhz, DMSO-d₆): δ=8.00 (d, 1H); 7.95 (d, 1H); 3.92 (s, 3H); 2.39 (m, 1H); 1.25 (m, 4H);

Example No. 4-160

¹H-NMR (400 Mhz, DMSO-d₆): δ=7.90 (d, 1H); 7.80 (d, 1H); 7.09 (t, 1H); 3.91 (s, 3H); 2.58 (s, 3H);

Example No. 4-161

¹H-NMR (400 Mhz, DMSO-d₆): δ=7.90 (d, 1H); 7.80 (d, 1H); 7.06 (t, 1H); 3.90 (s, 6H); 2.87 (q, 2H); 1.13 (t, 3H);

Example No. 4-162

¹H-NMR (400 Mhz, DMSO-d₆): δ=7.90 (d, 1H); 7.81 (d, 1H); 3.91 (s, 3H); 2.37 (m, 1H); 1.23 (m, 4H);

Example No. 4-187

¹H-NMR (400 Mhz, DMSO-d₆): δ=7.79 (d, 1h); 7.76 (d, 1H); 3.90 (s, 3H); 2.63 (s, 3H); 2.21 (m, 1H); 0.92 (m, 2H); 0.38 (m, 1H);

Example No. 4-189

¹H-NMR (400 Mhz, DMSO-d₆): δ=7.79 (d, 1H); 7.75 (d, 1H); 3.90 (s, 3H); 2.46 (m, 1H); 2.15 (m, 1H); 1.20 (m, 4H); 0.92 (m, 2H); 0.41 (m, 2H);

Example No. 4-201

$^1$H-NMR (400 Mhz, DMSO-d$_6$): δ=8.19 (d, 1H); 8.08 (d, 1H); 7.73 (m, 1H); 7.58 (m, 2H); 3.92 (s, 3H);

Example No. 4-203

$^1$H-NMR (400 Mhz, DMSO-d$_6$): δ=8.09 (d, 1H); 8.01 (d, 1H); 6.72 (dd, 1H); 6.39 (d, 1H); 6.00 (d, 1H); 3.92 (s, 3H);

Example No. 4-204

$^1$H-NMR (400 Mhz, DMSO-d$_6$): δ=8.08 (d, 1H); 7.99 (d, 1H); 6.27 (s, 1H); 5.59 (s, 1H); 3.92 (s, 3H); 1.97 (s, 3);

Example No. 4-205

$^1$H-NMR (400 Mhz, DMSO-d$_6$): δ=8.06 (m, 2H); 7.97 (m, 2H); 6.61 (2×d, 2H); 6.48 (2×d, 2H); 3.92 (2×s, 6H); 2.03 (d, 3H); 1.93 (d, 3H);

Example No. 4-206

$^1$H-NMR (400 Mhz, DMSO-d$_6$): δ=8.01 (4×d, 4H); 6.53 (br q, 1H); 6.35 (q, 1H); 3.92 (s, 3H); 3.91 (s, 3H); 1.86 (m, 6H);

Example No. 4-207

$^1$H-NMR (400 Mhz, DMSO-d$_6$): δ=8.01 (d, 1H); 7.94 (d, 1H); 6.35 (br s, 1H); 3.91 (s, 3H); 2.14 (s, 3H); 1.98 (s, 3H);

Example No. 4-213

$^1$H-NMR (400 Mhz, DMSO-d$_6$): δ=8.14 (d, 1H); 8.04 (d, 1H); 5.54 (s, 1H); 3.93 (s, 3H);

Example No. 4-214

$^1$H-NMR (400 Mhz, DMSO-d$_6$): δ=8.09 (d, 1H); 8.01 (d, 1H); 3.93 (s, 3H); 2.18 (s, 3H);

Example No. 5-2

$^1$H-NMR (400 Mhz, DMSO-d$_6$): δ=13.61 (br s, 1H); 7.93 (d, 1H); 7.74 (d, 1H); 2.82 (q, 2H); 2.34 (s, 3H); 1.10 (t, 3H);

Example No. 5-3

$^1$H-NMR (400 Mhz, DMSO-d$_6$): δ=13.60 (br s, 1H); 7.92 (d, 1H); 7.74 (d, 1H); 2.80 (t, 2H); 2.36 (s, 3H); 1.64 (m, 2H); 0.95 (t, 3H);

Example No. 5-5

$^1$H-NMR (400 Mhz, DMSO-d$_6$): δ=13.59 (br s, 1H); 7.93 (d, 1H); 7.75 (d, 1H); 2.37 (s, 3H); 2.34 (m, 1H); 1.20 (m, 4H);

Example No. 5-8

$^1$H-NMR (400 Mhz, DMSO-d$_6$): δ=13.61 (br s, 1H); 7.95 (d, 1H); 7.74 (d, 1H); 4.42 (s, 2H); 3.34 (s, 3H); 2.38 (s, 3H);

Example No. 5-9

$^1$H-NMR (400 Mhz, DMSO-d$_6$): δ=13.68 (br s, 1H); 8.00 (d, 1H); 7.79 (d, 1H); 4.94 (s, 3H); 2.39 (s, 3H);

Example No. 5-35

$^1$H-NMR (400 Mhz, DMSO-d$_6$): δ=13.71 (br s, 1H); 7.94 (d, 1H); 7.62 (d, 1H); 3.79 (s, 3H); 2.50 (s, 3H);

Example No. 5-37

$^1$H-NMR (400 Mhz, DMSO-d$_6$): δ=13.69 (br s, 1H); 7.95 (d, 1H); 7.64 (d, 1H); 3.79 (s, 3H); 2.34 (m, 1H); 1.15 (m, 4H);

Example No. 5-45

$^1$H-NMR (400 Mhz, DMSO-d$_6$): δ=13.84 (br s, 1H); 7.92 (d, 1H); 7.81 (d, 1H); 2.59 (s, 3H); 2.34 (s, 3H);

Example No. 5-49

$^1$H-NMR (400 Mhz, DMSO-d$_6$): δ=13.80 (br s, 1H); 7.92 (d, 1H); 7.80 (d, 1H); 2.39 (m, 1H); 2.38 (s, 3H); 1.21 (m, 4H);

Example No. 5-61

$^1$H-NMR (400 Mhz, DMSO-d$_6$): δ=13.82 (br s, 1H); 7.90 (d, 1H); 7.80 (d, 1H); 3.71 (m, 1H); 2.33 (s, 3H); 2.29 (m, 2H); 2.15 (m, 2H); 1.94 (m, 1H); 1.80 (m, 1H);

Example No. 5-62

$^1$H-NMR (400 Mhz, DMSO-d$_6$): δ=13.83 (br s, 1H); 7.92 (d, 1H); 8.00 (d, 1H); 3.32 (m, 1H); 2.31 (s, 3H); 1.90 (m, 2H); 1.76 (m, 2H); 1.64 (m, 2H); 1.57 (m, 2H);

Example No. 5-63

$^1$H-NMR (400 Mhz, DMSO-d$_6$): δ=13.83 (br s, 1H); 7.92 (d, 1H); 7.80 (d, 1H); 2.71 (m, 1H); 2.31 (s, 3H); 1.91 (m, 2H); 1.75 (m, 2H); 1.64 (m, 1H); 1.25 (m, 4H); 1.11 (m, 1H);

Example No. 5-72

$^1$H-NMR (400 Mhz, CDCl$_3$): δ=8.00 (d, 1H); 7.72 (d, 1H); 6.70 (t, 1H); 2.67 (s, 3H); 2.42 (s, 3H);

Example No. 5-74

$^1$H-NMR (400 Mhz, CDCl$_3$): δ=8.06 (d, 1H); 7.77 (d, 1H); 6.66 (t, 1H); 2.43 (s, 3H); 2.31 (m, 1H); 1.44 (m, 2H); 1.22 (m, 2H);

Example No. 5-99

$^1$H-NMR (400 Mhz, CDCl$_3$): δ=8.07 (d, 1H); 7.71 (d, 1H); 2.63 (s, 3H);

Example No. 5-100

$^1$H-NMR (400 Mhz, DMSO-d$_6$): δ=13.98 (br s, 1H); 7.99 (d, 1H); 7.92 (d, 1H); 2.88 (q, 2H); 1.11 (t, 3H);

Example No. 5-101

$^1$H-NMR (400 Mhz, CDCl$_3$): δ=8.05 (d, 1H); 7.70 (d, 1H); 2.85 (t, 2H); 1.82 (m, 2H); 1.03 (t, 3H);

Example No. 5-102

¹H-NMR (400 Mhz, CDCl₃): δ=8.06 (d, 1H); 7.71 (d, 1H); 3.06 (m, 1H); 1.25 (d, 6H);

Example No. 5-103

¹H-NMR (400 Mhz, DMSO-d₆): δ=14.11 (br s, 1H); 8.00 (d, 1H); 7.92 (d, 1H); 2.38 (m, 1H); 1.19 (m, 4H);

Example No. 5-105

¹H-NMR (400 Mhz, CDCl₃): δ=8.02 (d, 1H); 7.71 (d, 1H); 1.32 (s, 9H);

Example No. 5-106

¹H-NMR (400 Mhz, CDCl₃): δ=8.11 (d, 1H); 7.72 (d, 1H); 4.43 (s, 2H); 3.48 (s, 3H);

Example No. 5-107

¹H-NMR (400 Mhz, CDCl₃): δ=8.14 (d, 1H); 7.75 (d, 1H); 4.54 (s, 2H);

Example No. 5-108

¹H-NMR (400 Mhz, DMSO-d₆): δ=14.21 (br s, 1H); 8.14 (d, 1H); 8.02 (d, 1H); 2.58 (s, 3H);

Example No. 5-109

¹H-NMR (400 Mhz, DMSO-d₆): δ=14.11 (br s, 1H); 7.99 (d, 1H); 7.94 (d, 1H); 1.38 (m, 2H); 1.19 (s, 3H); 1.11 (m, 2H);

Example No. 5-110

¹H-NMR (400 Mhz, DMSO-d₆): δ=14.07 (br s, 1H); 7.97 (d, 1H); 7.91 (d, 1H); 2.15 (m, 1H); 1.60 (m, 1H); 1.48 (m, 1H); 1.15 (d, 3H); 1.11 (m, 1H);

Example No. 5-111

¹H-NMR (400 Mhz, DMSO-d₆): δ=14.01 (br s, 1H); 7.97 (d, 1H); 7.90 (d, 1H); 2.24 (m, 1H); 1.30 (m, 2H); 1.29 (s, 3H); 1.21 (s, 3H);

Example No. 5-112

¹H-NMR (400 Mhz, DMSO-d₆): δ=14.10 (br s, 1H); 7.99 (d, 2H); 7.94 (2×d, 2H); 1.63 (m, 4H); 1.15 (m, 7H); 0.85 (m, 1H);

Example No. 5-115

¹H-NMR (400 Mhz, DMSO-d₆): δ=14.09 (br s, 1H); 7.98 (d, 1H); 7.91 (d, 1H); 3.74 (m, 1H); 2.31 (m, 2H); 2.17 (m, 2H); 1.98 (m, 1H); 1.81 (m, 1H);

Example No. 5-116

¹H-NMR (400 Mhz, DMSO-d₆): δ=14.13 (br s, 1H); 7.98 (d, 1H); 7.92 (d, 1H); 3.32 (m, 1H); 1.93 (m, 2H); 1.77 (m, 2H); 1.67 (m, 2H); 1.58 (m, 2H);

Example No. 5-117

¹H-NMR (400 Mhz, DMSO-d₆): δ=14.11 (br s, 1H); 7.98 (d, 1H); 7.92 (d, 1H); 2.74 (m, 1H); 1.92 (m, 2H); 1.76 (m, 2H); 1.64 (m, 1H); 1.28 (m, 4H); 1.15 (m, 1H);

Example No. 5-124

¹H-NMR (400 Mhz, CDCl₃): δ=8.26 (d, 1H); 7.80 (d, 1H);

Example-No. 5-125

¹H-NMR (400 Mhz, DMSO-d₆): δ=14.29 (br s, 1H); 8.18 (d, 1H); 8.06 (d, 1H); 6.97 (t, 1H);

Example No. 5-126

¹H-NMR (400 Mhz, CDCl₃): δ=8.08 (d, 1H); 7.65 (d, 1H); 6.73 (t, 1H); 2.65 (s, 3H);

Example No. 5-127

¹H-NMR (400 Mhz, DMSO-d₆): δ=13.89 (br s, 1H); 7.93 (d, 1H); 7.72 (d, 1H); 7.06 (t, 1H); 2.87 (q, 2H); 1.11 (t, 3H);

Example No. 5-130

¹H-NMR (400 Mhz, CDCl₃): δ=8.09 (d, 1H); 7.69 (d, 1H); 6.69 (t, 1H); 2.34 (m, 1H); 1.44 (m, 2H); 1.23 (m, 2H);

Example No. 5-153

¹H-NMR (400 Mhz, DMSO-d₆): δ=14.15 (br s, 1H); 7.95 (d, 1H); 7.90 (d, 1H); 2.67 (s, 3H);

Example No. 5-155

¹H-NMR (400 Mhz, DMSO-d₆): δ=14.10 (br s, 1H); 7.95 (d, 1H); 7.89 (d, 1H); 2.36 (m, 1H); M 1.24 (m, 4H);

Example No. 5-160

¹H-NMR (400 Mhz, DMSO-d₆): δ=13.92 (br s, 1H); 7.84 (d, 1H); 7.75 (d, 1H); 7.07 (t, 1H); 2.57 (s, 3H);

Example No. 5-161

¹H-NMR (400 Mhz, DMSO-d₆): δ=13.89 (br s, 1H); 7.85 (d, 1H); 7.76 (d, 1H); 7.04 (t, 1H); 2.87 (q, 2H); 1.13 (t, 3H);

Example No. 5-162

¹H-NMR (400 Mhz, DMSO-d₆): δ=13.89 (br s, 1H); 7.85 (d, 1H); 7.77 (d, 1H); 6.96 (t, 1H); 2.35 (m, 1H); 1.24 (m, 4H);

Example No. 5-187

¹H-NMR (400 Mhz, DMSO-d₆): δ=13.55 (br s, 1H); 7.75 (d, 1H); 7.71 (d, 1H); 2.62 (s, 3H); 2.21 (m, 1H); 0.92 (m, 2H); 0.45 (m, 2H);

Example No. 5-189

¹H-NMR (400 Mhz, DMSO-d₆): δ=13.52 (br s, 1H); 7.75 (d, 1H); 7.71 (d, 1H); 2.44 (m, 1H); 2.16 (m, 1H); 1.18 (m, 4H); 0.92 (m, 2H); 0.48 (m, 2H);

Example No. 5-201

$^1$H-NMR (400 Mhz, DMSO-$d_6$): δ=14.12 (br s, 1H); 8.15 (d, 1H); 8.03 (d, 1H); 7.73 (m, 1H); 7.56 (m, 2H);

Example No. 5-203

$^1$H-NMR (400 Mhz, DMSO-$d_6$): δ=14.00 (br s, 1H); 8.04 (d, 1H); 7.96 (d, 1H); 6.71 (dd, 1H); 6.38 (d, 1H); 5.98 (d, 1H).

B. Formulation Examples a) A dusting product is obtained by mixing 10 parts by weight of a compound of the formula (I) and 90 parts by weight of talc as inert substance and comminuting the mixture in a hammer mill b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxyethylated nonylphenol as emulsifier.

e) Water-dispersible granules are obtained by mixing
   75 parts by weight of a compound of the formula (I),
   10 parts by weight of calcium lignosulfonate,
   5 parts by weight of sodium lauryl sulfate,
   3 parts by weight of polyvinyl alcohol and
   7 parts by weight of kaolin,
   grinding the mixture in a pinned-disk mill, and granulating the powder in a fluidized bed by spray application of water as a granulating liquid.

f) Water-dispersible granules are also obtained by homogenizing and precomminuting, in a colloid mill,
   25 parts by weight of a compound of the formula (I),
   5 parts by weight of sodium 2,2'-dinaphthylmethane-6,6'-disulfonate
   2 parts by weight of sodium oleoylmethyltaurate,
   1 part by weight of polyvinyl alcohol,
   17 parts by weight of calcium carbonate and
   50 parts by weight of water,
   then grinding the mixture in a bead mill and atomizing and drying the resulting suspension in a spray tower by means of a one-phase nozzle.

C. Biological Examples

The abbreviations used here mean:

| | | | |
|---|---|---|---|
| ABUTH | Abutilon theophrasti | ALOMY | Alopecurus myosuroides |
| AMARE | Amaranthus retroflexus | AVEFA | Avena fatua |
| CYPES | Cyperus serotinus | DIGSA | Digitaria sanguinalis |
| ECHCG | Echinocloa crus galli | HORMU | Hordeum murinum |
| LOLMU | Lolium multiflorum | LOLRI | Lolium rigidum Gaudin |
| MATIN | Matricaria inodora | PHBPU | Pharbitis purpureum |
| POLCO | Polygonum convolvulus | SETVI | Setaria viridis |
| STEME | Stellaria media | VERPE | Veronica persica |
| VIOTR | Viola tricolor | | |
| D1 | WO 2012/028579 A1 | | |

1. Pre-Emergence Herbicidal Action Against Harmful Plants

Seeds of monocotyledonous and dicotyledonous weed plants and crop plants are laid out in sandy loam soil in wood-fiber pots and covered with soil. The compounds of the invention, formulated in the form of wettable powders (WP) or as emulsion concentrates (EC), are then applied to the surface of the covering soil in the form of an aqueous suspension or emulsion at a water application rate equating to 600 to 800l/ha, with addition of 0.2% wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants). Here, numerous compounds according to the invention showed, at an application rate of 320 g or less per hectare, an activity of at least 80% against a large number of important harmful plants.

In addition, some substances are also harmless to dicotyledonous crops such as soya, cotton, oilseed rape, sugar beet or potatoes. Some of the compounds according to the invention exhibit high selectivity and are therefore suitable for controlling unwanted vegetation in agricultural crops by the pre-emergence method. The data of Tables B1 to B17 below illustrate, in an exemplary manner, the pre-emergence herbicidal action of the compounds according to the invention, the herbicidal activity being stated in percent.

TABLE B1

Pre-emergence action against ALOMY

| Example number | Dosage [g/ha] | ALOMY |
|---|---|---|
| 1-168 | 320 | 100 |
| 2-233 | 320 | 100 |
| 1-16 | 320 | 90 |
| 2-60 | 320 | 100 |
| 1-164 | 320 | 100 |
| 2-18 | 320 | 100 |
| 2-164 | 320 | 100 |
| 1-163 | 320 | 90 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 90 |
| 3-164 | 320 | 90 |
| 1-127 | 320 | 100 |
| 1-65 | 320 | 100 |
| 2-195 | 320 | 90 |
| 2-65 | 320 | 100 |
| 2-22 | 320 | 90 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 90 |

TABLE B1-continued

Pre-emergence action against ALOMY

| Example number | Dosage [g/ha] | ALOMY |
|---|---|---|
| 1-50 | 320 | 100 |
| 2-50 | 320 | 100 |
| 1-141 | 320 | 100 |
| 2-148 | 320 | 90 |
| 1-58 | 320 | 100 |
| 2-58 | 320 | 100 |
| 1-139 | 320 | 100 |
| 2-139 | 320 | 100 |
| 1-146 | 320 | 90 |
| 1-192 | 320 | 100 |
| 1-144 | 320 | 100 |
| 1-284 | 320 | 90 |
| 1-145 | 320 | 100 |
| 1-153 | 320 | 90 |
| 1-114 | 320 | 90 |
| 1-115 | 320 | 100 |
| 2-115 | 320 | 100 |
| 1-140 | 320 | 100 |
| 2-137 | 320 | 90 |
| 1-121 | 320 | 90 |
| 1-147 | 320 | 100 |
| 2-121 | 320 | 90 |
| 2-141 | 320 | 100 |
| 1-22 | 320 | 90 |
| 2-14 | 320 | 80 |
| 1-195 | 320 | 90 |
| 2-15 | 320 | 100 |
| 3-65 | 320 | 80 |
| 2-144 | 320 | 100 |
| 1-48 | 320 | 90 |
| 3-7 | 320 | 80 |
| 2-114 | 320 | 80 |
| 2-147 | 320 | 90 |
| 2-284 | 320 | 90 |
| 1-116 | 320 | 100 |
| 2-9 | 320 | 90 |
| 2-140 | 320 | 90 |
| 2-123 | 320 | 100 |
| 1-3 | 320 | 90 |
| 3-195 | 320 | 80 |
| 3-197 | 320 | 90 |
| 2-129 | 320 | 90 |
| 3-129 | 320 | 90 |
| 3-137 | 320 | 90 |
| 2-48 | 320 | 90 |
| 3-48 | 320 | 90 |
| 3-16 | 320 | 80 |
| 3-144 | 320 | 90 |
| 3-192 | 320 | 90 |
| 2-7 | 320 | 80 |
| 3-141 | 320 | 90 |
| 3-14 | 320 | 90 |
| 1-138 | 320 | 100 |
| 3-50 | 320 | 100 |
| 3-18 | 320 | 80 |
| 3-58 | 320 | 90 |
| 1-280 | 320 | 90 |
| 2-1 | 320 | 90 |
| 3-1 | 320 | 90 |
| 1-123 | 320 | 90 |
| 3-15 | 320 | 80 |
| 1-18 | 320 | 100 |
| 1-9 | 320 | 90 |
| 3-140 | 320 | 90 |
| 1-1 | 320 | 80 |
| 2-153 | 320 | 90 |
| 2-280 | 320 | 100 |
| 3-3 | 320 | 90 |
| 2-136 | 320 | 90 |
| 3-135 | 320 | 80 |
| 2-135 | 320 | 90 |

TABLE B2

Pre-emergence action against AVEFA

| Example number | Dosage [g/ha] | AVEFA |
|---|---|---|
| 1-168 | 320 | 100 |
| 2-233 | 320 | 100 |
| 1-16 | 320 | 90 |
| 2-60 | 320 | 100 |
| 1-164 | 320 | 100 |
| 2-18 | 320 | 100 |
| 2-164 | 320 | 90 |
| 1-163 | 320 | 100 |
| 1-165 | 320 | 100 |
| 1-148 | 320 | 90 |
| 1-60 | 320 | 100 |
| 1-67 | 320 | 80 |
| 1-233 | 320 | 100 |
| 3-67 | 320 | 100 |
| 2-16 | 320 | 90 |
| 3-164 | 320 | 100 |
| 1-127 | 320 | 90 |
| 1-65 | 320 | 100 |
| 2-195 | 320 | 90 |
| 2-65 | 320 | 100 |
| 2-22 | 320 | 100 |
| 2-67 | 320 | 100 |
| 1-129 | 320 | 100 |
| 2-116 | 320 | 90 |
| 2-168 | 320 | 90 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 90 |
| 1-58 | 320 | 100 |
| 2-58 | 320 | 90 |
| 1-139 | 320 | 100 |
| 2-139 | 320 | 80 |
| 1-146 | 320 | 90 |
| 1-192 | 320 | 100 |
| 1-144 | 320 | 100 |
| 1-284 | 320 | 90 |
| 1-145 | 320 | 100 |
| 1-153 | 320 | 80 |
| 1-114 | 320 | 100 |
| 1-115 | 320 | 100 |
| 2-115 | 320 | 90 |
| 1-140 | 320 | 80 |
| 2-137 | 320 | 90 |
| 1-121 | 320 | 90 |
| 1-147 | 320 | 90 |
| 2-121 | 320 | 90 |
| 2-141 | 320 | 100 |
| 1-22 | 320 | 100 |
| 2-14 | 320 | 90 |
| 1-195 | 320 | 100 |
| 2-15 | 320 | 100 |
| 3-65 | 320 | 100 |
| 2-144 | 320 | 100 |
| 1-48 | 320 | 90 |
| 3-7 | 320 | 90 |
| 2-114 | 320 | 80 |
| 2-147 | 320 | 90 |
| 2-284 | 320 | 90 |
| 1-116 | 320 | 100 |
| 2-9 | 320 | 100 |
| 2-140 | 320 | 80 |
| 2-123 | 320 | 80 |
| 3-195 | 320 | 90 |
| 3-197 | 320 | 90 |
| 2-129 | 320 | 100 |
| 3-129 | 320 | 100 |
| 3-137 | 320 | 80 |
| 3-16 | 320 | 80 |
| 3-144 | 320 | 80 |
| 3-123 | 320 | 100 |
| 3-192 | 320 | 90 |
| 3-141 | 320 | 80 |
| 2-127 | 320 | 90 |

TABLE B2-continued

Pre-emergence action against AVEFA

| Example number | Dosage [g/ha] | AVEFA |
|---|---|---|
| 1-138 | 320 | 100 |
| 3-50 | 320 | 100 |
| 3-18 | 320 | 80 |
| 3-58 | 320 | 80 |
| 1-285 | 320 | 80 |
| 1-123 | 320 | 80 |
| 1-18 | 320 | 100 |
| 1-9 | 320 | 80 |
| 1-286 | 320 | 90 |
| 2-285 | 320 | 80 |
| 3-9 | 320 | 90 |

TABLE B3

Pre-emergence action against CYPES

| Example number | Dosage [g/ha] | CYPES |
|---|---|---|
| 1-168 | 320 | 90 |
| 2-60 | 320 | 100 |
| 1-164 | 320 | 100 |
| 2-18 | 320 | 100 |
| 2-164 | 320 | 100 |
| 1-148 | 320 | 90 |
| 1-60 | 320 | 100 |
| 1-67 | 320 | 90 |
| 3-67 | 320 | 100 |
| 3-164 | 320 | 100 |
| 1-127 | 320 | 90 |
| 2-195 | 320 | 100 |
| 2-65 | 320 | 90 |
| 1-129 | 320 | 100 |
| 2-116 | 320 | 90 |
| 1-137 | 320 | 100 |
| 1-50 | 320 | 100 |
| 2-50 | 320 | 100 |
| 1-141 | 320 | 100 |
| 2-148 | 320 | 90 |
| 1-58 | 320 | 100 |
| 2-58 | 320 | 100 |
| 1-139 | 320 | 90 |
| 2-139 | 320 | 100 |
| 1-192 | 320 | 90 |
| 1-144 | 320 | 100 |
| 1-145 | 320 | 100 |
| 1-114 | 320 | 100 |
| 1-115 | 320 | 100 |
| 2-115 | 320 | 90 |
| 1-140 | 320 | 90 |
| 2-137 | 320 | 100 |
| 1-121 | 320 | 90 |
| 1-147 | 320 | 100 |
| 2-121 | 320 | 90 |
| 2-141 | 320 | 90 |
| 2-14 | 320 | 90 |
| 1-195 | 320 | 100 |
| 2-15 | 320 | 90 |
| 2-144 | 320 | 100 |
| 1-48 | 320 | 90 |
| 3-7 | 320 | 100 |
| 2-114 | 320 | 90 |
| 2-147 | 320 | 80 |
| 2-9 | 320 | 90 |
| 2-123 | 320 | 90 |
| 3-195 | 320 | 90 |
| 3-197 | 320 | 80 |
| 2-129 | 320 | 100 |
| 3-129 | 320 | 90 |
| 3-137 | 320 | 90 |
| 2-48 | 320 | 100 |
| 3-48 | 320 | 90 |
| 3-144 | 320 | 100 |
| 3-123 | 320 | 80 |

TABLE B3-continued

Pre-emergence action against CYPES

| Example number | Dosage [g/ha] | CYPES |
|---|---|---|
| 3-192 | 320 | 100 |
| 2-7 | 320 | 100 |
| 2-127 | 320 | 90 |
| 3-14 | 320 | 80 |
| 1-138 | 320 | 100 |
| 3-50 | 320 | 90 |
| 3-18 | 320 | 90 |
| 3-58 | 320 | 90 |
| 1-280 | 320 | 100 |
| 2-143 | 320 | 90 |
| 2-1 | 320 | 80 |
| 3-1 | 320 | 90 |
| 2-145 | 320 | 100 |
| 1-7 | 320 | 100 |
| 1-18 | 320 | 90 |
| 1-9 | 320 | 80 |
| 1-143 | 320 | 90 |
| 3-3 | 320 | 90 |

TABLE B4

Pre-emergence action against DIGSA

| Example number | Dosage [g/ha] | DIGSA |
|---|---|---|
| 2-233 | 320 | 100 |
| 1-16 | 320 | 100 |
| 1-163 | 320 | 100 |
| 1-165 | 320 | 100 |
| 1-233 | 320 | 100 |
| 2-16 | 320 | 100 |
| 2-22 | 320 | 100 |
| 1-146 | 320 | 100 |
| 1-284 | 320 | 100 |
| 1-153 | 320 | 100 |
| 1-22 | 320 | 100 |
| 2-284 | 320 | 100 |
| 1-3 | 320 | 90 |
| 3-16 | 320 | 90 |
| 1-285 | 320 | 90 |
| 2-163 | 320 | 90 |
| 2-153 | 320 | 100 |
| 1-154 | 320 | 100 |
| 3-163 | 320 | 100 |
| 1-286 | 320 | 100 |
| 3-280 | 320 | 100 |
| 2-155 | 320 | 90 |
| 3-153 | 320 | 100 |
| 1-155 | 320 | 90 |
| 1-287 | 320 | 80 |
| 3-281 | 320 | 80 |

TABLE B5

Pre-emergence action against ECHCG

| Example number | Dosage [g/ha] | ECHCG |
|---|---|---|
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 100 |
| 2-164 | 320 | 100 |
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |

TABLE B5-continued

Pre-emergence action against ECHCG

| Example number | Dosage [g/ha] | ECHCG |
|---|---|---|
| 3-67 | 320 | 100 |
| 2-16 | 320 | 100 |
| 3-164 | 320 | 100 |
| 1-127 | 320 | 100 |
| 1-65 | 320 | 100 |
| 2-195 | 320 | 100 |
| 2-65 | 320 | 100 |
| 2-22 | 320 | 90 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 100 |
| 1-58 | 320 | 100 |
| 2-58 | 320 | 100 |
| 1-139 | 320 | 100 |
| 2-139 | 320 | 100 |
| 1-146 | 320 | 100 |
| 1-192 | 320 | 100 |
| 1-144 | 320 | 100 |
| 1-284 | 320 | 100 |
| 1-145 | 320 | 100 |
| 1-153 | 320 | 90 |
| 1-114 | 320 | 100 |
| 1-115 | 320 | 100 |
| 2-115 | 320 | 100 |
| 1-140 | 320 | 100 |
| 2-137 | 320 | 100 |
| 1-121 | 320 | 100 |
| 1-147 | 320 | 100 |
| 2-121 | 320 | 100 |
| 2-141 | 320 | 100 |
| 1-22 | 320 | 100 |
| 2-14 | 320 | 100 |
| 1-195 | 320 | 100 |
| 2-15 | 320 | 100 |
| 3-65 | 320 | 100 |
| 2-144 | 320 | 100 |
| 1-48 | 320 | 100 |
| 3-7 | 320 | 100 |
| 2-114 | 320 | 100 |
| 2-147 | 320 | 100 |
| 2-284 | 320 | 100 |
| 1-116 | 320 | 100 |
| 2-9 | 320 | 100 |
| 2-140 | 320 | 100 |
| 2-123 | 320 | 100 |
| 1-3 | 320 | 90 |
| 3-195 | 320 | 100 |
| 3-197 | 320 | 100 |
| 2-129 | 320 | 100 |
| 3-129 | 320 | 100 |
| 3-137 | 320 | 100 |
| 2-48 | 320 | 100 |
| 3-48 | 320 | 100 |
| 3-16 | 320 | 90 |
| 3-144 | 320 | 100 |
| 3-123 | 320 | 90 |
| 3-192 | 320 | 100 |
| 2-7 | 320 | 100 |
| 3-141 | 320 | 100 |
| 2-127 | 320 | 100 |
| 3-14 | 320 | 100 |
| 1-138 | 320 | 100 |
| 3-18 | 320 | 100 |
| 3-58 | 320 | 100 |
| 1-280 | 320 | 100 |
| 2-143 | 320 | 90 |
| 2-1 | 320 | 90 |
| 3-1 | 320 | 90 |
| 1-285 | 320 | 80 |
| 2-145 | 320 | 90 |
| 1-123 | 320 | 100 |
| 1-7 | 320 | 100 |
| 3-15 | 320 | 100 |
| 1-18 | 320 | 100 |
| 1-9 | 320 | 100 |
| 1-143 | 320 | 100 |
| 2-163 | 320 | 90 |
| 3-140 | 320 | 90 |
| 1-1 | 320 | 90 |
| 1-154 | 320 | 100 |
| 2-280 | 320 | 100 |
| 3-3 | 320 | 100 |
| 1-162 | 320 | 100 |
| 3-280 | 320 | 80 |
| 2-285 | 320 | 80 |
| 2-155 | 320 | 80 |
| 3-9 | 320 | 100 |
| 3-134 | 320 | 100 |
| 3-135 | 320 | 90 |
| 1-134 | 320 | 90 |
| 1-287 | 320 | 80 |
| 2-135 | 320 | 90 |
| 3-136 | 320 | 80 |
| 1-135 | 320 | 90 |
| 2-134 | 320 | 80 |

TABLE B6

Pre-emergence action against LOLMU

| Example number | Dosage [g/ha] | LOLMU |
|---|---|---|
| 1-127 | 320 | 80 |
| 2-195 | 320 | 80 |
| 1-129 | 320 | 100 |
| 2-116 | 320 | 100 |
| 1-137 | 320 | 100 |
| 1-50 | 320 | 100 |
| 2-50 | 320 | 100 |
| 1-141 | 320 | 100 |
| 1-58 | 320 | 90 |
| 2-58 | 320 | 90 |
| 1-114 | 320 | 100 |
| 1-115 | 320 | 100 |
| 2-115 | 320 | 100 |
| 2-137 | 320 | 80 |
| 1-121 | 320 | 90 |
| 2-141 | 320 | 100 |
| 2-14 | 320 | 80 |
| 1-195 | 320 | 90 |
| 2-15 | 320 | 100 |
| 1-48 | 320 | 80 |
| 2-114 | 320 | 80 |
| 1-116 | 320 | 100 |
| 2-123 | 320 | 90 |
| 2-129 | 320 | 90 |
| 2-48 | 320 | 80 |

TABLE B7

Pre-emergence action against LOLRI

| Example number | Dosage [g/ha] | LOLRI |
|---|---|---|
| 1-168 | 320 | 100 |
| 2-233 | 320 | 90 |
| 1-16 | 320 | 100 |
| 2-60 | 320 | 100 |
| 1-164 | 320 | 100 |
| 2-18 | 320 | 100 |

TABLE B7-continued

Pre-emergence action against LOLRI

| Example number | Dosage [g/ha] | LOLRI |
|---|---|---|
| 2-164 | 320 | 80 |
| 1-163 | 320 | 90 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 90 |
| 3-164 | 320 | 90 |
| 1-65 | 320 | 80 |
| 2-22 | 320 | 90 |
| 2-67 | 320 | 100 |
| 2-168 | 320 | 100 |
| 3-168 | 320 | 100 |
| 2-148 | 320 | 90 |
| 1-139 | 320 | 100 |
| 2-139 | 320 | 100 |
| 1-192 | 320 | 100 |
| 1-144 | 320 | 100 |
| 1-284 | 320 | 90 |
| 1-145 | 320 | 100 |
| 1-153 | 320 | 90 |
| 1-140 | 320 | 100 |
| 1-147 | 320 | 90 |
| 1-22 | 320 | 100 |
| 2-144 | 320 | 100 |
| 2-147 | 320 | 90 |
| 2-140 | 320 | 90 |
| 1-285 | 320 | 80 |
| 1-143 | 320 | 80 |

TABLE B8

Pre-emergence action against LOLRI

| Example number | Dosage [g/ha] | SETVI |
|---|---|---|
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 100 |
| 2-164 | 320 | 100 |
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 90 |
| 3-164 | 320 | 100 |
| 1-127 | 320 | 90 |
| 1-65 | 320 | 100 |
| 2-195 | 320 | 100 |
| 2-65 | 320 | 100 |
| 2-22 | 320 | 100 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 100 |
| 1-58 | 320 | 100 |
| 2-58 | 320 | 100 |
| 1-139 | 320 | 100 |
| 2-139 | 320 | 100 |
| 1-146 | 320 | 100 |
| 1-192 | 320 | 100 |
| 1-144 | 320 | 100 |
| 1-284 | 320 | 100 |
| 1-145 | 320 | 100 |
| 1-153 | 320 | 100 |
| 1-114 | 320 | 100 |
| 1-115 | 320 | 90 |
| 2-115 | 320 | 90 |
| 1-140 | 320 | 100 |
| 2-137 | 320 | 100 |
| 1-121 | 320 | 100 |
| 1-147 | 320 | 100 |
| 2-121 | 320 | 90 |
| 2-141 | 320 | 100 |
| 1-22 | 320 | 100 |
| 2-14 | 320 | 100 |
| 1-195 | 320 | 100 |
| 2-15 | 320 | 100 |
| 3-65 | 320 | 100 |
| 2-144 | 320 | 100 |
| 1-48 | 320 | 100 |
| 3-7 | 320 | 100 |
| 2-114 | 320 | 90 |
| 2-147 | 320 | 100 |
| 2-284 | 320 | 100 |
| 1-116 | 320 | 100 |
| 2-9 | 320 | 100 |
| 2-140 | 320 | 100 |
| 2-123 | 320 | 100 |
| 1-3 | 320 | 90 |
| 3-195 | 320 | 100 |
| 3-197 | 320 | 100 |
| 2-129 | 320 | 100 |
| 3-129 | 320 | 100 |
| 3-137 | 320 | 90 |
| 2-48 | 320 | 100 |
| 3-48 | 320 | 100 |
| 3-16 | 320 | 100 |
| 3-144 | 320 | 100 |
| 3-123 | 320 | 100 |
| 3-192 | 320 | 100 |
| 2-7 | 320 | 100 |
| 3-141 | 320 | 100 |
| 2-127 | 320 | 90 |
| 3-14 | 320 | 100 |
| 1-138 | 320 | 100 |
| 3-50 | 320 | 100 |
| 3-18 | 320 | 100 |
| 1-280 | 320 | 90 |
| 2-143 | 320 | 80 |
| 2-1 | 320 | 90 |
| 3-1 | 320 | 90 |
| 2-145 | 320 | 100 |
| 1-123 | 320 | 100 |
| 1-7 | 320 | 100 |
| 3-15 | 320 | 100 |
| 1-18 | 320 | 100 |
| 1-9 | 320 | 100 |
| 1-143 | 320 | 90 |
| 2-163 | 320 | 100 |
| 3-140 | 320 | 90 |
| 1-1 | 320 | 90 |
| 2-153 | 320 | 100 |
| 1-154 | 320 | 80 |
| 3-3 | 320 | 90 |
| 1-162 | 320 | 100 |
| 3-163 | 320 | 100 |
| 3-280 | 320 | 100 |
| 3-9 | 320 | 100 |
| 3-153 | 320 | 80 |

TABLE B9

Pre-emergence action against ABUTH

| Example number | Dosage [g/ha] | ABUTH |
|---|---|---|
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 100 |
| 2-164 | 320 | 100 |
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 100 |
| 3-164 | 320 | 100 |
| 1-127 | 320 | 100 |
| 1-65 | 320 | 100 |
| 2-195 | 320 | 100 |
| 2-65 | 320 | 100 |
| 2-22 | 320 | 100 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 100 |
| 1-58 | 320 | 100 |
| 2-58 | 320 | 100 |
| 1-139 | 320 | 100 |
| 2-139 | 320 | 100 |
| 1-146 | 320 | 100 |
| 1-192 | 320 | 100 |
| 1-144 | 320 | 100 |
| 1-284 | 320 | 100 |
| 1-145 | 320 | 100 |
| 1-153 | 320 | 100 |
| 1-114 | 320 | 100 |
| 1-115 | 320 | 100 |
| 2-115 | 320 | 100 |
| 1-140 | 320 | 100 |
| 2-137 | 320 | 100 |
| 1-121 | 320 | 90 |
| 1-147 | 320 | 100 |
| 2-121 | 320 | 100 |
| 2-141 | 320 | 100 |
| 1-22 | 320 | 100 |
| 2-14 | 320 | 100 |
| 1-195 | 320 | 100 |
| 2-15 | 320 | 100 |
| 3-65 | 320 | 100 |
| 2-144 | 320 | 100 |
| 1-48 | 320 | 100 |
| 3-7 | 320 | 100 |
| 2-114 | 320 | 100 |
| 2-147 | 320 | 100 |
| 2-284 | 320 | 100 |
| 1-116 | 320 | 90 |
| 2-9 | 320 | 100 |
| 2-140 | 320 | 100 |
| 2-123 | 320 | 100 |
| 1-3 | 320 | 90 |
| 3-195 | 320 | 100 |
| 3-197 | 320 | 100 |
| 2-129 | 320 | 100 |
| 3-129 | 320 | 100 |
| 3-137 | 320 | 100 |
| 2-48 | 320 | 100 |
| 3-48 | 320 | 100 |
| 3-16 | 320 | 100 |
| 3-144 | 320 | 100 |
| 3-123 | 320 | 100 |
| 3-192 | 320 | 100 |
| 2-7 | 320 | 100 |
| 3-141 | 320 | 100 |
| 2-127 | 320 | 100 |
| 3-14 | 320 | 100 |
| 1-138 | 320 | 100 |
| 3-50 | 320 | 100 |
| 3-18 | 320 | 100 |
| 3-58 | 320 | 100 |
| 1-280 | 320 | 90 |
| 2-143 | 320 | 100 |
| 2-1 | 320 | 90 |
| 3-1 | 320 | 100 |
| 1-285 | 320 | 100 |
| 2-145 | 320 | 100 |
| 1-123 | 320 | 90 |
| 1-7 | 320 | 100 |
| 3-15 | 320 | 100 |
| 1-18 | 320 | 100 |
| 1-9 | 320 | 100 |
| 1-143 | 320 | 100 |
| 2-163 | 320 | 100 |
| 3-140 | 320 | 100 |
| 1-1 | 320 | 90 |
| 2-153 | 320 | 100 |
| 1-154 | 320 | 100 |
| 3-3 | 320 | 80 |
| 1-162 | 320 | 100 |
| 3-163 | 320 | 100 |
| 1-286 | 320 | 100 |
| 3-280 | 320 | 100 |
| 2-285 | 320 | 100 |
| 2-155 | 320 | 100 |
| 3-9 | 320 | 100 |
| 2-136 | 320 | 90 |
| 3-134 | 320 | 100 |
| 1-134 | 320 | 90 |
| 3-153 | 320 | 100 |
| 1-155 | 320 | 100 |
| 1-287 | 320 | 100 |
| 3-281 | 320 | 100 |
| 3-136 | 320 | 80 |
| 2-286 | 320 | 80 |
| 2-162 | 320 | 100 |
| 1-282 | 320 | 90 |
| 2-282 | 320 | 100 |
| 3-155 | 320 | 100 |
| 1-283 | 320 | 90 |

TABLE B10

Pre-emergence action against AMARE

| Example number | Dosage [g/ha] | AMARE |
|---|---|---|
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 100 |
| 2-164 | 320 | 100 |
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 100 |
| 3-164 | 320 | 100 |
| 1-127 | 320 | 100 |

TABLE B10-continued

Pre-emergence action against AMARE

| Example number | Dosage [g/ha] | AMARE |
|---|---|---|
| 1-65 | 320 | 100 |
| 2-195 | 320 | 100 |
| 2-65 | 320 | 100 |
| 2-22 | 320 | 100 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 100 |
| 1-58 | 320 | 100 |
| 2-58 | 320 | 100 |
| 1-139 | 320 | 100 |
| 2-139 | 320 | 100 |
| 1-146 | 320 | 100 |
| 1-192 | 320 | 100 |
| 1-144 | 320 | 100 |
| 1-284 | 320 | 100 |
| 1-145 | 320 | 100 |
| 1-153 | 320 | 100 |
| 1-114 | 320 | 100 |
| 1-115 | 320 | 100 |
| 2-115 | 320 | 100 |
| 1-140 | 320 | 100 |
| 2-137 | 320 | 100 |
| 1-121 | 320 | 100 |
| 1-147 | 320 | 100 |
| 2-121 | 320 | 100 |
| 2-141 | 320 | 100 |
| 1-22 | 320 | 100 |
| 2-14 | 320 | 100 |
| 1-195 | 320 | 100 |
| 2-15 | 320 | 100 |
| 3-65 | 320 | 100 |
| 2-144 | 320 | 100 |
| 1-48 | 320 | 100 |
| 3-7 | 320 | 100 |
| 2-114 | 320 | 100 |
| 2-147 | 320 | 100 |
| 2-284 | 320 | 100 |
| 1-116 | 320 | 100 |
| 2-9 | 320 | 100 |
| 2-140 | 320 | 100 |
| 2-123 | 320 | 100 |
| 1-3 | 320 | 100 |
| 3-195 | 320 | 100 |
| 3-197 | 320 | 100 |
| 2-129 | 320 | 100 |
| 3-129 | 320 | 100 |
| 3-137 | 320 | 100 |
| 2-48 | 320 | 100 |
| 3-48 | 320 | 100 |
| 3-16 | 320 | 100 |
| 3-144 | 320 | 100 |
| 3-123 | 320 | 100 |
| 3-192 | 320 | 100 |
| 2-7 | 320 | 100 |
| 3-141 | 320 | 100 |
| 2-127 | 320 | 100 |
| 3-14 | 320 | 100 |
| 1-138 | 320 | 100 |
| 3-50 | 320 | 100 |
| 3-18 | 320 | 100 |
| 3-58 | 320 | 100 |
| 1-280 | 320 | 100 |
| 2-143 | 320 | 100 |
| 2-1 | 320 | 100 |
| 3-1 | 320 | 100 |
| 1-285 | 320 | 100 |
| 2-145 | 320 | 100 |
| 1-123 | 320 | 100 |
| 1-7 | 320 | 100 |
| 3-15 | 320 | 100 |
| 1-18 | 320 | 100 |
| 1-9 | 320 | 100 |
| 1-143 | 320 | 100 |
| 2-163 | 320 | 100 |
| 3-140 | 320 | 100 |
| 1-1 | 320 | 100 |
| 2-153 | 320 | 100 |
| 1-154 | 320 | 100 |
| 2-280 | 320 | 100 |
| 3-3 | 320 | 100 |
| 1-162 | 320 | 90 |
| 3-163 | 320 | 100 |
| 1-286 | 320 | 100 |
| 3-280 | 320 | 100 |
| 2-285 | 320 | 100 |
| 2-155 | 320 | 100 |
| 3-9 | 320 | 100 |
| 2-136 | 320 | 100 |
| 3-134 | 320 | 90 |
| 3-135 | 320 | 90 |
| 1-134 | 320 | 100 |
| 3-153 | 320 | 100 |
| 1-155 | 320 | 80 |
| 1-287 | 320 | 100 |
| 2-135 | 320 | 100 |
| 3-281 | 320 | 80 |
| 3-136 | 320 | 90 |
| 1-281 | 320 | 90 |
| 2-281 | 320 | 90 |
| 1-135 | 320 | 100 |
| 2-134 | 320 | 100 |
| 2-286 | 320 | 100 |
| 1-136 | 320 | 80 |
| 2-162 | 320 | 90 |
| 1-282 | 320 | 80 |
| 2-282 | 320 | 80 |
| 3-155 | 320 | 90 |

TABLE 11

Pre-emergence action against MATIN

| Example number | Dosage [g/ha] | MATIN |
|---|---|---|
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 100 |
| 2-164 | 320 | 100 |
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 90 |
| 3-164 | 320 | 100 |
| 1-127 | 320 | 100 |
| 1-65 | 320 | 100 |
| 2-195 | 320 | 100 |
| 2-65 | 320 | 90 |
| 2-22 | 320 | 100 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 100 |
| 1-50 | 320 | 100 |

TABLE 11-continued

Pre-emergence action against MATIN

| Example number | Dosage [g/ha] | MATIN |
|---|---|---|
| 2-50 | 320 | 100 |
| 1-141 | 320 | 100 |
| 2-148 | 320 | 100 |
| 1-58 | 320 | 100 |
| 2-58 | 320 | 100 |
| 1-139 | 320 | 100 |
| 2-139 | 320 | 100 |
| 1-146 | 320 | 100 |
| 1-192 | 320 | 100 |
| 1-144 | 320 | 100 |
| 1-284 | 320 | 100 |
| 1-145 | 320 | 100 |
| 1-153 | 320 | 100 |
| 1-114 | 320 | 100 |
| 1-115 | 320 | 100 |
| 2-115 | 320 | 100 |
| 1-140 | 320 | 100 |
| 2-137 | 320 | 100 |
| 1-121 | 320 | 100 |
| 1-147 | 320 | 100 |
| 2-121 | 320 | 100 |
| 2-141 | 320 | 100 |
| 1-22 | 320 | 100 |
| 2-14 | 320 | 100 |
| 1-195 | 320 | 100 |
| 2-15 | 320 | 100 |
| 3-65 | 320 | 100 |
| 2-144 | 320 | 100 |
| 1-48 | 320 | 100 |
| 3-7 | 320 | 100 |
| 2-114 | 320 | 90 |
| 2-147 | 320 | 100 |
| 2-284 | 320 | 100 |
| 1-116 | 320 | 100 |
| 2-9 | 320 | 100 |
| 2-140 | 320 | 100 |
| 2-123 | 320 | 100 |
| 1-3 | 320 | 100 |
| 3-195 | 320 | 100 |
| 3-197 | 320 | 100 |
| 2-129 | 320 | 100 |
| 3-129 | 320 | 100 |
| 3-137 | 320 | 100 |
| 2-48 | 320 | 100 |
| 3-48 | 320 | 100 |
| 3-16 | 320 | 100 |
| 3-144 | 320 | 100 |
| 3-123 | 320 | 100 |
| 3-192 | 320 | 100 |
| 2-7 | 320 | 100 |
| 3-141 | 320 | 100 |
| 2-127 | 320 | 100 |
| 3-14 | 320 | 100 |
| 1-138 | 320 | 100 |
| 3-50 | 320 | 100 |
| 3-18 | 320 | 100 |
| 3-58 | 320 | 100 |
| 1-280 | 320 | 100 |
| 2-143 | 320 | 100 |
| 2-1 | 320 | 90 |
| 3-1 | 320 | 100 |
| 1-285 | 320 | 100 |
| 2-145 | 320 | 100 |
| 1-123 | 320 | 100 |
| 1-7 | 320 | 100 |
| 3-15 | 320 | 100 |
| 1-18 | 320 | 100 |
| 1-9 | 320 | 100 |
| 1-143 | 320 | 100 |
| 2-163 | 320 | 100 |
| 3-140 | 320 | 100 |
| 1-1 | 320 | 100 |
| 2-153 | 320 | 100 |
| 1-154 | 320 | 100 |
| 2-280 | 320 | 100 |
| 3-3 | 320 | 100 |

TABLE 11-continued

Pre-emergence action against MATIN

| Example number | Dosage [g/ha] | MATIN |
|---|---|---|
| 1-162 | 320 | 80 |
| 3-163 | 320 | 100 |
| 1-286 | 320 | 90 |
| 3-280 | 320 | 90 |
| 2-285 | 320 | 90 |
| 2-155 | 320 | 100 |
| 3-9 | 320 | 90 |
| 2-136 | 320 | 100 |
| 3-134 | 320 | 90 |
| 3-135 | 320 | 90 |
| 1-134 | 320 | 100 |
| 3-153 | 320 | 90 |
| 1-155 | 320 | 90 |
| 2-135 | 320 | 90 |
| 3-136 | 320 | 90 |
| 1-281 | 320 | 90 |
| 2-281 | 320 | 90 |
| 1-135 | 320 | 90 |
| 2-134 | 320 | 90 |
| 1-136 | 320 | 100 |
| 1-282 | 320 | 80 |

TABLE B12

Pre-emergence action against PHBPU

| Example number | Dosage [g/ha] | PHBPU |
|---|---|---|
| 1-168 | 320 | 100 |
| 2-233 | 320 | 100 |
| 1-16 | 320 | 90 |
| 2-60 | 320 | 100 |
| 1-164 | 320 | 100 |
| 2-18 | 320 | 90 |
| 2-164 | 320 | 90 |
| 1-163 | 320 | 80 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 90 |
| 3-164 | 320 | 90 |
| 1-127 | 320 | 90 |
| 1-65 | 320 | 100 |
| 2-195 | 320 | 80 |
| 2-65 | 320 | 100 |
| 2-22 | 320 | 80 |
| 2-67 | 320 | 90 |
| 1-129 | 320 | 100 |
| 2-116 | 320 | 90 |
| 2-168 | 320 | 80 |
| 3-168 | 320 | 100 |
| 1-137 | 320 | 90 |
| 1-50 | 320 | 100 |
| 2-50 | 320 | 100 |
| 1-141 | 320 | 100 |
| 2-148 | 320 | 90 |
| 1-58 | 320 | 100 |
| 2-58 | 320 | 80 |
| 1-139 | 320 | 100 |
| 2-139 | 320 | 100 |
| 1-146 | 320 | 90 |
| 1-192 | 320 | 100 |
| 1-144 | 320 | 100 |
| 1-284 | 320 | 80 |
| 1-145 | 320 | 100 |
| 1-153 | 320 | 80 |
| 1-115 | 320 | 90 |
| 2-121 | 320 | 80 |
| 2-141 | 320 | 80 |
| 1-22 | 320 | 90 |

TABLE B12-continued

Pre-emergence action against PHBPU

| Example number | Dosage [g/ha] | PHBPU |
|---|---|---|
| 2-15 | 320 | 80 |
| 3-65 | 320 | 100 |
| 2-144 | 320 | 100 |
| 3-7 | 320 | 90 |
| 2-284 | 320 | 80 |
| 2-9 | 320 | 90 |
| 2-140 | 320 | 100 |
| 1-3 | 320 | 80 |
| 3-195 | 320 | 90 |
| 3-197 | 320 | 90 |
| 3-129 | 320 | 90 |
| 3-137 | 320 | 100 |
| 3-48 | 320 | 80 |
| 3-16 | 320 | 80 |
| 3-144 | 320 | 80 |
| 3-192 | 320 | 100 |
| 2-127 | 320 | 90 |
| 3-14 | 320 | 90 |
| 1-138 | 320 | 90 |
| 3-50 | 320 | 80 |
| 3-15 | 320 | 80 |
| 1-18 | 320 | 90 |
| 2-163 | 320 | 100 |
| 3-163 | 320 | 80 |
| 2-136 | 320 | 100 |
| 3-136 | 320 | 90 |
| 2-286 | 320 | 80 |

TABLE B13

Pre-emergence action against POLCO

| Example number | Dosage [g/ha] | POLCO |
|---|---|---|
| 1-168 | 320 | 90 |
| 2-233 | 320 | 90 |
| 1-16 | 320 | 80 |
| 2-60 | 320 | 100 |
| 1-164 | 320 | 100 |
| 2-18 | 320 | 90 |
| 2-164 | 320 | 100 |
| 1-163 | 320 | 90 |
| 1-165 | 320 | 90 |
| 1-148 | 320 | 90 |
| 1-60 | 320 | 100 |
| 1-67 | 320 | 100 |
| 1-233 | 320 | 80 |
| 3-67 | 320 | 90 |
| 3-164 | 320 | 100 |
| 1-127 | 320 | 90 |
| 1-65 | 320 | 100 |
| 2-195 | 320 | 90 |
| 2-65 | 320 | 90 |
| 2-22 | 320 | 80 |
| 2-67 | 320 | 90 |
| 1-129 | 320 | 80 |
| 2-116 | 320 | 90 |
| 2-168 | 320 | 90 |
| 3-168 | 320 | 80 |
| 1-137 | 320 | 100 |
| 1-50 | 320 | 90 |
| 2-50 | 320 | 80 |
| 1-141 | 320 | 80 |
| 2-148 | 320 | 90 |
| 1-58 | 320 | 100 |
| 2-58 | 320 | 100 |
| 1-146 | 320 | 80 |
| 1-192 | 320 | 80 |
| 1-144 | 320 | 80 |
| 1-145 | 320 | 100 |
| 1-114 | 320 | 90 |
| 1-115 | 320 | 80 |
| 2-115 | 320 | 80 |

TABLE B13-continued

Pre-emergence action against POLCO

| Example number | Dosage [g/ha] | POLCO |
|---|---|---|
| 1-140 | 320 | 80 |
| 2-137 | 320 | 90 |
| 1-121 | 320 | 90 |
| 2-121 | 320 | 100 |
| 2-14 | 320 | 80 |
| 1-195 | 320 | 80 |
| 3-65 | 320 | 100 |
| 1-48 | 320 | 90 |
| 3-7 | 320 | 90 |
| 1-116 | 320 | 90 |
| 2-9 | 320 | 80 |
| 1-3 | 320 | 80 |
| 2-48 | 320 | 90 |
| 3-48 | 320 | 80 |
| 3-123 | 320 | 80 |
| 2-7 | 320 | 90 |
| 3-141 | 320 | 90 |
| 3-58 | 320 | 80 |
| 2-143 | 320 | 100 |
| 2-1 | 320 | 90 |
| 3-1 | 320 | 90 |
| 2-145 | 320 | 90 |
| 1-7 | 320 | 80 |
| 1-1 | 320 | 80 |
| 2-280 | 320 | 80 |
| 3-9 | 320 | 80 |

TABLE B14

Pre-emergence action against STEME

| Example number | Dosage [g/ha] | STEME |
|---|---|---|
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 90 |
| 2-164 | 320 | 100 |
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 90 |
| 2-16 | 320 | 90 |
| 3-164 | 320 | 100 |
| 1-127 | 320 | 90 |
| 1-65 | 320 | 100 |
| 2-195 | 320 | 100 |
| 2-65 | 320 | 100 |
| 2-22 | 320 | 100 |
| 2-67 | 320 | 100 |
| 1-129 | 320 | 100 |
| 2-116 | 320 | 90 |
| 2-168 | 320 | 100 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 90 |
| 1-58 | 320 | 100 |
| 2-58 | 320 | 90 |
| 1-139 | 320 | 100 |
| 2-139 | 320 | 100 |
| 1-146 | 320 | 100 |
| 1-192 | 320 | 100 |
| 1-144 | 320 | 100 |
| 1-284 | 320 | 100 |
| 1-145 | 320 | 100 |

TABLE B14-continued

Pre-emergence action against STEME

| Example number | Dosage [g/ha] | STEME |
| --- | --- | --- |
| 1-153 | 320 | 100 |
| 1-114 | 320 | 90 |
| 1-115 | 320 | 100 |
| 2-115 | 320 | 100 |
| 1-140 | 320 | 100 |
| 2-137 | 320 | 90 |
| 1-121 | 320 | 90 |
| 1-147 | 320 | 100 |
| 2-121 | 320 | 90 |
| 2-141 | 320 | 90 |
| 1-22 | 320 | 100 |
| 2-14 | 320 | 100 |
| 1-195 | 320 | 90 |
| 2-15 | 320 | 100 |
| 3-65 | 320 | 100 |
| 2-144 | 320 | 100 |
| 1-48 | 320 | 90 |
| 3-7 | 320 | 90 |
| 2-114 | 320 | 90 |
| 2-147 | 320 | 100 |
| 2-284 | 320 | 100 |
| 1-116 | 320 | 90 |
| 2-140 | 320 | 100 |
| 2-123 | 320 | 100 |
| 1-3 | 320 | 90 |
| 3-195 | 320 | 90 |
| 3-197 | 320 | 100 |
| 2-129 | 320 | 100 |
| 3-129 | 320 | 100 |
| 3-137 | 320 | 100 |
| 2-48 | 320 | 90 |
| 3-48 | 320 | 90 |
| 3-16 | 320 | 100 |
| 3-144 | 320 | 100 |
| 3-123 | 320 | 90 |
| 3-192 | 320 | 100 |
| 2-7 | 320 | 90 |
| 3-141 | 320 | 100 |
| 2-127 | 320 | 90 |
| 3-14 | 320 | 100 |
| 3-50 | 320 | 100 |
| 3-18 | 320 | 100 |
| 3-58 | 320 | 90 |
| 1-280 | 320 | 90 |
| 2-143 | 320 | 100 |
| 2-1 | 320 | 90 |
| 3-1 | 320 | 90 |
| 1-285 | 320 | 100 |
| 2-145 | 320 | 100 |
| 1-123 | 320 | 90 |
| 1-7 | 320 | 90 |
| 3-15 | 320 | 100 |
| 1-9 | 320 | 80 |
| 1-143 | 320 | 100 |
| 2-163 | 320 | 100 |
| 3-140 | 320 | 100 |
| 1-1 | 320 | 90 |
| 2-153 | 320 | 90 |
| 1-154 | 320 | 100 |
| 2-280 | 320 | 90 |
| 3-3 | 320 | 90 |
| 1-162 | 320 | 100 |
| 3-163 | 320 | 90 |
| 1-286 | 320 | 90 |
| 3-280 | 320 | 100 |
| 2-285 | 320 | 100 |
| 2-155 | 320 | 100 |
| 2-136 | 320 | 90 |
| 3-134 | 320 | 90 |
| 3-135 | 320 | 90 |
| 1-134 | 320 | 90 |
| 1-155 | 320 | 90 |
| 2-135 | 320 | 90 |
| 3-281 | 320 | 90 |
| 1-281 | 320 | 80 |
| 2-281 | 320 | 90 |
| 1-135 | 320 | 90 |
| 2-134 | 320 | 90 |
| 1-136 | 320 | 100 |
| 2-162 | 320 | 100 |
| 2-282 | 320 | 80 |
| 3-155 | 320 | 100 |
| 2-283 | 320 | 90 |

TABLE B15

Pre-emergence action against VIOTR

| Example number | Dosage [g/ha] | VIOTR |
| --- | --- | --- |
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 100 |
| 2-164 | 320 | 100 |
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 90 |
| 3-164 | 320 | 100 |
| 1-127 | 320 | 100 |
| 1-65 | 320 | 100 |
| 2-195 | 320 | 100 |
| 2-65 | 320 | 100 |
| 2-22 | 320 | 100 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 100 |
| 1-58 | 320 | 100 |
| 2-58 | 320 | 100 |
| 1-139 | 320 | 100 |
| 2-139 | 320 | 100 |
| 1-146 | 320 | 100 |
| 1-192 | 320 | 100 |
| 1-144 | 320 | 100 |
| 1-284 | 320 | 90 |
| 1-145 | 320 | 100 |
| 1-153 | 320 | 100 |
| 1-114 | 320 | 100 |
| 2-115 | 320 | 100 |
| 1-140 | 320 | 100 |
| 2-137 | 320 | 100 |
| 1-121 | 320 | 100 |
| 1-147 | 320 | 100 |
| 2-121 | 320 | 100 |
| 2-141 | 320 | 100 |
| 1-22 | 320 | 100 |
| 2-14 | 320 | 100 |
| 1-195 | 320 | 100 |
| 2-15 | 320 | 100 |
| 3-65 | 320 | 100 |
| 2-144 | 320 | 100 |
| 1-48 | 320 | 100 |
| 3-7 | 320 | 100 |
| 2-114 | 320 | 100 |
| 2-147 | 320 | 100 |

TABLE B15-continued

Pre-emergence action against VIOTR

| Example number | Dosage [g/ha] | VIOTR |
|---|---|---|
| 2-284 | 320 | 100 |
| 1-116 | 320 | 100 |
| 2-9 | 320 | 100 |
| 2-140 | 320 | 100 |
| 2-123 | 320 | 100 |
| 1-3 | 320 | 90 |
| 3-195 | 320 | 100 |
| 3-197 | 320 | 100 |
| 2-129 | 320 | 100 |
| 3-129 | 320 | 100 |
| 3-137 | 320 | 100 |
| 2-48 | 320 | 100 |
| 3-48 | 320 | 100 |
| 3-16 | 320 | 90 |
| 3-144 | 320 | 100 |
| 3-123 | 320 | 100 |
| 3-192 | 320 | 100 |
| 2-7 | 320 | 100 |
| 3-141 | 320 | 100 |
| 2-127 | 320 | 100 |
| 3-14 | 320 | 100 |
| 1-138 | 320 | 100 |
| 3-50 | 320 | 100 |
| 3-18 | 320 | 100 |
| 3-58 | 320 | 100 |
| 1-280 | 320 | 100 |
| 2-143 | 320 | 100 |
| 2-1 | 320 | 100 |
| 3-1 | 320 | 100 |
| 1-285 | 320 | 100 |
| 2-145 | 320 | 100 |
| 1-123 | 320 | 100 |
| 1-7 | 320 | 100 |
| 3-15 | 320 | 100 |
| 1-18 | 320 | 100 |
| 1-9 | 320 | 100 |
| 1-143 | 320 | 100 |
| 2-163 | 320 | 100 |
| 3-140 | 320 | 100 |
| 1-1 | 320 | 100 |
| 2-153 | 320 | 100 |
| 1-154 | 320 | 100 |
| 1-162 | 320 | 100 |
| 3-163 | 320 | 100 |
| 1-286 | 320 | 100 |
| 3-280 | 320 | 100 |
| 2-285 | 320 | 100 |
| 2-155 | 320 | 100 |
| 3-9 | 320 | 100 |
| 3-134 | 320 | 100 |
| 3-153 | 320 | 100 |
| 1-155 | 320 | 100 |
| 1-287 | 320 | 100 |
| 3-281 | 320 | 100 |
| 1-281 | 320 | 100 |
| 2-281 | 320 | 100 |
| 2-286 | 320 | 100 |
| 2-162 | 320 | 100 |
| 3-282 | 320 | 90 |

TABLE B16

Pre-emergence action against VERPE

| Example number | Dosage [g/ha] | VERPE |
|---|---|---|
| 1-168 | 320 | 100 |
| 2-233 | 320 | 100 |
| 1-16 | 320 | 100 |
| 2-60 | 320 | 100 |
| 1-164 | 320 | 100 |
| 2-18 | 320 | 100 |
| 2-164 | 320 | 100 |

TABLE B16-continued

Pre-emergence action against VERPE

| Example number | Dosage [g/ha] | VERPE |
|---|---|---|
| 1-163 | 320 | 100 |
| 1-165 | 320 | 100 |
| 1-148 | 320 | 100 |
| 1-60 | 320 | 100 |
| 1-67 | 320 | 100 |
| 1-233 | 320 | 100 |
| 3-67 | 320 | 100 |
| 2-16 | 320 | 100 |
| 3-164 | 320 | 100 |
| 1-127 | 320 | 100 |
| 1-65 | 320 | 100 |
| 2-195 | 320 | 100 |
| 2-65 | 320 | 100 |
| 2-22 | 320 | 100 |
| 2-67 | 320 | 100 |
| 1-129 | 320 | 100 |
| 2-116 | 320 | 100 |
| 2-168 | 320 | 100 |
| 3-168 | 320 | 100 |
| 1-137 | 320 | 100 |
| 1-50 | 320 | 100 |
| 2-50 | 320 | 100 |
| 1-141 | 320 | 100 |
| 2-148 | 320 | 100 |
| 1-58 | 320 | 100 |
| 2-58 | 320 | 100 |
| 1-139 | 320 | 100 |
| 2-139 | 320 | 100 |
| 1-146 | 320 | 90 |
| 1-144 | 320 | 100 |
| 1-284 | 320 | 100 |
| 1-145 | 320 | 100 |
| 1-153 | 320 | 100 |
| 1-114 | 320 | 100 |
| 1-115 | 320 | 100 |
| 2-115 | 320 | 90 |
| 1-140 | 320 | 100 |
| 2-137 | 320 | 90 |
| 1-121 | 320 | 100 |
| 1-147 | 320 | 100 |
| 2-121 | 320 | 100 |
| 2-141 | 320 | 100 |
| 1-22 | 320 | 100 |
| 2-14 | 320 | 100 |
| 1-195 | 320 | 100 |
| 2-15 | 320 | 100 |
| 3-65 | 320 | 100 |
| 2-144 | 320 | 100 |
| 1-48 | 320 | 100 |
| 3-7 | 320 | 100 |
| 2-114 | 320 | 90 |
| 2-147 | 320 | 80 |
| 2-284 | 320 | 100 |
| 1-116 | 320 | 100 |
| 2-9 | 320 | 100 |
| 2-140 | 320 | 100 |
| 2-123 | 320 | 100 |
| 1-3 | 320 | 90 |
| 3-195 | 320 | 100 |
| 3-197 | 320 | 100 |
| 2-129 | 320 | 100 |
| 3-129 | 320 | 100 |
| 3-137 | 320 | 90 |
| 2-48 | 320 | 100 |
| 3-48 | 320 | 90 |
| 3-16 | 320 | 100 |
| 3-144 | 320 | 100 |
| 3-123 | 320 | 100 |
| 2-7 | 320 | 100 |
| 3-141 | 320 | 100 |
| 2-127 | 320 | 100 |
| 3-14 | 320 | 100 |
| 1-138 | 320 | 100 |
| 3-50 | 320 | 100 |
| 3-18 | 320 | 90 |
| 3-58 | 320 | 90 |

TABLE B16-continued

Pre-emergence action against VERPE

| Example number | Dosage [g/ha] | VERPE |
|---|---|---|
| 1-280 | 320 | 90 |
| 2-143 | 320 | 100 |
| 1-285 | 320 | 90 |
| 2-145 | 320 | 100 |
| 1-123 | 320 | 100 |
| 1-7 | 320 | 100 |
| 3-15 | 320 | 100 |
| 1-143 | 320 | 100 |
| 3-140 | 320 | 100 |
| 2-153 | 320 | 100 |
| 1-154 | 320 | 90 |
| 2-280 | 320 | 90 |
| 1-162 | 320 | 80 |
| 1-286 | 320 | 90 |
| 2-285 | 320 | 90 |
| 2-155 | 320 | 80 |
| 2-136 | 320 | 90 |
| 3-134 | 320 | 80 |
| 3-135 | 320 | 80 |
| 1-134 | 320 | 90 |
| 1-287 | 320 | 100 |
| 2-135 | 320 | 90 |
| 1-281 | 320 | 100 |
| 2-281 | 320 | 90 |
| 1-135 | 320 | 90 |
| 2-134 | 320 | 100 |
| 1-136 | 320 | 80 |
| 1-14 | 320 | 90 |

TABLE B17

Pre-emergence action against HORMU

| Example number | Dosage [g/ha] | HORMU |
|---|---|---|
| 1-168 | 320 | 100 |
| 2-233 | 320 | 90 |
| 1-16 | 320 | 90 |
| 2-60 | 320 | 100 |
| 1-164 | 320 | 90 |
| 2-18 | 320 | 100 |
| 2-164 | 320 | 80 |
| 1-163 | 320 | 90 |
| 1-165 | 320 | 90 |
| 1-148 | 320 | 80 |
| 1-60 | 320 | 100 |
| 1-67 | 320 | 80 |
| 1-233 | 320 | 100 |
| 3-67 | 320 | 100 |
| 2-16 | 320 | 80 |
| 1-65 | 320 | 90 |
| 2-65 | 320 | 80 |
| 2-67 | 320 | 100 |
| 2-168 | 320 | 90 |
| 3-168 | 320 | 90 |
| 1-139 | 320 | 90 |
| 2-139 | 320 | 80 |
| 1-146 | 320 | 80 |
| 1-192 | 320 | 100 |
| 1-284 | 320 | 80 |
| 1-147 | 320 | 90 |
| 3-65 | 320 | 100 |

2. Post-Emergence Herbicidal Action Against Harmful Plants

Seeds of monocotyledonous and dicotyledonous weed and crop plants are laid out in sandy loam soil in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equating to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). Here, numerous compounds according to the invention showed, at an application rate of 80 g or less per hectare, an activity of at least 80% against a large number of important harmful plants. At the same time, inventive compounds leave Gramineae crops such as barley, wheat, rye, millet/*Sorghum*, corn or rice virtually undamaged when applied post-emergence, even at high active ingredient dosages. In addition, some substances are also harmless to dicotyledonous crops such as soya, cotton, oilseed rape, sugar beet or potatoes. Some of the compounds according to the invention have high selectivity and are therefore suitable for controlling unwanted vegetation in agricultural crops by the post-emergence method. The data of Tables B18 to B34 below illustrate, in an exemplary manner, the pre-emergence herbicidal action of the compounds according to the invention, the herbicidal activity being stated in percent.

TABLE B18

Post-emergence action against ALOMY

| Example number | Dosage [g/ha] | ALOMY |
|---|---|---|
| 1-67 | 80 | 100 |
| 2-67 | 80 | 100 |
| 1-60 | 80 | 100 |
| 1-168 | 80 | 100 |
| 1-233 | 80 | 90 |
| 2-18 | 80 | 100 |
| 2-60 | 80 | 100 |
| 2-129 | 80 | 100 |
| 1-16 | 80 | 90 |
| 1-137 | 80 | 80 |
| 1-50 | 80 | 80 |
| 2-168 | 80 | 100 |
| 1-141 | 80 | 100 |
| 1-165 | 80 | 90 |
| 1-164 | 80 | 90 |
| 2-233 | 80 | 90 |
| 2-116 | 80 | 80 |
| 1-138 | 80 | 100 |
| 2-15 | 80 | 100 |
| 1-192 | 80 | 80 |
| 1-114 | 80 | 80 |
| 1-115 | 80 | 90 |
| 1-129 | 80 | 100 |
| 1-18 | 80 | 100 |
| 2-16 | 80 | 80 |
| 1-121 | 80 | 90 |
| 1-9 | 80 | 100 |
| 2-9 | 80 | 90 |
| 1-58 | 80 | 90 |
| 1-148 | 80 | 80 |
| 3-129 | 80 | 90 |
| 1-153 | 80 | 80 |
| 1-145 | 80 | 90 |
| 2-141 | 80 | 90 |
| 3-141 | 80 | 80 |
| 2-121 | 80 | 80 |
| 1-22 | 80 | 90 |
| 3-16 | 80 | 80 |
| 3-18 | 80 | 80 |
| 2-50 | 80 | 90 |
| 1-7 | 80 | 80 |
| 1-65 | 80 | 80 |
| 1-123 | 80 | 80 |
| 2-123 | 80 | 90 |
| 1-116 | 80 | 90 |

TABLE B18-continued

Post-emergence action against ALOMY

| Example number | Dosage [g/ha] | ALOMY |
| --- | --- | --- |
| 2-22 | 80 | 80 |
| 1-144 | 80 | 90 |
| 2-148 | 80 | 90 |
| 2-140 | 80 | 80 |
| 2-145 | 80 | 80 |

TABLE B19

Post-emergence action against AVEFA

| Example number | Dosage [g/ha] | AVEFA |
| --- | --- | --- |
| 1-67 | 80 | 100 |
| 2-67 | 80 | 100 |
| 1-60 | 80 | 100 |
| 1-168 | 80 | 100 |
| 1-233 | 80 | 90 |
| 2-18 | 80 | 100 |
| 2-60 | 80 | 80 |
| 2-129 | 80 | 100 |
| 1-16 | 80 | 90 |
| 1-137 | 80 | 100 |
| 1-50 | 80 | 100 |
| 2-168 | 80 | 100 |
| 1-141 | 80 | 100 |
| 1-165 | 80 | 90 |
| 1-164 | 80 | 80 |
| 2-233 | 80 | 90 |
| 2-116 | 80 | 90 |
| 1-138 | 80 | 100 |
| 2-15 | 80 | 80 |
| 1-192 | 80 | 80 |
| 1-114 | 80 | 90 |
| 1-129 | 80 | 100 |
| 1-18 | 80 | 100 |
| 2-16 | 80 | 90 |
| 1-121 | 80 | 90 |
| 1-9 | 80 | 100 |
| 2-9 | 80 | 100 |
| 1-58 | 80 | 100 |
| 3-129 | 80 | 90 |
| 1-145 | 80 | 90 |
| 2-141 | 80 | 90 |
| 3-141 | 80 | 100 |
| 1-163 | 80 | 90 |
| 2-121 | 80 | 80 |
| 1-22 | 80 | 90 |
| 3-18 | 80 | 80 |
| 2-50 | 80 | 90 |
| 1-195 | 80 | 80 |
| 1-7 | 80 | 80 |
| 3-7 | 80 | 100 |
| 1-127 | 80 | 80 |
| 1-123 | 80 | 100 |
| 2-123 | 80 | 100 |
| 3-123 | 80 | 100 |
| 1-116 | 80 | 100 |
| 2-7 | 80 | 100 |
| 2-127 | 80 | 90 |
| 3-164 | 80 | 80 |
| 3-9 | 80 | 100 |
| 2-140 | 80 | 80 |
| 3-168 | 80 | 90 |
| 1-284 | 80 | 80 |
| 1-147 | 80 | 100 |
| 2-147 | 80 | 80 |
| 1-287 | 80 | 80 |

TABLE B20

Post-emergence action against CYPES

| Example number | Dosage [g/ha] | CYPES |
| --- | --- | --- |
| 1-67 | 80 | 90 |
| 2-67 | 80 | 80 |
| 1-60 | 80 | 90 |
| 1-168 | 80 | 100 |
| 2-18 | 80 | 90 |
| 2-60 | 80 | 90 |
| 2-129 | 80 | 80 |
| 1-137 | 80 | 90 |
| 1-50 | 80 | 80 |
| 2-168 | 80 | 100 |
| 1-141 | 80 | 90 |
| 1-164 | 80 | 90 |
| 2-116 | 80 | 80 |
| 1-138 | 80 | 90 |
| 2-15 | 80 | 90 |
| 1-192 | 80 | 80 |
| 1-114 | 80 | 80 |
| 3-67 | 80 | 80 |
| 1-115 | 80 | 90 |
| 1-129 | 80 | 80 |
| 1-18 | 80 | 90 |
| 1-9 | 80 | 80 |
| 2-9 | 80 | 90 |
| 1-58 | 80 | 90 |
| 1-148 | 80 | 90 |
| 3-129 | 80 | 80 |
| 1-145 | 80 | 100 |
| 3-141 | 80 | 80 |
| 2-121 | 80 | 80 |
| 3-18 | 80 | 90 |
| 1-195 | 80 | 80 |
| 1-65 | 80 | 90 |
| 3-7 | 80 | 80 |
| 2-58 | 80 | 90 |
| 1-127 | 80 | 80 |
| 2-137 | 80 | 90 |
| 2-127 | 80 | 90 |
| 3-164 | 80 | 90 |
| 2-14 | 80 | 90 |
| 3-65 | 80 | 80 |
| 3-9 | 80 | 80 |
| 1-48 | 80 | 100 |
| 2-48 | 80 | 100 |
| 1-140 | 80 | 90 |
| 2-140 | 80 | 80 |
| 2-114 | 80 | 90 |
| 2-115 | 80 | 80 |
| 1-280 | 80 | 90 |
| 3-50 | 80 | 80 |
| 3-58 | 80 | 100 |
| 2-164 | 80 | 90 |
| 3-14 | 80 | 90 |
| 3-168 | 80 | 90 |
| 1-134 | 80 | 90 |
| 3-197 | 80 | 90 |
| 3-48 | 80 | 90 |
| 2-195 | 80 | 90 |
| 3-192 | 80 | 80 |
| 3-134 | 80 | 80 |
| 1-162 | 80 | 80 |
| 3-195 | 80 | 80 |
| 2-135 | 80 | 80 |
| 1-136 | 80 | 80 |

TABLE B21

Post-emergence action against DIGSA

| Example number | Dosage [g/ha] | DIGSA |
| --- | --- | --- |
| 1-233 | 80 | 100 |
| 1-16 | 80 | 90 |
| 1-165 | 80 | 100 |

TABLE B21-continued

Post-emergence action against DIGSA

| Example number | Dosage [g/ha] | DIGSA |
|---|---|---|
| 2-233 | 80 | 90 |
| 2-16 | 80 | 90 |
| 1-153 | 80 | 90 |
| 1-163 | 80 | 100 |
| 1-22 | 80 | 100 |
| 3-16 | 80 | 90 |
| 2-22 | 80 | 90 |
| 2-284 | 80 | 90 |
| 1-146 | 80 | 80 |
| 1-284 | 80 | 90 |
| 2-163 | 80 | 100 |
| 2-153 | 80 | 100 |
| 3-280 | 80 | 80 |
| 1-154 | 80 | 80 |
| 3-153 | 80 | 80 |

TABLE B22

Post-emergence action against ECHCG

| Example number | Dosage [g/ha] | ECHCG |
|---|---|---|
| 1-67 | 80 | 100 |
| 2-67 | 80 | 100 |
| 1-60 | 80 | 100 |
| 1-168 | 80 | 100 |
| 1-233 | 80 | 100 |
| 2-18 | 80 | 100 |
| 2-60 | 80 | 100 |
| 2-129 | 80 | 90 |
| 1-16 | 80 | 90 |
| 1-137 | 80 | 90 |
| 1-50 | 80 | 90 |
| 2-168 | 80 | 100 |
| 1-141 | 80 | 100 |
| 1-165 | 80 | 90 |
| 1-164 | 80 | 100 |
| 2-233 | 80 | 90 |
| 2-116 | 80 | 90 |
| 1-138 | 80 | 90 |
| 2-15 | 80 | 90 |
| 1-192 | 80 | 100 |
| 1-114 | 80 | 90 |
| 3-67 | 80 | 100 |
| 1-115 | 80 | 90 |
| 1-129 | 80 | 90 |
| 1-18 | 80 | 90 |
| 2-16 | 80 | 90 |
| 1-121 | 80 | 90 |
| 1-9 | 80 | 90 |
| 2-9 | 80 | 90 |
| 1-58 | 80 | 100 |
| 1-148 | 80 | 100 |
| 3-129 | 80 | 100 |
| 1-153 | 80 | 90 |
| 1-145 | 80 | 100 |
| 2-141 | 80 | 90 |
| 3-141 | 80 | 100 |
| 1-163 | 80 | 90 |
| 2-121 | 80 | 100 |
| 1-22 | 80 | 90 |
| 3-16 | 80 | 90 |
| 3-18 | 80 | 80 |
| 2-50 | 80 | 100 |
| 1-195 | 80 | 90 |
| 1-7 | 80 | 90 |
| 1-65 | 80 | 100 |
| 3-7 | 80 | 100 |
| 2-58 | 80 | 90 |
| 1-127 | 80 | 100 |
| 1-123 | 80 | 100 |
| 2-123 | 80 | 100 |
| 3-123 | 80 | 100 |

TABLE B22-continued

Post-emergence action against ECHCG

| Example number | Dosage [g/ha] | ECHCG |
|---|---|---|
| 1-116 | 80 | 90 |
| 2-7 | 80 | 100 |
| 2-137 | 80 | 90 |
| 2-127 | 80 | 100 |
| 3-164 | 80 | 100 |
| 2-14 | 80 | 100 |
| 2-22 | 80 | 90 |
| 3-65 | 80 | 90 |
| 3-9 | 80 | 100 |
| 1-144 | 80 | 90 |
| 2-284 | 80 | 90 |
| 2-148 | 80 | 90 |
| 1-48 | 80 | 90 |
| 2-48 | 80 | 90 |
| 1-140 | 80 | 100 |
| 2-140 | 80 | 100 |
| 2-114 | 80 | 90 |
| 2-115 | 80 | 90 |
| 1-280 | 80 | 90 |
| 3-50 | 80 | 100 |
| 3-58 | 80 | 100 |
| 1-146 | 80 | 100 |
| 2-164 | 80 | 100 |
| 3-137 | 80 | 90 |
| 3-14 | 80 | 100 |
| 2-65 | 80 | 80 |
| 3-168 | 80 | 100 |
| 1-134 | 80 | 90 |
| 1-284 | 80 | 100 |
| 3-197 | 80 | 90 |
| 3-48 | 80 | 90 |
| 2-280 | 80 | 90 |
| 2-144 | 80 | 100 |
| 3-144 | 80 | 80 |
| 2-145 | 80 | 100 |
| 3-15 | 80 | 100 |
| 2-195 | 80 | 90 |
| 2-163 | 80 | 90 |
| 3-192 | 80 | 100 |
| 2-134 | 80 | 90 |
| 3-134 | 80 | 90 |
| 2-1 | 80 | 100 |
| 2-153 | 80 | 90 |
| 1-162 | 80 | 90 |
| 3-280 | 80 | 80 |
| 1-147 | 80 | 100 |
| 3-195 | 80 | 90 |
| 1-1 | 80 | 100 |
| 2-135 | 80 | 90 |
| 2-147 | 80 | 80 |
| 1-139 | 80 | 90 |
| 3-140 | 80 | 100 |
| 3-136 | 80 | 80 |
| 2-139 | 80 | 90 |
| 3-163 | 80 | 80 |
| 3-1 | 80 | 100 |
| 1-287 | 80 | 90 |
| 1-135 | 80 | 80 |
| 3-135 | 80 | 80 |
| 2-286 | 80 | 80 |
| 3-3 | 80 | 100 |

TABLE B23

Post-emergence action against LOLMU

| Example number | Dosage [g/ha] | LOLMU |
|---|---|---|
| 2-129 | 80 | 90 |
| 1-137 | 80 | 100 |
| 1-50 | 80 | 90 |
| 1-141 | 80 | 100 |
| 2-116 | 80 | 90 |

TABLE B23-continued

Post-emergence action against LOLMU

| Example number | Dosage [g/ha] | LOLMU |
|---|---|---|
| 1-138 | 80 | 100 |
| 2-15 | 80 | 90 |
| 1-114 | 80 | 100 |
| 1-115 | 80 | 90 |
| 1-129 | 80 | 80 |
| 1-18 | 80 | 90 |
| 1-121 | 80 | 90 |
| 1-9 | 80 | 90 |
| 1-58 | 80 | 80 |
| 2-141 | 80 | 90 |
| 1-195 | 80 | 90 |
| 1-116 | 80 | 100 |
| 2-14 | 80 | 80 |

TABLE B24

Post-emergence action against LOLRI

| Example number | Dosage [g/ha] | LOLRI |
|---|---|---|
| 1-67 | 80 | 100 |
| 2-67 | 80 | 80 |
| 1-60 | 80 | 100 |
| 1-168 | 80 | 100 |
| 1-233 | 80 | 90 |
| 2-18 | 80 | 100 |
| 2-60 | 80 | 90 |
| 1-16 | 80 | 80 |
| 2-168 | 80 | 100 |
| 1-165 | 80 | 80 |
| 1-164 | 80 | 90 |
| 1-192 | 80 | 100 |
| 3-67 | 80 | 80 |
| 1-148 | 80 | 80 |
| 1-145 | 80 | 80 |
| 1-144 | 80 | 80 |
| 2-148 | 80 | 80 |
| 1-140 | 80 | 80 |
| 2-147 | 80 | 80 |

TABLE B25

Post-emergence action against SETVI

| Example number | Dosage [g/ha] | SETVI |
|---|---|---|
| 1-67 | 80 | 100 |
| 2-67 | 80 | 100 |
| 1-60 | 80 | 100 |
| 1-168 | 80 | 100 |
| 1-233 | 80 | 90 |
| 2-18 | 80 | 100 |
| 2-60 | 80 | 100 |
| 2-129 | 80 | 100 |
| 1-16 | 80 | 90 |
| 1-137 | 80 | 100 |
| 1-50 | 80 | 100 |
| 2-168 | 80 | 100 |
| 1-141 | 80 | 100 |
| 1-165 | 80 | 100 |
| 1-164 | 80 | 90 |
| 2-233 | 80 | 90 |
| 2-116 | 80 | 90 |
| 1-138 | 80 | 90 |
| 2-15 | 80 | 100 |
| 1-192 | 80 | 100 |
| 1-114 | 80 | 80 |
| 3-67 | 80 | 100 |
| 1-115 | 80 | 90 |
| 1-129 | 80 | 100 |
| 1-18 | 80 | 100 |

TABLE B25-continued

Post-emergence action against SETVI

| Example number | Dosage [g/ha] | SETVI |
|---|---|---|
| 2-16 | 80 | 90 |
| 1-121 | 80 | 90 |
| 1-9 | 80 | 100 |
| 2-9 | 80 | 90 |
| 1-58 | 80 | 100 |
| 1-148 | 80 | 100 |
| 3-129 | 80 | 100 |
| 1-153 | 80 | 100 |
| 1-145 | 80 | 100 |
| 2-141 | 80 | 90 |
| 3-141 | 80 | 100 |
| 1-163 | 80 | 80 |
| 2-121 | 80 | 90 |
| 1-22 | 80 | 90 |
| 3-16 | 80 | 90 |
| 3-18 | 80 | 100 |
| 2-50 | 80 | 100 |
| 1-195 | 80 | 90 |
| 1-7 | 80 | 90 |
| 1-65 | 80 | 100 |
| 3-7 | 80 | 100 |
| 2-58 | 80 | 100 |
| 1-127 | 80 | 80 |
| 1-123 | 80 | 100 |
| 2-123 | 80 | 100 |
| 3-123 | 80 | 90 |
| 1-116 | 80 | 100 |
| 2-7 | 80 | 100 |
| 2-137 | 80 | 100 |
| 2-127 | 80 | 90 |
| 3-164 | 80 | 100 |
| 2-14 | 80 | 90 |
| 2-22 | 80 | 80 |
| 3-65 | 80 | 100 |
| 3-9 | 80 | 100 |
| 1-144 | 80 | 100 |
| 2-284 | 80 | 100 |
| 2-148 | 80 | 90 |
| 1-48 | 80 | 80 |
| 2-48 | 80 | 80 |
| 1-140 | 80 | 100 |
| 2-115 | 80 | 90 |
| 1-280 | 80 | 80 |
| 3-50 | 80 | 100 |
| 3-58 | 80 | 80 |
| 1-146 | 80 | 100 |
| 2-164 | 80 | 100 |
| 3-137 | 80 | 100 |
| 3-14 | 80 | 100 |
| 2-65 | 80 | 100 |
| 3-168 | 80 | 100 |
| 1-134 | 80 | 80 |
| 3-197 | 80 | 90 |
| 3-48 | 80 | 80 |
| 2-280 | 80 | 90 |
| 2-144 | 80 | 100 |
| 3-144 | 80 | 100 |
| 2-145 | 80 | 100 |
| 3-15 | 80 | 100 |
| 2-195 | 80 | 90 |
| 2-163 | 80 | 80 |
| 3-192 | 80 | 100 |
| 2-134 | 80 | 80 |
| 2-1 | 80 | 80 |
| 1-162 | 80 | 80 |
| 1-147 | 80 | 100 |
| 3-195 | 80 | 90 |
| 2-147 | 80 | 80 |

TABLE B26

Post-emergence action against ABUTH

| Example number | Dosage [g/ha] | ABUTH |
|---|---|---|
| 1-67 | 80 | 100 |
| 2-67 | 80 | 100 |
| 1-60 | 80 | 90 |
| 1-168 | 80 | 100 |
| 1-233 | 80 | 100 |
| 2-18 | 80 | 100 |
| 2-60 | 80 | 100 |
| 2-129 | 80 | 80 |
| 1-16 | 80 | 100 |
| 1-137 | 80 | 90 |
| 1-50 | 80 | 100 |
| 2-168 | 80 | 100 |
| 1-141 | 80 | 100 |
| 1-165 | 80 | 90 |
| 1-164 | 80 | 100 |
| 2-233 | 80 | 100 |
| 2-116 | 80 | 80 |
| 1-138 | 80 | 80 |
| 2-15 | 80 | 100 |
| 1-192 | 80 | 100 |
| 1-114 | 80 | 80 |
| 3-67 | 80 | 100 |
| 1-115 | 80 | 90 |
| 1-129 | 80 | 90 |
| 1-18 | 80 | 80 |
| 2-16 | 80 | 100 |
| 1-121 | 80 | 90 |
| 1-9 | 80 | 90 |
| 2-9 | 80 | 90 |
| 1-58 | 80 | 100 |
| 1-148 | 80 | 100 |
| 3-129 | 80 | 90 |
| 1-153 | 80 | 100 |
| 1-145 | 80 | 100 |
| 2-141 | 80 | 90 |
| 3-141 | 80 | 80 |
| 1-163 | 80 | 90 |
| 2-121 | 80 | 100 |
| 1-22 | 80 | 90 |
| 3-16 | 80 | 100 |
| 3-18 | 80 | 80 |
| 2-50 | 80 | 90 |
| 1-195 | 80 | 80 |
| 1-7 | 80 | 90 |
| 1-65 | 80 | 100 |
| 3-7 | 80 | 100 |
| 2-58 | 80 | 100 |
| 1-127 | 80 | 90 |
| 1-123 | 80 | 100 |
| 2-123 | 80 | 100 |
| 3-123 | 80 | 80 |
| 1-116 | 80 | 90 |
| 2-7 | 80 | 100 |
| 2-137 | 80 | 90 |
| 2-127 | 80 | 100 |
| 3-164 | 80 | 90 |
| 2-14 | 80 | 100 |
| 2-22 | 80 | 90 |
| 3-65 | 80 | 100 |
| 3-9 | 80 | 80 |
| 1-144 | 80 | 100 |
| 2-284 | 80 | 100 |
| 2-148 | 80 | 90 |
| 1-48 | 80 | 100 |
| 2-48 | 80 | 100 |
| 1-140 | 80 | 100 |
| 2-140 | 80 | 100 |
| 2-114 | 80 | 90 |
| 2-115 | 80 | 90 |
| 1-280 | 80 | 80 |
| 3-50 | 80 | 100 |
| 3-58 | 80 | 100 |
| 1-146 | 80 | 100 |
| 2-164 | 80 | 100 |
| 3-137 | 80 | 90 |
| 3-14 | 80 | 90 |
| 2-65 | 80 | 100 |
| 3-168 | 80 | 100 |
| 1-134 | 80 | 80 |
| 1-284 | 80 | 100 |
| 3-197 | 80 | 90 |
| 3-48 | 80 | 100 |
| 2-280 | 80 | 90 |
| 2-144 | 80 | 90 |
| 3-144 | 80 | 90 |
| 2-145 | 80 | 100 |
| 3-15 | 80 | 90 |
| 2-195 | 80 | 80 |
| 2-163 | 80 | 90 |
| 3-192 | 80 | 100 |
| 3-134 | 80 | 80 |
| 2-1 | 80 | 80 |
| 2-153 | 80 | 100 |
| 1-162 | 80 | 100 |
| 3-280 | 80 | 100 |
| 1-147 | 80 | 100 |
| 1-1 | 80 | 100 |
| 2-135 | 80 | 80 |
| 2-147 | 80 | 90 |
| 1-154 | 80 | 90 |
| 1-139 | 80 | 90 |
| 3-140 | 80 | 100 |
| 2-139 | 80 | 90 |
| 3-163 | 80 | 80 |
| 3-1 | 80 | 80 |
| 1-3 | 80 | 100 |
| 1-287 | 80 | 80 |
| 2-286 | 80 | 80 |
| 1-155 | 80 | 90 |
| 3-153 | 80 | 100 |
| 2-154 | 80 | 90 |
| 1-285 | 80 | 90 |
| 2-285 | 80 | 90 |
| 1-286 | 80 | 90 |
| 1-14 | 80 | 90 |
| 3-282 | 80 | 80 |
| 3-155 | 80 | 80 |
| 2-283 | 80 | 80 |

TABLE B27

Post-emergence action against AMARE

| Example number | Dosage [g/ha] | AMARE |
|---|---|---|
| 1-67 | 80 | 100 |
| 2-67 | 80 | 100 |
| 1-60 | 80 | 100 |
| 1-168 | 80 | 100 |
| 1-233 | 80 | 90 |
| 2-18 | 80 | 100 |
| 2-60 | 80 | 100 |
| 2-129 | 80 | 100 |
| 1-16 | 80 | 100 |
| 1-137 | 80 | 90 |
| 1-50 | 80 | 90 |
| 2-168 | 80 | 100 |
| 1-141 | 80 | 100 |
| 1-165 | 80 | 90 |
| 1-164 | 80 | 100 |
| 2-233 | 80 | 100 |
| 2-116 | 80 | 90 |
| 1-138 | 80 | 80 |
| 2-15 | 80 | 90 |
| 1-192 | 80 | 100 |
| 3-67 | 80 | 100 |
| 1-115 | 80 | 90 |
| 1-129 | 80 | 100 |
| 1-18 | 80 | 90 |

TABLE B27-continued

Post-emergence action against AMARE

| Example number | Dosage [g/ha] | AMARE |
|---|---|---|
| 2-16 | 80 | 100 |
| 1-121 | 80 | 90 |
| 1-9 | 80 | 90 |
| 2-9 | 80 | 100 |
| 1-58 | 80 | 100 |
| 1-148 | 80 | 100 |
| 3-129 | 80 | 90 |
| 1-153 | 80 | 100 |
| 1-145 | 80 | 100 |
| 2-141 | 80 | 90 |
| 3-141 | 80 | 100 |
| 1-163 | 80 | 90 |
| 2-121 | 80 | 100 |
| 1-22 | 80 | 90 |
| 3-16 | 80 | 100 |
| 2-50 | 80 | 100 |
| 1-7 | 80 | 100 |
| 1-65 | 80 | 100 |
| 3-7 | 80 | 100 |
| 2-58 | 80 | 100 |
| 1-127 | 80 | 100 |
| 1-123 | 80 | 100 |
| 2-123 | 80 | 100 |
| 3-123 | 80 | 100 |
| 1-116 | 80 | 90 |
| 2-7 | 80 | 100 |
| 2-137 | 80 | 100 |
| 2-127 | 80 | 100 |
| 3-164 | 80 | 100 |
| 2-14 | 80 | 100 |
| 2-22 | 80 | 80 |
| 3-65 | 80 | 90 |
| 3-9 | 80 | 100 |
| 1-144 | 80 | 100 |
| 2-284 | 80 | 100 |
| 2-148 | 80 | 90 |
| 1-48 | 80 | 100 |
| 2-48 | 80 | 90 |
| 1-140 | 80 | 90 |
| 2-114 | 80 | 100 |
| 2-115 | 80 | 90 |
| 1-280 | 80 | 90 |
| 3-50 | 80 | 100 |
| 3-58 | 80 | 100 |
| 1-146 | 80 | 100 |
| 2-164 | 80 | 100 |
| 3-137 | 80 | 100 |
| 3-14 | 80 | 100 |
| 2-65 | 80 | 100 |
| 3-168 | 80 | 100 |
| 1-134 | 80 | 90 |
| 1-284 | 80 | 100 |
| 3-197 | 80 | 100 |
| 2-280 | 80 | 100 |
| 2-144 | 80 | 100 |
| 3-144 | 80 | 90 |
| 2-145 | 80 | 100 |
| 3-15 | 80 | 90 |
| 2-163 | 80 | 100 |
| 3-192 | 80 | 80 |
| 2-134 | 80 | 90 |
| 3-134 | 80 | 90 |
| 2-1 | 80 | 100 |
| 2-153 | 80 | 90 |
| 1-162 | 80 | 100 |
| 3-280 | 80 | 100 |
| 1-147 | 80 | 100 |
| 1-1 | 80 | 100 |
| 2-135 | 80 | 90 |
| 2-147 | 80 | 80 |
| 1-154 | 80 | 90 |
| 1-139 | 80 | 100 |
| 1-136 | 80 | 90 |
| 3-140 | 80 | 80 |
| 3-136 | 80 | 80 |
| 2-139 | 80 | 100 |
| 3-163 | 80 | 100 |
| 3-1 | 80 | 90 |
| 1-3 | 80 | 100 |
| 1-287 | 80 | 90 |
| 1-281 | 80 | 90 |
| 2-281 | 80 | 90 |
| 1-135 | 80 | 90 |
| 3-135 | 80 | 90 |
| 2-286 | 80 | 90 |
| 1-155 | 80 | 90 |
| 3-153 | 80 | 100 |
| 2-154 | 80 | 100 |
| 2-162 | 80 | 90 |
| 1-285 | 80 | 90 |
| 2-285 | 80 | 90 |
| 1-286 | 80 | 90 |
| 1-14 | 80 | 80 |
| 3-282 | 80 | 80 |
| 3-155 | 80 | 90 |
| 3-3 | 80 | 100 |
| 1-282 | 80 | 80 |
| 3-281 | 80 | 80 |
| 2-155 | 80 | 80 |

TABLE B28

Post-emergence action against MATIN

| Example number | Dosage [g/ha] | MATIN |
|---|---|---|
| 1-67 | 80 | 100 |
| 2-67 | 80 | 100 |
| 1-60 | 80 | 100 |
| 1-168 | 80 | 100 |
| 1-233 | 80 | 90 |
| 2-18 | 80 | 100 |
| 2-60 | 80 | 90 |
| 2-129 | 80 | 100 |
| 1-16 | 80 | 100 |
| 1-137 | 80 | 90 |
| 1-50 | 80 | 100 |
| 2-168 | 80 | 100 |
| 1-141 | 80 | 90 |
| 1-165 | 80 | 90 |
| 1-164 | 80 | 100 |
| 2-233 | 80 | 90 |
| 2-116 | 80 | 90 |
| 1-138 | 80 | 100 |
| 2-15 | 80 | 90 |
| 1-192 | 80 | 100 |
| 1-114 | 80 | 80 |
| 3-67 | 80 | 100 |
| 1-115 | 80 | 100 |
| 1-129 | 80 | 90 |
| 1-18 | 80 | 100 |
| 2-16 | 80 | 100 |
| 1-121 | 80 | 100 |
| 1-9 | 80 | 100 |
| 2-9 | 80 | 100 |
| 1-58 | 80 | 100 |
| 1-148 | 80 | 100 |
| 3-129 | 80 | 100 |
| 1-153 | 80 | 100 |
| 2-141 | 80 | 80 |
| 3-141 | 80 | 100 |
| 1-163 | 80 | 90 |
| 2-121 | 80 | 100 |
| 1-22 | 80 | 90 |
| 3-16 | 80 | 90 |
| 3-18 | 80 | 90 |
| 2-50 | 80 | 100 |
| 1-195 | 80 | 90 |
| 1-7 | 80 | 100 |

TABLE B28-continued

Post-emergence action against MATIN

| Example number | Dosage [g/ha] | MATIN |
|---|---|---|
| 1-65 | 80 | 100 |
| 3-7 | 80 | 100 |
| 2-58 | 80 | 100 |
| 1-127 | 80 | 100 |
| 1-123 | 80 | 100 |
| 2-123 | 80 | 100 |
| 3-123 | 80 | 100 |
| 1-116 | 80 | 90 |
| 2-7 | 80 | 100 |
| 2-137 | 80 | 100 |
| 2-127 | 80 | 90 |
| 3-164 | 80 | 100 |
| 2-14 | 80 | 100 |
| 2-22 | 80 | 90 |
| 3-65 | 80 | 90 |
| 3-9 | 80 | 100 |
| 1-144 | 80 | 90 |
| 2-284 | 80 | 90 |
| 2-148 | 80 | 90 |
| 1-48 | 80 | 100 |
| 2-48 | 80 | 100 |
| 1-140 | 80 | 100 |
| 2-140 | 80 | 90 |
| 2-114 | 80 | 80 |
| 2-115 | 80 | 100 |
| 1-280 | 80 | 90 |
| 3-50 | 80 | 100 |
| 3-58 | 80 | 100 |
| 1-146 | 80 | 90 |
| 2-164 | 80 | 100 |
| 3-137 | 80 | 100 |
| 3-14 | 80 | 100 |
| 2-65 | 80 | 100 |
| 3-168 | 80 | 100 |
| 1-134 | 80 | 100 |
| 1-284 | 80 | 100 |
| 3-197 | 80 | 90 |
| 3-48 | 80 | 100 |
| 2-280 | 80 | 90 |
| 2-144 | 80 | 90 |
| 3-144 | 80 | 90 |
| 3-15 | 80 | 100 |
| 2-195 | 80 | 90 |
| 2-163 | 80 | 90 |
| 3-192 | 80 | 100 |
| 2-134 | 80 | 90 |
| 3-134 | 80 | 90 |
| 2-1 | 80 | 90 |
| 2-153 | 80 | 100 |
| 3-280 | 80 | 90 |
| 1-147 | 80 | 90 |
| 3-195 | 80 | 90 |
| 1-1 | 80 | 80 |
| 2-135 | 80 | 90 |
| 2-147 | 80 | 100 |
| 1-154 | 80 | 80 |
| 1-139 | 80 | 90 |
| 1-136 | 80 | 90 |
| 3-140 | 80 | 90 |
| 3-136 | 80 | 90 |
| 2-139 | 80 | 90 |
| 3-163 | 80 | 90 |
| 3-1 | 80 | 100 |
| 1-3 | 80 | 90 |
| 1-281 | 80 | 80 |
| 2-281 | 80 | 80 |
| 1-135 | 80 | 90 |
| 3-135 | 80 | 80 |
| 1-155 | 80 | 80 |
| 3-153 | 80 | 100 |
| 2-285 | 80 | 80 |
| 2-136 | 80 | 90 |

TABLE B29

Post-emergence action against PHBPU

| Example number | Dosage [g/ha] | PHBPU |
|---|---|---|
| 1-67 | 80 | 80 |
| 2-67 | 80 | 100 |
| 1-60 | 80 | 90 |
| 1-168 | 80 | 100 |
| 1-233 | 80 | 100 |
| 2-18 | 80 | 100 |
| 2-60 | 80 | 100 |
| 2-129 | 80 | 100 |
| 1-16 | 80 | 100 |
| 1-137 | 80 | 100 |
| 1-50 | 80 | 100 |
| 2-168 | 80 | 100 |
| 1-141 | 80 | 100 |
| 1-165 | 80 | 90 |
| 1-164 | 80 | 90 |
| 2-233 | 80 | 90 |
| 2-116 | 80 | 100 |
| 1-138 | 80 | 100 |
| 2-15 | 80 | 80 |
| 1-192 | 80 | 80 |
| 1-114 | 80 | 90 |
| 3-67 | 80 | 100 |
| 1-115 | 80 | 90 |
| 1-129 | 80 | 100 |
| 1-18 | 80 | 100 |
| 2-16 | 80 | 100 |
| 1-121 | 80 | 90 |
| 1-9 | 80 | 100 |
| 2-9 | 80 | 100 |
| 1-58 | 80 | 100 |
| 1-148 | 80 | 100 |
| 3-129 | 80 | 100 |
| 1-153 | 80 | 90 |
| 1-145 | 80 | 100 |
| 2-141 | 80 | 90 |
| 3-141 | 80 | 100 |
| 1-163 | 80 | 90 |
| 2-121 | 80 | 90 |
| 1-22 | 80 | 90 |
| 3-16 | 80 | 90 |
| 3-18 | 80 | 90 |
| 2-50 | 80 | 100 |
| 1-195 | 80 | 90 |
| 1-7 | 80 | 100 |
| 1-65 | 80 | 100 |
| 3-7 | 80 | 90 |
| 2-58 | 80 | 100 |
| 1-127 | 80 | 100 |
| 1-123 | 80 | 90 |
| 2-123 | 80 | 100 |
| 3-123 | 80 | 90 |
| 1-116 | 80 | 90 |
| 2-7 | 80 | 80 |
| 2-137 | 80 | 90 |
| 2-127 | 80 | 100 |
| 3-164 | 80 | 100 |
| 2-14 | 80 | 90 |
| 2-22 | 80 | 100 |
| 3-65 | 80 | 90 |
| 3-9 | 80 | 100 |
| 1-144 | 80 | 100 |
| 2-284 | 80 | 90 |
| 2-148 | 80 | 90 |
| 1-48 | 80 | 90 |
| 2-48 | 80 | 100 |
| 1-140 | 80 | 90 |
| 2-140 | 80 | 90 |
| 2-114 | 80 | 90 |
| 2-115 | 80 | 90 |
| 1-280 | 80 | 80 |
| 3-50 | 80 | 100 |
| 3-58 | 80 | 90 |
| 1-146 | 80 | 80 |
| 2-164 | 80 | 100 |
| 3-137 | 80 | 100 |
| 3-14 | 80 | 90 |

TABLE B29-continued

Post-emergence action against PHBPU

| Example number | Dosage [g/ha] | PHBPU |
|---|---|---|
| 2-65 | 80 | 90 |
| 3-168 | 80 | 100 |
| 1-134 | 80 | 90 |
| 1-284 | 80 | 90 |
| 3-197 | 80 | 100 |
| 3-48 | 80 | 100 |
| 2-280 | 80 | 100 |
| 2-144 | 80 | 100 |
| 3-144 | 80 | 100 |
| 2-145 | 80 | 100 |
| 3-15 | 80 | 90 |
| 2-195 | 80 | 90 |
| 2-163 | 80 | 90 |
| 3-192 | 80 | 80 |
| 2-134 | 80 | 80 |
| 3-134 | 80 | 90 |
| 2-1 | 80 | 90 |
| 2-153 | 80 | 80 |
| 1-162 | 80 | 100 |
| 3-280 | 80 | 80 |
| 1-147 | 80 | 80 |
| 3-195 | 80 | 90 |
| 1-1 | 80 | 90 |
| 2-135 | 80 | 90 |
| 2-147 | 80 | 90 |
| 1-154 | 80 | 80 |
| 1-139 | 80 | 100 |
| 1-136 | 80 | 90 |
| 3-140 | 80 | 90 |
| 3-136 | 80 | 90 |
| 2-139 | 80 | 100 |
| 3-163 | 80 | 90 |
| 3-1 | 80 | 80 |
| 1-3 | 80 | 90 |
| 1-287 | 80 | 90 |
| 1-281 | 80 | 90 |
| 2-281 | 80 | 100 |
| 3-135 | 80 | 90 |
| 2-286 | 80 | 90 |
| 1-155 | 80 | 80 |
| 2-154 | 80 | 90 |
| 2-162 | 80 | 100 |
| 1-285 | 80 | 80 |
| 2-136 | 80 | 90 |
| 3-282 | 80 | 90 |

TABLE B30

Post-emergence action against POLCO

| Example number | Dosage [g/ha] | POLCO |
|---|---|---|
| 1-67 | 80 | 100 |
| 2-67 | 80 | 100 |
| 1-60 | 80 | 100 |
| 1-168 | 80 | 100 |
| 1-233 | 80 | 90 |
| 2-18 | 80 | 100 |
| 2-60 | 80 | 90 |
| 2-129 | 80 | 100 |
| 1-16 | 80 | 100 |
| 1-137 | 80 | 100 |
| 1-50 | 80 | 100 |
| 2-168 | 80 | 100 |
| 1-141 | 80 | 100 |
| 1-165 | 80 | 100 |
| 1-164 | 80 | 90 |
| 2-233 | 80 | 80 |
| 2-116 | 80 | 90 |
| 1-138 | 80 | 80 |
| 2-15 | 80 | 100 |
| 1-192 | 80 | 100 |
| 1-114 | 80 | 90 |
| 3-67 | 80 | 80 |
| 1-115 | 80 | 100 |
| 2-16 | 80 | 80 |
| 1-121 | 80 | 80 |
| 2-9 | 80 | 100 |
| 1-148 | 80 | 80 |
| 1-153 | 80 | 80 |
| 2-141 | 80 | 90 |
| 1-163 | 80 | 100 |
| 3-16 | 80 | 90 |
| 3-18 | 80 | 80 |
| 2-50 | 80 | 90 |
| 1-195 | 80 | 90 |
| 1-7 | 80 | 80 |
| 1-65 | 80 | 100 |
| 3-7 | 80 | 80 |
| 2-58 | 80 | 90 |
| 3-123 | 80 | 90 |
| 2-7 | 80 | 100 |
| 2-137 | 80 | 90 |
| 3-164 | 80 | 80 |
| 3-65 | 80 | 80 |
| 2-284 | 80 | 80 |
| 1-48 | 80 | 90 |
| 2-48 | 80 | 80 |
| 2-140 | 80 | 80 |
| 2-114 | 80 | 90 |
| 2-115 | 80 | 100 |
| 2-164 | 80 | 80 |
| 3-137 | 80 | 90 |
| 2-65 | 80 | 100 |
| 3-48 | 80 | 80 |
| 2-280 | 80 | 80 |
| 2-145 | 80 | 80 |
| 2-195 | 80 | 90 |
| 2-134 | 80 | 80 |
| 2-1 | 80 | 100 |
| 2-153 | 80 | 80 |
| 3-195 | 80 | 90 |
| 1-1 | 80 | 80 |

TABLE B31

Post-emergence action against STEME

| Example number | Dosage [g/ha] | STEME |
|---|---|---|
| 1-67 | 80 | 100 |
| 2-67 | 80 | 100 |
| 1-60 | 80 | 100 |
| 1-168 | 80 | 100 |
| 1-233 | 80 | 90 |
| 2-18 | 80 | 100 |
| 2-60 | 80 | 100 |
| 2-129 | 80 | 100 |
| 1-16 | 80 | 100 |
| 1-137 | 80 | 100 |
| 1-50 | 80 | 100 |
| 2-168 | 80 | 100 |
| 1-141 | 80 | 100 |
| 1-165 | 80 | 100 |
| 1-164 | 80 | 90 |
| 2-233 | 80 | 90 |
| 2-116 | 80 | 90 |
| 1-138 | 80 | 100 |
| 2-15 | 80 | 100 |
| 1-114 | 80 | 100 |
| 3-67 | 80 | 100 |
| 1-115 | 80 | 100 |
| 1-129 | 80 | 100 |
| 1-18 | 80 | 100 |
| 2-16 | 80 | 100 |
| 1-121 | 80 | 100 |

TABLE B31-continued

Post-emergence action against STEME

| Example number | Dosage [g/ha] | STEME |
|---|---|---|
| 1-9 | 80 | 100 |
| 2-9 | 80 | 100 |
| 1-58 | 80 | 100 |
| 1-148 | 80 | 100 |
| 3-129 | 80 | 100 |
| 1-153 | 80 | 100 |
| 1-145 | 80 | 100 |
| 3-141 | 80 | 100 |
| 1-163 | 80 | 100 |
| 2-121 | 80 | 90 |
| 1-22 | 80 | 90 |
| 3-16 | 80 | 90 |
| 3-18 | 80 | 100 |
| 2-50 | 80 | 100 |
| 1-195 | 80 | 100 |
| 1-7 | 80 | 100 |
| 1-65 | 80 | 100 |
| 3-7 | 80 | 100 |
| 2-58 | 80 | 100 |
| 1-127 | 80 | 90 |
| 1-123 | 80 | 100 |
| 2-123 | 80 | 100 |
| 3-123 | 80 | 100 |
| 1-116 | 80 | 100 |
| 2-7 | 80 | 100 |
| 2-137 | 80 | 100 |
| 2-127 | 80 | 100 |
| 3-164 | 80 | 100 |
| 2-14 | 80 | 100 |
| 2-22 | 80 | 90 |
| 3-65 | 80 | 100 |
| 3-9 | 80 | 100 |
| 1-144 | 80 | 100 |
| 2-284 | 80 | 100 |
| 2-148 | 80 | 90 |
| 1-48 | 80 | 100 |
| 2-48 | 80 | 100 |
| 1-140 | 80 | 100 |
| 2-140 | 80 | 100 |
| 2-114 | 80 | 100 |
| 2-115 | 80 | 100 |
| 1-280 | 80 | 100 |
| 3-50 | 80 | 100 |
| 3-58 | 80 | 100 |
| 1-146 | 80 | 100 |
| 2-164 | 80 | 100 |
| 3-137 | 80 | 100 |
| 3-14 | 80 | 100 |
| 2-65 | 80 | 100 |
| 3-168 | 80 | 100 |
| 1-134 | 80 | 100 |
| 1-284 | 80 | 100 |
| 3-197 | 80 | 100 |
| 3-48 | 80 | 100 |
| 2-280 | 80 | 100 |
| 2-144 | 80 | 100 |
| 3-144 | 80 | 100 |
| 2-145 | 80 | 100 |
| 3-15 | 80 | 100 |
| 2-195 | 80 | 90 |
| 2-163 | 80 | 100 |
| 3-192 | 80 | 100 |
| 2-134 | 80 | 100 |
| 3-134 | 80 | 100 |
| 2-1 | 80 | 80 |
| 2-153 | 80 | 100 |
| 1-162 | 80 | 100 |
| 3-280 | 80 | 100 |
| 1-147 | 80 | 80 |
| 3-195 | 80 | 90 |
| 1-1 | 80 | 100 |
| 2-135 | 80 | 100 |
| 1-154 | 80 | 90 |
| 1-139 | 80 | 100 |
| 1-136 | 80 | 100 |
| 3-140 | 80 | 90 |
| 3-136 | 80 | 100 |
| 2-139 | 80 | 100 |
| 3-163 | 80 | 100 |
| 3-1 | 80 | 90 |
| 1-3 | 80 | 90 |
| 1-281 | 80 | 100 |
| 2-281 | 80 | 100 |
| 1-135 | 80 | 100 |
| 3-135 | 80 | 100 |
| 1-155 | 80 | 80 |
| 3-153 | 80 | 100 |
| 2-154 | 80 | 90 |
| 2-162 | 80 | 100 |
| 1-285 | 80 | 80 |
| 2-285 | 80 | 80 |
| 2-136 | 80 | 80 |
| 1-286 | 80 | 90 |
| 3-155 | 80 | 80 |
| 3-3 | 80 | 80 |
| 1-282 | 80 | 80 |
| 2-143 | 80 | 90 |
| 1-143 | 80 | 100 |
| 1-283 | 80 | 80 |

TABLE B32

Post-emergence action against VIOTR

| Example number | Dosage [g/ha] | VIOTR |
|---|---|---|
| 1-67 | 80 | 100 |
| 2-67 | 80 | 100 |
| 1-60 | 80 | 90 |
| 1-168 | 80 | 100 |
| 1-233 | 80 | 90 |
| 2-18 | 80 | 100 |
| 2-60 | 80 | 100 |
| 2-129 | 80 | 100 |
| 1-16 | 80 | 100 |
| 1-137 | 80 | 100 |
| 1-50 | 80 | 100 |
| 2-168 | 80 | 100 |
| 1-141 | 80 | 100 |
| 1-165 | 80 | 90 |
| 1-164 | 80 | 100 |
| 2-233 | 80 | 90 |
| 2-116 | 80 | 100 |
| 1-138 | 80 | 100 |
| 2-15 | 80 | 100 |
| 1-192 | 80 | 100 |
| 1-114 | 80 | 90 |
| 3-67 | 80 | 100 |
| 1-115 | 80 | 100 |
| 1-129 | 80 | 100 |
| 1-18 | 80 | 100 |
| 2-16 | 80 | 100 |
| 1-121 | 80 | 90 |
| 1-9 | 80 | 100 |
| 2-9 | 80 | 100 |
| 1-58 | 80 | 100 |
| 1-148 | 80 | 90 |
| 3-129 | 80 | 100 |
| 1-153 | 80 | 80 |
| 1-145 | 80 | 100 |
| 2-141 | 80 | 100 |
| 3-141 | 80 | 100 |
| 1-163 | 80 | 90 |
| 2-121 | 80 | 100 |
| 1-22 | 80 | 90 |
| 3-16 | 80 | 80 |
| 3-18 | 80 | 100 |
| 2-50 | 80 | 100 |
| 1-195 | 80 | 100 |

TABLE B32-continued

Post-emergence action against VIOTR

| Example number | Dosage [g/ha] | VIOTR |
|---|---|---|
| 1-7 | 80 | 100 |
| 1-65 | 80 | 100 |
| 3-7 | 80 | 100 |
| 2-58 | 80 | 100 |
| 1-127 | 80 | 100 |
| 1-123 | 80 | 100 |
| 2-123 | 80 | 100 |
| 3-123 | 80 | 100 |
| 1-116 | 80 | 90 |
| 2-7 | 80 | 100 |
| 2-137 | 80 | 100 |
| 2-127 | 80 | 100 |
| 3-164 | 80 | 100 |
| 2-14 | 80 | 100 |
| 2-22 | 80 | 100 |
| 3-65 | 80 | 100 |
| 3-9 | 80 | 100 |
| 1-144 | 80 | 100 |
| 2-284 | 80 | 80 |
| 2-148 | 80 | 90 |
| 1-48 | 80 | 100 |
| 2-48 | 80 | 100 |
| 1-140 | 80 | 100 |
| 2-140 | 80 | 100 |
| 2-114 | 80 | 100 |
| 2-115 | 80 | 100 |
| 1-280 | 80 | 90 |
| 3-50 | 80 | 100 |
| 3-58 | 80 | 100 |
| 1-146 | 80 | 90 |
| 2-164 | 80 | 100 |
| 3-137 | 80 | 100 |
| 3-14 | 80 | 100 |
| 2-65 | 80 | 100 |
| 3-168 | 80 | 100 |
| 1-134 | 80 | 100 |
| 1-284 | 80 | 100 |
| 3-197 | 80 | 100 |
| 3-48 | 80 | 100 |
| 2-280 | 80 | 90 |
| 2-144 | 80 | 100 |
| 3-144 | 80 | 80 |
| 2-145 | 80 | 100 |
| 3-15 | 80 | 90 |
| 2-195 | 80 | 100 |
| 2-163 | 80 | 100 |
| 3-192 | 80 | 100 |
| 2-134 | 80 | 100 |
| 3-134 | 80 | 90 |
| 2-1 | 80 | 100 |
| 2-153 | 80 | 90 |
| 1-162 | 80 | 100 |
| 3-280 | 80 | 80 |
| 3-195 | 80 | 90 |
| 1-1 | 80 | 100 |
| 2-135 | 80 | 90 |
| 1-154 | 80 | 80 |
| 1-139 | 80 | 100 |
| 1-136 | 80 | 90 |
| 3-140 | 80 | 100 |
| 3-136 | 80 | 80 |
| 2-139 | 80 | 100 |
| 3-163 | 80 | 80 |
| 3-1 | 80 | 100 |
| 1-287 | 80 | 90 |
| 1-281 | 80 | 100 |
| 2-281 | 80 | 90 |
| 1-135 | 80 | 90 |
| 2-286 | 80 | 80 |
| 2-162 | 80 | 100 |
| 2-136 | 80 | 80 |

TABLE B33

Post-emergence action against VERPE

| Example number | Dosage [g/ha] | VERPE |
|---|---|---|
| 1-67 | 80 | 100 |
| 2-67 | 80 | 90 |
| 1-60 | 80 | 100 |
| 1-168 | 80 | 100 |
| 1-233 | 80 | 100 |
| 2-18 | 80 | 80 |
| 2-60 | 80 | 100 |
| 2-129 | 80 | 100 |
| 1-16 | 80 | 90 |
| 1-137 | 80 | 90 |
| 1-50 | 80 | 100 |
| 2-168 | 80 | 80 |
| 1-141 | 80 | 100 |
| 1-165 | 80 | 90 |
| 1-164 | 80 | 100 |
| 2-233 | 80 | 100 |
| 2-116 | 80 | 90 |
| 1-138 | 80 | 90 |
| 2-15 | 80 | 90 |
| 1-114 | 80 | 100 |
| 3-67 | 80 | 80 |
| 1-115 | 80 | 100 |
| 1-129 | 80 | 100 |
| 1-18 | 80 | 100 |
| 2-16 | 80 | 80 |
| 1-121 | 80 | 100 |
| 1-9 | 80 | 100 |
| 2-9 | 80 | 100 |
| 1-58 | 80 | 100 |
| 1-148 | 80 | 100 |
| 3-129 | 80 | 100 |
| 1-153 | 80 | 80 |
| 1-145 | 80 | 100 |
| 2-141 | 80 | 80 |
| 3-141 | 80 | 100 |
| 1-163 | 80 | 90 |
| 2-121 | 80 | 100 |
| 1-22 | 80 | 80 |
| 3-16 | 80 | 80 |
| 3-18 | 80 | 80 |
| 2-50 | 80 | 90 |
| 1-195 | 80 | 80 |
| 1-7 | 80 | 100 |
| 1-65 | 80 | 100 |
| 3-7 | 80 | 100 |
| 2-58 | 80 | 100 |
| 1-127 | 80 | 100 |
| 1-123 | 80 | 100 |
| 2-123 | 80 | 100 |
| 3-123 | 80 | 100 |
| 2-7 | 80 | 100 |
| 2-137 | 80 | 90 |
| 2-127 | 80 | 100 |
| 2-14 | 80 | 80 |
| 2-22 | 80 | 80 |
| 3-65 | 80 | 80 |
| 3-9 | 80 | 100 |
| 1-144 | 80 | 90 |
| 2-284 | 80 | 80 |
| 2-148 | 80 | 90 |
| 1-48 | 80 | 80 |
| 2-48 | 80 | 80 |
| 1-140 | 80 | 80 |

TABLE B33-continued

Post-emergence action against VERPE

| Example number | Dosage [g/ha] | VERPE |
|---|---|---|
| 2-140 | 80 | 80 |
| 2-114 | 80 | 80 |
| 1-280 | 80 | 90 |
| 3-50 | 80 | 100 |
| 3-58 | 80 | 80 |
| 1-146 | 80 | 90 |
| 3-137 | 80 | 90 |
| 3-14 | 80 | 80 |
| 2-65 | 80 | 80 |
| 1-134 | 80 | 100 |
| 1-284 | 80 | 90 |
| 3-197 | 80 | 80 |
| 3-48 | 80 | 80 |
| 2-144 | 80 | 90 |
| 3-144 | 80 | 80 |
| 3-15 | 80 | 90 |
| 2-134 | 80 | 90 |
| 3-134 | 80 | 90 |
| 1-154 | 80 | 80 |
| 1-139 | 80 | 80 |
| 1-136 | 80 | 90 |
| 3-136 | 80 | 80 |
| 1-3 | 80 | 90 |
| 1-281 | 80 | 80 |
| 2-281 | 80 | 80 |
| 1-135 | 80 | 80 |
| 1-14 | 80 | 80 |

TABLE B34

Post-emergence action against HORMU

| Example number | Dosage [g/ha] | HORMU |
|---|---|---|
| 1-67 | 80 | 100 |
| 2-67 | 80 | 80 |
| 1-60 | 80 | 100 |
| 1-168 | 80 | 100 |
| 1-233 | 80 | 80 |
| 2-18 | 80 | 100 |
| 2-60 | 80 | 100 |
| 2-233 | 80 | 90 |
| 1-192 | 80 | 100 |
| 3-67 | 80 | 80 |

3. Comparative Experiments

The herbicidal activity against harmful plants by the pre- and post-emergence method of some of the compounds disclosed in WO 2012/028579 A1 was compared to that of the structurally closest compounds according to the invention. The data of these comparative experiments demonstrate the superiority of the compounds according to the invention.

TABLE V1 pre-emergence

| | Dosage | Herbicidal efficacy against | | | |
|---|---|---|---|---|---|
| Example No. | (g of a.i./ha) | ALOMY | CYPES | POLCO | VIOTR |
| 1-127, according to the invention | 80 | 80 | 90 | 70 | 100 |
| 4-250, from D1 | 80 | 20 | 60 | 0 | 50 |

TABLE V2 pre-emergence

| Example No. | Dosage (g of a.i./ha) | ECHCG | SETVI | AMARE | MATIN | VERPE |
|---|---|---|---|---|---|---|
| 1-129, according to the invention | 20 | 90 | 90 | 90 | 90 | 100 |
| 4-250, from D1 | 20 | 40 | 10 | 60 | 30 | 50 |

TABLE V3 pre-emergence

| | Dosage | Herbicidal efficacy against | | | | | | |
|---|---|---|---|---|---|---|---|---|
| Example No. | (g of a.i./ha) | ALOMY | CYPES | ECHCG | ABUTH | AMARE | MATIN | VIOTR |
| 1-127 | 80 | 80 | 90 | 100 | 100 | 100 | 90 | 100 |
| 4-251, from D1 | 80 | 0 | 20 | 20 | 50 | 70 | 70 | 0 |
| 1-129 | 80 | 100 | 100 | 100 | 100 | 100 | 100 | 100 |
| 4-251, from D1 | 80 | 0 | 20 | 20 | 50 | 70 | 70 | 0 |

TABLE V4 pre-emergence

| Example No. | Dosage (g of a.i./ha) | Herbicidal efficacy against | | | |
|---|---|---|---|---|---|
| | | ABUTH | MATIN | STEME | VERPE |
| 1-127, according to the invention | 20 | 90 | 70 | 70 | 90 |
| 4-251, from D1 | 20 | 40 | 0 | 30 | 40 |

TABLE V5 pre-emergence

| Example No. | Dosage (g of a.i./ha) | Herbicidal efficacy against | |
|---|---|---|---|
| | | MATIN | VIOTR |
| 1-7, according to the invention | 20 | 90 | 100 |
| 4-908, from D1 | 20 | 20 | 20 |

TABLE V6 pre-emergence

| Example No. | Dosage (g of a.i./ha) | Herbicidal efficacy against | | |
|---|---|---|---|---|
| | | CYPES | PHBPU | POLCO |
| 1-9, according to the invention | 80 | 70 | 60 | 40 |
| 4-908, from D1 | 80 | 10 | 40 | 10 |

TABLE V7 pre-emergence

| Example No. | Dosage (g of a.i./ha) | Herbicidal efficacy against | | |
|---|---|---|---|---|
| | | ABUTH | MATIN | VIOTR |
| 1-9, according to the invention | 20 | 100 | 90 | 70 |
| 4-908, from D1 | 20 | 80 | 20 | 20 |
| 2-9, according to the invention | 20 | 100 | 80 | 90 |
| 5-826, from D1 | 20 | 60 | 0 | 0 |

TABLE V8 pre-emergence

| Example No. | Dosage (g of a.i./ha) | Herbicidal efficacy against | | | | | |
|---|---|---|---|---|---|---|---|
| | | ECHCG | AMARE | MATIN | STEME | VIOTR | VERPE |
| 1-7, according to the invention | 20 | 70 | 100 | 90 | 90 | 100 | 100 |
| 4-933, from D1 | 20 | 0 | 80 | 40 | 60 | 0 | 0 |

TABLE V9 pre-emergence

| Example No. | Dosage (g of a.i./ha) | Herbicidal efficacy against | |
|---|---|---|---|
| | | SETVI | VIOTR |
| 1-9, according to the invention | 80 | 100 | 100 |
| 4-933, from D1 | 80 | 0 | 0 |

TABLE V10 pre-emergence

| Example No. | Dosage (g of a.i./ha) | Herbicidal efficacy against | | | | |
|---|---|---|---|---|---|---|
| | | ALOMY | CYPES | SETVI | MATIN | STEME |
| 2-7, according to the invention | 80 | 70 | 90 | 80 | 100 | 90 |
| 5-826, from D1 | 80 | 30 | 0 | 0 | 80 | 70 |

TABLE V11

| | pre-emergence | |
|---|---|---|
| Example No. | Dosage (g of a.i./ha) | Herbicidal efficacy against CYPES |
| 2-7, according to the invention | 80 | 90 |
| 5-827, from D1 | 80 | 60 |

TABLE V12

| | pre-emergence | |
|---|---|---|
| Example No. | Dosage (g of a.i./ha) | Herbicidal efficacy against VIOTR |
| 2-7, according to the invention | 20 | 90 |
| 5-827, from D1 | 20 | 70 |

TABLE V13

| | pre-emergence | | |
|---|---|---|---|
| | Dosage | Herbicidal efficacy against | |
| Example No. | (g of a.i./ha) | AMARE | VIOTR |
| 2-9, according to the invention | 20 | 100 | 90 |
| 5-827, from D1 | 20 | 80 | 70 |

TABLE V14

| | post-emergence | | |
|---|---|---|---|
| | Dosage | Herbicidal efficacy against | |
| Example No. | (g of a.i./ha) | AMARE | MATIN |
| 1-127, according to the invention | 5 | 100 | 90 |
| 4-250, from D1 | 5 | 0 | 20 |

TABLE V15

| | post-emergence | | | | | |
|---|---|---|---|---|---|---|
| | Dosage | Herbicidal efficacy against | | | | |
| Example No. | (g of a.i./ha) | ALOMY | AVEFA | CYPES | SETVI | AMARE | MATIN |
| 1-129, according to the invention | 5 | 70 | 60 | 60 | 100 | 100 | 80 |
| 4-250, from D1 | 5 | 20 | 20 | 40 | 80 | 0 | 20 |
| 1-129, according to the invention | 5 | 70 | 60 | 60 | 100 | 100 | 80 |
| 4-251, from D1 | 5 | 0 | 0 | 30 | 0 | 80 | 0 |

TABLE V16

| | post-emergence | | | | |
|---|---|---|---|---|---|
| | Dosage | Herbicidal efficacy against | | | |
| Example No. | (g of a.i./ha) | ECHCG | MATIN | PHBPU | VIOTR |
| 1-127, according to the invention | 20 | 100 | 100 | 100 | 100 |
| 4-251, from D1 | 20 | 80 | 30 | 60 | 50 |
| 1-127, according to the invention | 5 | 100 | 90 | 70 | 100 |
| 4-251, from D1 | 5 | 50 | 0 | 40 | 20 |

TABLE V17

| | post-emergence | | |
|---|---|---|---|
| | Dosage | Herbicidal efficacy against | |
| Example No. | (g of a.i./ha) | MATIN | VIOTR |
| 1-7, according to the invention | 5 | 100 | 100 |
| 4-908, from D1 | 5 | 80 | 80 |
| 1-9, according to the invention | 5 | 100 | 100 |
| 4-908, from D1 | 5 | 80 | 80 |
| 1-7, according to the invention | 5 | 100 | 100 |
| 4-933, from D1 | 5 | 60 | 60 |
| 2-7, according to the invention | 5 | 100 | 100 |
| 5-826, from D1 | 5 | 70 | 80 |
| 2-9, according to the invention | 5 | 90 | 100 |
| 5-826, from D1 | 5 | 70 | 80 |

TABLE V18

| | Dosage | Herbicidal efficacy against | | | | | | |
|---|---|---|---|---|---|---|---|---|
| Example No. | (g of a.i./ha) | ALOMY | AVEFA | CYPES | SETVI | MATIN | PHBPU | STEME |
| 1-9, according to the invention | 20 | 80 | 80 | 70 | 100 | 100 | 100 | 100 |
| 4-933, from D1 | 20 | 30 | 60 | 10 | 80 | 70 | 80 | 80 |

TABLE V19 post-emergence

| Example No. | Dosage (g of a.i./ha) | SETVI | ABUTH | MATIN | STEME | VIOTR |
|---|---|---|---|---|---|---|
| 2-7, according to the invention | 5 | 90 | 100 | 100 | 100 | 100 |
| 5-826, from D1 | 5 | 40 | 60 | 70 | 30 | 80 |

TABLE V20

| | Dosage | Herbicidal efficacy against | | | |
|---|---|---|---|---|---|
| Example No. | (g of a.i./ha) | ALOMY | CYPES | ABUTH | POLCO |
| 2-9, according to the invention | 80 | 90 | 90 | 90 | 100 |
| 5-826, from D1 | 80 | 70 | 0 | 60 | 60 |

TABLE V21

| | Dosage | Herbicidal efficacy against | | |
|---|---|---|---|---|
| Example No. | (g of a.i./ha) | ABUTH | AMARE | STEME |
| 2-7, according to the invention | 5 | 100 | 100 | 100 |
| 5-827, from D1 | 5 | 70 | 70 | 70 |

The invention claimed is:

1. 3-Acylbenzamide of formula (I)

(I)

in which the symbols and indices are defined as follows:
$R^x$ represents $(C_1-C_6)$-alkyl,
X represents halogen, $(C_1-C_6)$-alkyl, halo-$(C_1-C_6)$-alkyl, $(C_3-C_6)$-cycloalkyl, $R^1O$, $R^2S(O)_n$ or $R^1O$—$(C_1-C_6)$-alkyl,
Y represents halogen, $(C_1-C_6)$-alkyl, halo-$(C_1-C_6)$-alkyl or $R^1O$, $R^2S(O)_n$,
Z represents $(C_1-C_6)$-alkyl, $(C_3-C_6)$-cycloalkyl, $(C_2-C_6)$-alkenyl, $(C_3-C_6)$-alkynyl, halo-$(C_1-C_6)$-alkyl, $(C_1-C_6)$-alkyl-O—$(C_1-C_6)$-alkyl, $(C_1-C_6)$-alkyl-C(O), $(C_1-C_6)$-alkyl-C(O)—$(C_1-C_6)$-alkyl, phenyl or heterocyclyl, where the radicals phenyl, heterocyclyl, $(C_2-C_6)$-alkenyl, $(C_3-C_6)$-alkynyl and $(C_3-C_6)$-cycloalkyl each carry m substituents $R^3$,
$R^1$ represents $(C_1-C_6)$-alkyl or halo-$(C_1-C_6)$-alkyl,
$R^2$ represents $(C_1-C_6)$-alkyl,
$R^3$ represents halogen, $(C_1-C_6)$-alkyl, $(C_1-C_3)$-alkyl-O—C(O), cyano or halo-$(C_1-C_6)$-alkyl,
m represents 0, 1, 2, 3 or 4,
n represents 0, 1 or 2.

2. 3-Acylbenzamide according to claim 1 in which
$R^x$ represents $(C_1-C_6)$-alkyl,
X represents halogen, $(C_1-C_6)$-alkyl, halo-$(C_1-C_6)$-alkyl, $(C_3-C_6)$-cycloalkyl, $R^1O$, $R^2S(O)_n$ or $R^1O$—$(C_1-C_6)$-alkyl,
Y represents halogen, $(C_1-C_6)$-alkyl, halo-$(C_1-C_6)$-alkyl or $R^1O$, $R^2S(O)_n$,
Z represents $(C_1-C_6)$-alkyl, $(C_3-C_6)$-cycloalkyl, $(C_2-C_6)$-alkenyl, $(C_3-C_6)$-alkynyl, halo-$(C_1-C_6)$-alkyl, $(C_1-C_6)$-alkyl-O—$(C_1-C_6)$-alkyl, $(C_1-C_6)$-alkyl-C(O), $(C_1-C_6)$-alkyl-C(O)—$(C_1-C_6)$-alkyl or phenyl, where the radicals phenyl, $(C_2-C_6)$-alkenyl, $(C_3-C_6)$-alkynyl and $(C_3-C_6)$-cycloalkyl each carry m substituents $R^3$,
$R^1$ represents $(C_1-C_6)$-alkyl or halo-$(C_1-C_6)$-alkyl,
$R^2$ represents $(C_1-C_6)$-alkyl,
$R^3$ represents halogen, $(C_1-C_6)$-alkyl, $(C_1-C_3)$-alkyl-O—C(O), cyano or halo-$(C_1-C_6)$-alkyl,
m represents 0, 1, 2, 3 or 4,
n represents 0, 1 or 2.

3. 3-Acylbenzamide according to claim 1 in which
$R^x$ represents $(C_1-C_6)$-alkyl,
X represents fluorine, chlorine, bromine, iodine, methyl, ethyl, cyclopropyl, trifluoromethyl, difluoromethyl, methoxymethyl, methoxy, methylsulfanyl, methylsulfinyl, methyl sulfonyl, ethylsulfanyl or ethyl sulfonyl,
Y represents chlorine, bromine, iodine, methyl, ethyl, trifluoromethyl, difluoromethyl, methylsulfanyl, methylsulfinyl, methyl sulfonyl or ethyl sulfonyl,
Z represents methyl, ethyl, n-propyl, isopropyl, cyclopropyl, n-butyl, tert-butyl, methoxymethyl, chloromethyl, acetyl, vinyl, 1-methylvinyl, 2-methylvinyl, (1,2-dimethyl)vinyl, (2,2-dimethyl)vinyl, 1-methylcyclopropyl, 2-methylcyclopropyl, (2,2-dimethyl)cyclopropyl, (1,2-dimethyl)cyclopropyl, 2-fluorocyclopropyl, (2,2-difluoro)cyclopropyl, cyclobutyl, cyclopentyl, cyclohexyl, 2-thienyl, 2-furyl, phenyl, 4-methoxyphenyl, 4-chlorophenyl, (3-trifluoromethyl)phenyl, 3,5-difluorophenyl, trifluoromethyl or difluoromethyl.

4. Herbicidal composition comprising at least one compound according to claim 1 mixed with one or more formulation auxiliaries.

5. Herbicidal composition according to claim 4, comprising at least one further pesticidally active substance selected from the group consisting of insecticides, acaricides, herbicides, fungicides, safeners and growth regulators.

6. Method for controlling one or more unwanted plants, comprising applying an effective amount of at least one compound of the formula (I) according to claim 1 or a herbicidal composition thereof to the plants or a site of unwanted vegetation.

7. A product comprising one or more compounds of the formula (I) according to claim 1 or a herbicidal composition thereof for controlling one or more unwanted plants.

8. Product according to claim 7 wherein the compound of the formula (I) is used for controlling said unwanted plants in one or more crops of useful plants.

9. Product according to claim 8, wherein the useful plants are transgenic useful plants.

10. 3-Acylbenzamide according to claim 3 wherein $R^x$ represents methyl.

11. 3-Acylbenzamide according to claim 3 wherein X represents methyl.

12. 3-Acylbenzamide according to claim 3 wherein Y represents methyl sulfonyl.

13. 3-Acylbenzamide according to claim 3 wherein Z represents cyclopropyl.

* * * * *